US011110000B2

(12) United States Patent
Wilkerson et al.

(10) Patent No.: US 11,110,000 B2
(45) Date of Patent: Sep. 7, 2021

(54) SPRAY EJECTOR MECHANISMS AND DEVICES PROVIDING CHARGE ISOLATION AND CONTROLLABLE DROPLET CHARGE, AND LOW DOSAGE VOLUME OPHTHALMIC ADMINISTRATION

(71) Applicant: EYENOVIA, INC., New York, NY (US)

(72) Inventors: Jonathan Ryan Wilkerson, Raleigh, NC (US); Iyam Lynch, Boone, NC (US); Charles Eric Hunter, Boone, NC (US); Joshua Richard Brown, Hickory, NC (US); Lucien S. Wilkins, Boone, NC (US); Peter Lam, Raleigh, NC (US); Hamilton Coleman, Boone, NC (US); J. Sid Clements, Boone, NC (US); Bernard L. Ballou, Jr., Raleigh, NC (US)

(73) Assignee: EYENOVIA, INC., Tampa, FL (US)

( * ) Notice: Subject to any disclaimer, the term of this patent is extended or adjusted under 35 U.S.C. 154(b) by 103 days.

(21) Appl. No.: 13/882,962

(22) PCT Filed: Apr. 10, 2013

(86) PCT No.: PCT/US2013/036002
§ 371 (c)(1),
(2) Date: May 1, 2013

(87) PCT Pub. No.: WO2013/155201
PCT Pub. Date: Oct. 17, 2013

(65) Prior Publication Data
US 2014/0336618 A1    Nov. 13, 2014

Related U.S. Application Data

(60) Provisional application No. 61/622,148, filed on Apr. 10, 2012, provisional application No. 61/642,867, (Continued)

(51) Int. Cl.
*A61F 9/00* (2006.01)
*A61M 11/00* (2006.01)
(Continued)

(52) U.S. Cl.
CPC ......... *A61F 9/0008* (2013.01); *A61M 11/005* (2013.01); *A61M 15/025* (2014.02);
(Continued)

(58) Field of Classification Search
CPC ......... A61H 33/04; A61M 1/00; A61M 35/00; B67D 7/60; B65D 47/10
See application file for complete search history.

(56) References Cited

U.S. PATENT DOCUMENTS 3,892,235 A   7/1975   Van Amerongen et al.
4,533,082 A   8/1985   Maehara et al.
(Continued)

FOREIGN PATENT DOCUMENTS

CA   1339281   8/1997
CA   2394664   6/2000
(Continued)

OTHER PUBLICATIONS

Santvliet et al., "Determinants of Eye Drop Size," Survey of Ophthalmology, Mar.-Apr. 2004,pp. 197-211, vol. 49.
(Continued)

*Primary Examiner* — Tatyana Zalukaeva
*Assistant Examiner* — Ilya Y Treyger

(57) ABSTRACT

The present disclosure relates to ejector mechanisms and devices for generating a directed stream of droplets, as well
(Continued)

as improved methods for delivering an ejected stream of droplets to a target. The device and methods may be useful for the delivery of fluid for ophthalmic, topical, oral, nasal, or pulmonary use, more particularly, for use in the delivery of ophthalmic fluid to the eye. Certain aspects of the disclosure relate to devices and methods for the delivery of a therapeutically effective low dosage volume medicament composition to a target, e.g., by controlling charge, droplet size and/or droplet deposit parameters of the medicament composition.

28 Claims, 55 Drawing Sheets

Related U.S. Application Data filed on May 4, 2012, provisional application No. 61/722,589, filed on Nov. 5, 2012, provisional application No. 61/736,948, filed on Dec. 13, 2012.

(51) Int. Cl.
*A61M 15/02* (2006.01)
*B05B 17/00* (2006.01)
*A61H 33/04* (2006.01)
*A61M 1/00* (2006.01)
*A61M 35/00* (2006.01)
*B67D 7/60* (2010.01)
*B65D 47/10* (2006.01)

(52) U.S. Cl.
CPC . *B05B 17/0646* (2013.01); *A61M 2205/8206* (2013.01); *A61M 2210/0612* (2013.01)

(56) References Cited

U.S. PATENT DOCUMENTS

| | | | |
|---|---|---|---|
| 5,024,355 A | 6/1991 | Jouillat et al. |
| 5,296,673 A | 3/1994 | Smith |
| 5,518,179 A | 5/1996 | Humberstone et al. |
| 5,607,410 A | 3/1997 | Branch |
| 5,630,793 A | 5/1997 | Rowe |
| 6,011,062 A | 1/2000 | Schneider et al. |
| 6,530,370 B1 | 3/2003 | Heinonen |
| 6,550,472 B2 | 4/2003 | Litherland et al. |
| 6,921,020 B2 | 7/2005 | Ivri |
| 6,976,639 B2 | 12/2005 | Williams et al. |
| 7,367,334 B2 | 5/2008 | Faison, Jr. et al. |
| 7,448,559 B2 | 11/2008 | Le Maner et al. |
| 7,828,232 B2 | 11/2010 | Oomori et al. |
| 7,883,031 B2 | 2/2011 | Collins, Jr. et al. |
| 7,954,486 B2 | 6/2011 | Papania et al. |
| 8,012,136 B2 | 9/2011 | Collins, Jr. et al. |
| 8,485,503 B2 | 7/2013 | Lei |
| 8,545,463 B2 | 10/2013 | Collins, Jr. et al. |
| 8,684,980 B2 | 4/2014 | Hunter et al. |
| 2002/0085067 A1 | 7/2002 | Palifka et al. |
| 2003/0116642 A1 | 6/2003 | Williams et al. |
| 2004/0039355 A1 | 2/2004 | Gonzalez et al. |
| 2004/0163641 A1 | 8/2004 | Tyvoll et al. |
| 2004/0215157 A1 | 10/2004 | Peclat et al. |
| 2004/0256487 A1 | 12/2004 | Collins et al. |
| 2005/0211797 A1 | 9/2005 | Abergel et al. |
| 2006/0011737 A1 | 1/2006 | Amenos et al. |
| 2006/0243820 A1 | 11/2006 | Ng |
| 2007/0211212 A1 | 9/2007 | Bennwik |
| 2008/0043061 A1 | 2/2008 | Glezer et al. |
| 2008/0303850 A1 | 12/2008 | Shin et al. |
| 2009/0035591 A1* | 2/2009 | Nishikawa .............. B32B 15/08 428/458 |
| 2009/0114742 A1 | 5/2009 | Collins, Jr. |
| 2009/0149829 A1 | 6/2009 | Collins, Jr. |
| 2009/0167812 A1 | 7/2009 | Asai et al. |
| 2009/0212133 A1 | 8/2009 | Collins, Jr. |
| 2009/0272818 A1 | 11/2009 | Valpey et al. |
| 2010/0211408 A1 | 8/2010 | Park et al. |
| 2010/0222752 A1 | 9/2010 | Collins, Jr. et al. |
| 2011/0175971 A1 | 7/2011 | Newton et al. |
| 2011/0233302 A1 | 9/2011 | Lin et al. |
| 2011/0254901 A1 | 10/2011 | Sakai |
| 2012/0062840 A1 | 3/2012 | Ballou, Jr. et al. |
| 2012/0070467 A1 | 3/2012 | Ballou, Jr. et al. |
| 2012/0143152 A1 | 6/2012 | Hunter et al. |
| 2013/0150812 A1 | 6/2013 | Hunter et al. |
| 2013/0172830 A1 | 7/2013 | Hunter et al. |
| 2013/0299607 A1 | 11/2013 | Wilkerson et al. |
| 2013/0334335 A1 | 12/2013 | Wilkerson et al. |
| 2014/0336618 A1 | 11/2014 | Wilkerson et al. |
| 2014/0361095 A1 | 12/2014 | Haran |

FOREIGN PATENT DOCUMENTS

| | | | |
|---|---|---|---|
| CA | 2458596 | | 3/2003 |
| CA | 2500252 | | 4/2004 |
| CA | 2709928 | | 7/2009 |
| CN | 1483225 | | 3/2004 |
| CN | 1854503 | | 11/2006 |
| CN | 101137446 | | 3/2008 |
| CN | 101274850 | | 10/2008 |
| CN | 101479046 | | 7/2009 |
| CN | 101843944 | | 9/2010 |
| CN | 101910608 | | 12/2010 |
| CN | 102180013 | | 9/2011 |
| EP | 1219314 | | 7/2002 |
| EP | 2253322 | * | 11/2010 |
| FR | 2934128 | | 1/2010 |
| JP | S62-142110 | | 6/1987 |
| JP | 2008-515625 | | 5/2008 |
| JP | 2012-508129 | | 4/2012 |
| WO | WO 95/15822 | | 6/1995 |
| WO | WO 2010/141118 | | 12/2010 |
| WO | WO 2011/058955 | | 5/2011 |
| WO | WO 2011/083379 | | 7/2011 |
| WO | WO 2012/009706 A1 | * | 7/2011 |
| WO | WO 2012/009696 | | 1/2012 |
| WO | WO 2012/009702 | | 1/2012 |
| WO | WO 2012/009706 | | 1/2012 |
| WO | WO 2013/090468 | | 6/2013 |

OTHER PUBLICATIONS

Brown et al., "The Preservation of Ophthalmic Preparations," Journal of the Society of Cosmetic Chemists, 1965, pp. 369-393, vol. 16.

* cited by examiner

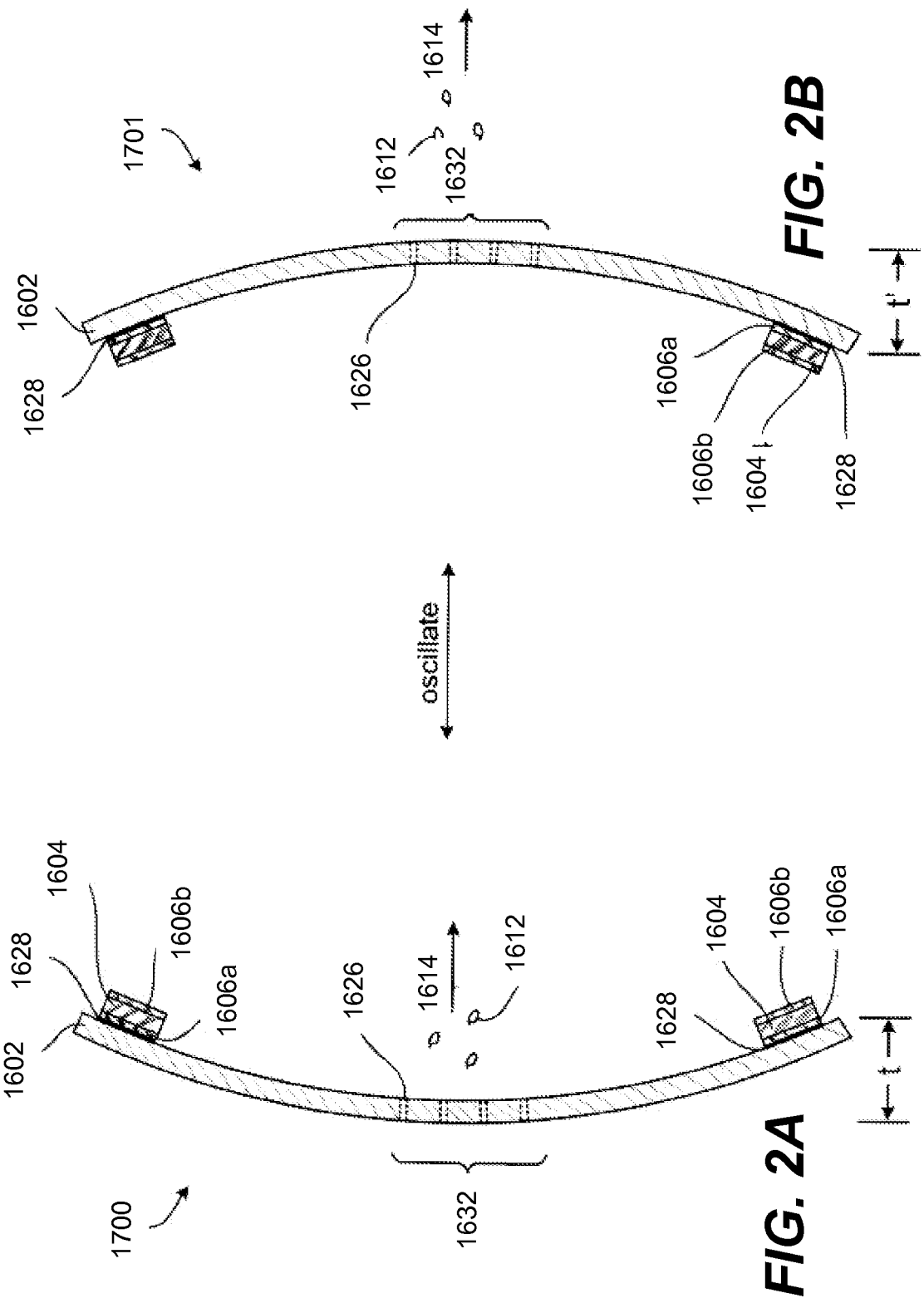

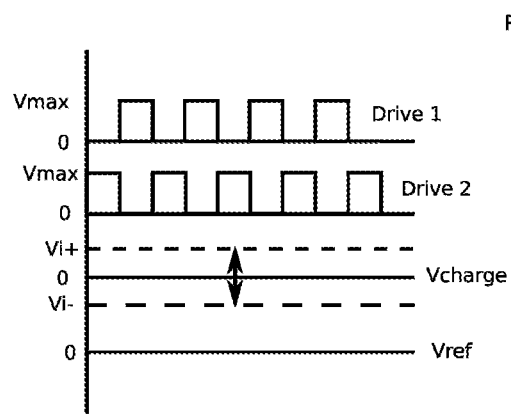
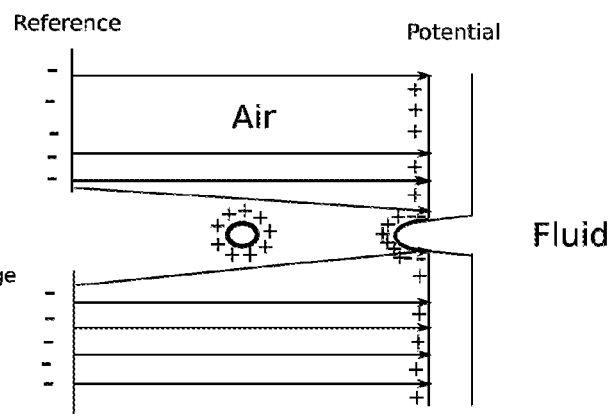
FIG. 4A  FIG. 4B
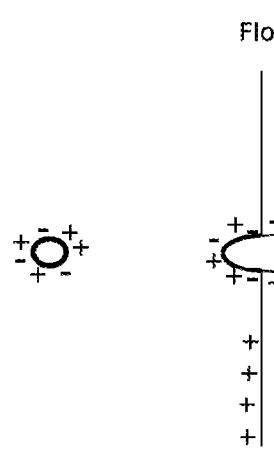
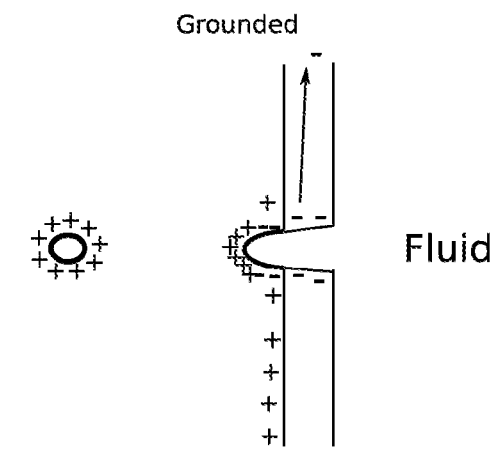
FIG. 4C  FIG. 4D

1.) Hot press Laminate Copper / PEEK / Copper

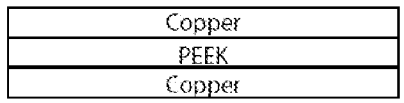

*Supplied by Roger's or FPC company

2.) Bond FPC to Copper / PEEK / Copper with Adhesive

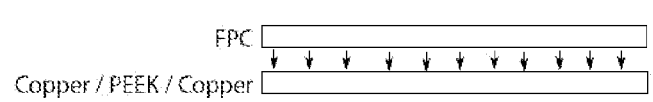

3.) Etch exposed top copper and bottom copper off PEEK laminate. Leave Copper outside of flex circuits to assist in preventing panel curling during processing. Yellow are as etched at same time. Green areas not etched to prevent panel curl.

FIG. 12

1.) Bond FPC to DLC coated SS316L with Adhesive

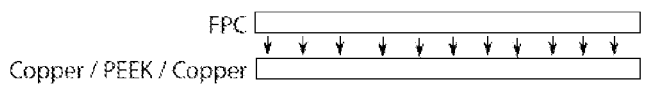

2.) Punch 2mm radius center out of DLC coated316L annulus (shown in green)

FIG. 13

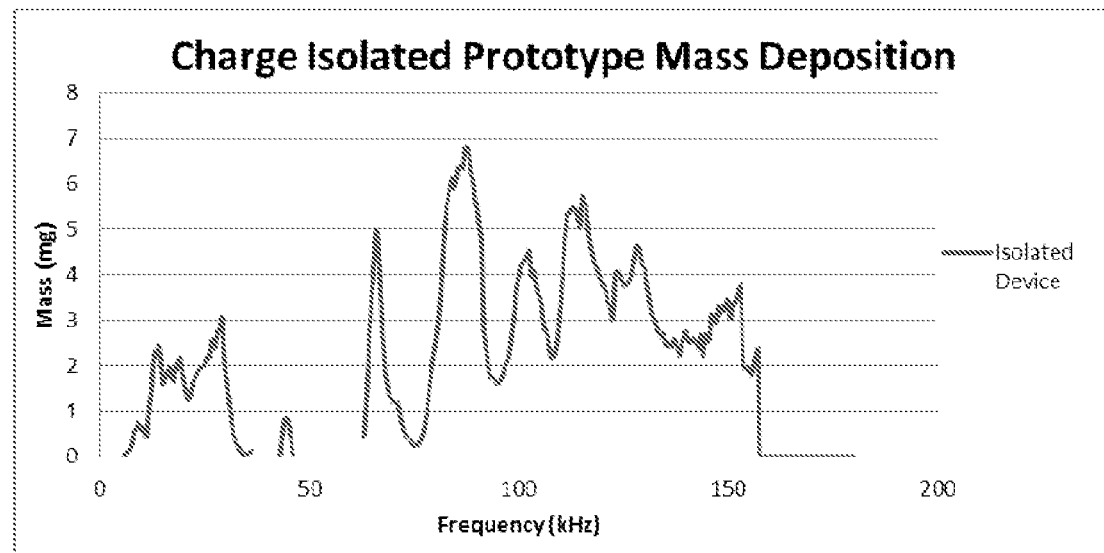
FIG. 29
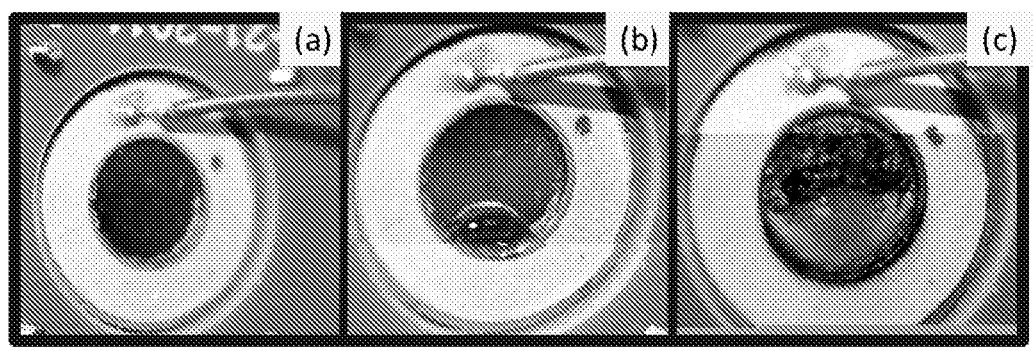
FIG. 30A-C

SPRAY EJECTOR MECHANISMS AND DEVICES PROVIDING CHARGE ISOLATION AND CONTROLLABLE DROPLET CHARGE, AND LOW DOSAGE VOLUME OPHTHALMIC ADMINISTRATION

RELATED APPLICATIONS

This application is the national stage application of PCT Patent Application No. PCT/US2013/036002 filed on Apr. 10, 2013, which claims the benefit under 35 U.S.C. § 119(e) of U.S. Provisional Application Nos. 61/736,948, filed Dec. 13, 2012; 61/722,589, filed Nov. 5, 2012; 61/642,867, filed May 4, 2012; and 61/622,148, filed Apr. 10, 2012, the contents of which are herein incorporated by reference in their entireties.

BACKGROUND OF THE DISCLOSURE

Using spray devices to administer products in the form of mists or sprays is an area with large potential for safe, ease-of-use products. However, a major challenge in providing such a device is to provide consistent and accurate delivery of suitable doses. An important area where spray devices are needed is in delivery of eye medications.

Traditional application of fluids to the eye, as in the case of eye drops, has always posed a problem, particularly for children and animals that tend to blink or jerk at the critical moment of administration, causing the droplet to land on the eyelid, nose or other part of the face. The impact of a large drop or drops of fluid on the eyeball, particularly when the fluid is at a different temperature, also tends to produce a blinking reaction. Elderly, disabled, and stroke victims also often lose the dexterity and coordination necessary to properly administer eye drops. In addition, with unfavorable administration, subject compliance can be problematic.

More particularly, a typical medical droplet as dispensed by an eye dropper bottle can vary, depending on the viscosity and surface tension of the fluid. In order to control the amount of active ingredient that is administered in a single droplet, the concentration of the active ingredient is adjusted by volume. Once the concentration is defined, a correct dosage may require one drop or more. However, since the human eye can typically retain only 7 µl of fluid at a time, even a single medical droplet can result in overflow and loss of part of the medication from the eye. Multiple drop dosage often compounds the problem of medication retention in the eye. Subjects will typically administer all droplets required for a dosage in one sitting, which exacerbates the problem and can result in 50 to 90% of the medication overflowing and leaking out of the eye.

Another problem is that a single droplet of the defined concentration marks the lower limit of a dose and, as such, the amount of active ingredient that can be administered at the defined concentration. For example, pediatric applications where lower doses are often advisable are an illustration of where the size/dose of a droplet can be problematic.

Accordingly, there is a need to develop a delivery device that provides safe, suitable, and repeatable dosages to a subject for ophthalmic, topical, oral, nasal, or pulmonary use.

SUMMARY OF THE DISCLOSURE

In certain aspects, the disclosure relates to methods for delivering a low dosage volume medicament composition to the eye of a subject in need thereof by controlling droplet charge, droplet size and/or droplet deposit parameters of the medicament composition. In this regard, using ejector devices of the present disclosure, low dosage volume medicament compositions may be deposited on the eye of a subject in a reproducible manner, e.g., as compared to standard eyedropper use and dosage volumes.

In one aspect, the disclosure relates to a method of delivering a low dosage volume medicament composition to an eye of a subject in need thereof, as compared to dosage volume of a standard eyedropper, the method comprising: (a) generating droplets including the low dosage volume medicament composition with a controllable droplet charge; and (b) delivering the droplets including the low dosage volume medicament composition to the eye of the subject, wherein the controllable droplet charge improves delivery of the droplets to the eye of the subject, as compared to delivery via standard eyedropper.

In another aspect, the disclosure relates to a method of delivering a low dosage volume medicament composition to an eye of a subject in need thereof, as compared to dosage volume of a standard eye dropper, the method comprising: (a) generating droplets including the low dosage volume medicament composition, wherein said droplets have an average drop size of between about 15 microns and about 100 microns in diameter and an average ejecting velocity of between about 0.5 m/s to about 20 m/s; and (b) delivering the droplets including the low dosage volume medicament composition to the eye of the subject, wherein between about 80% to about 100% of the ejected mass of the droplets are deposited on the eye.

In certain other aspects, the disclosure relates to a spray ejector mechanism and ejector device which controllably charges ejected droplets to thereby improve delivery of ejected droplets to a desired surface of administration, e.g., tissue or biological surface.

In certain embodiments, the spray ejector mechanism and ejector device is configured to provide controllable charge to ejected droplets upon administration of the ejected droplets, without charging droplet fluid while in storage prior to administration, thereby minimizing potential physical and chemical interactions, degradation, denaturing, etc. of the droplet fluid during storage due to charge.

In yet other aspects, the disclosure relates to an ejector mechanism and ejector device which provides suppression or elimination of electro-wetting, induction charging induced droplet recapture, and chemical alterations due to localized charging and discharging of fluids.

These and other aspects of the invention will become apparent to one of skill in the art.

BRIEF DESCRIPTION OF THE DRAWINGS

FIGS. 2A-2B illustrate a cross-sectional view of an activated ejector plate for an ejector device according to certain aspects of the disclosure.

FIGS. 4A-4D illustrate induced charging and tribocharging of a droplet, and associated ejector system drive signals according to certain aspects of the disclosure.

FIG. 8 illustrates an exploded top view of the embodiment of FIG. 7B according to certain aspects of the disclosure.

FIG. 12 illustrates a FPC/PEEK charge isolated ejector assembly and process according to certain aspects of the disclosure.

FIG. 13 illustrates a FPC/SS charge isolated ejector assembly and process according to certain aspects of the disclosure.

FIG. 29 shows a plot of mass deposition for a charge isolated ejector device according to an implementation according to the present disclosure.

FIG. 30A-30C shows images of the effect of driving the oscillating plate and grounding the piezoelectric electrode according to an implementation according to the present disclosure.

DETAILED DESCRIPTION

Figure 1:
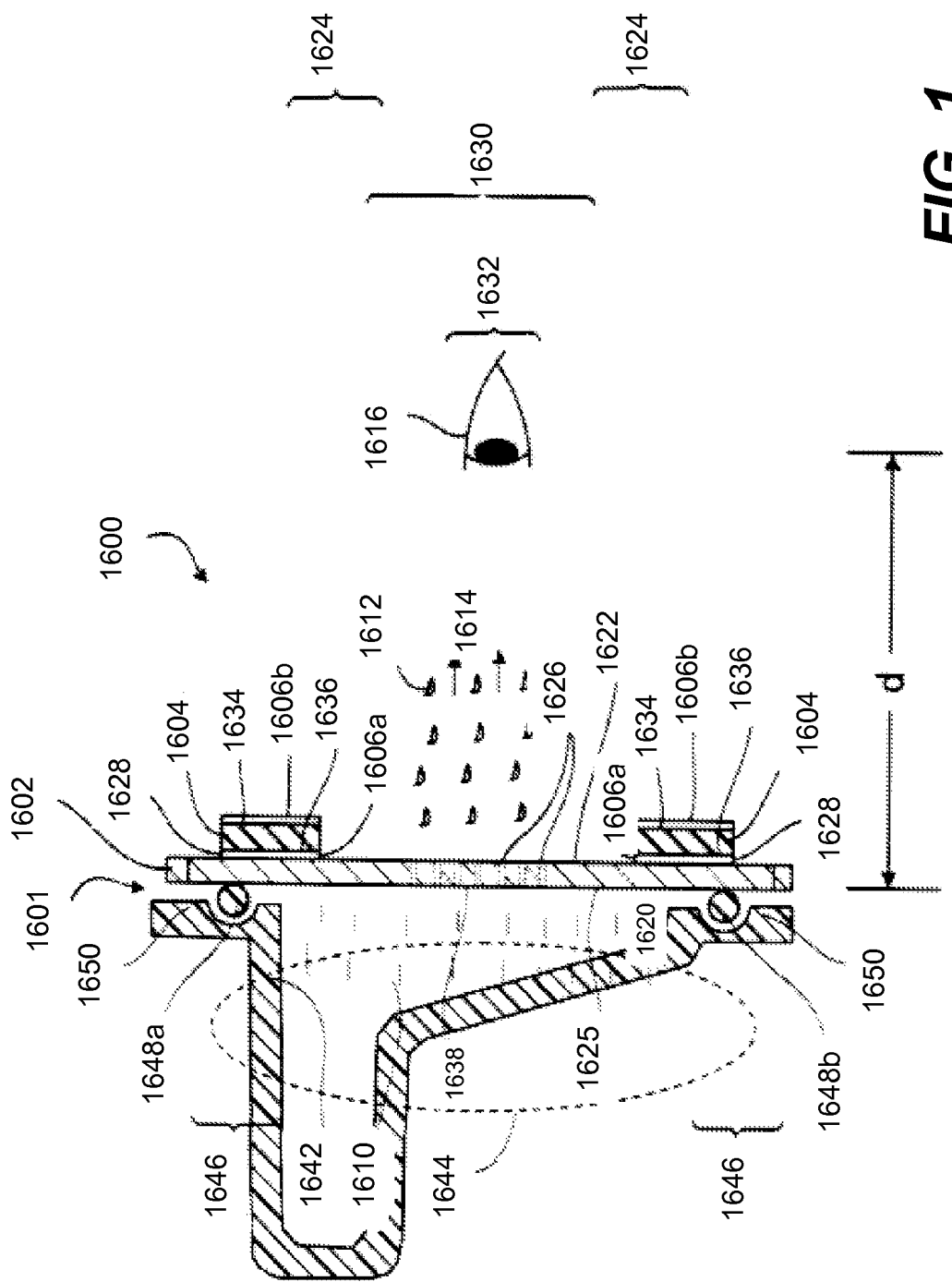
FIG. 1 shows a cross-sectional view of an ejector device according to certain aspects of the disclosure.

The present disclosure relates to ejector mechanisms and devices for generating a directed stream of droplets, as well as improved methods for delivering an ejected stream of droplets to a target. The device and methods may be useful for the delivery of fluid for ophthalmic, topical, oral, nasal, or pulmonary use, more particularly, for use in the delivery of ophthalmic fluid to the eye.

Certain aspects of the disclosure relate to devices and methods for the delivery of a therapeutically effective low dosage volume medicament composition to a target, e.g., by controlling charge, droplet size and/or droplet deposit parameters of the medicament composition. In certain aspects, the ejected stream of droplets may be provided via an ejector device of the present disclosure. However, the disclosure is not so limited and any suitable manner of providing a directed stream of droplets with controllable charge, droplet size and/or droplet deposit parameters may be used. For instance, in certain embodiments, an ophthalmic pipette configured with charging electrodes and grounding surfaces (e.g., a wooden tip), may be used.

In certain other aspects, ejector devices include a charge isolated ejector mechanism, which generates a directed stream of droplets. In certain aspects, devices and methods may provide a controllable charge on the ejected stream of droplets. In yet other aspects, the devices and methods may provide improved delivery and dosing strategies of an ejected stream of droplets to a target. In accordance with the disclosure, delivery targets may include any biological tissue surfaces of interest, e.g., epithelial and mucosal surfaces including oral mucosa, Kiesselbach's Plexus, nasopharynx, oropharynx, larynx, trachea, bronchial tree and alveoli. In addition, the directed stream of droplets can be used to treat the mucosa of the gastrointestinal tract and urogenital tract.

In certain embodiments, devices and methods are provided for the reproducible delivery of therapeutically effective low dosage volume medicament compositions to a desired target (e.g., an eye of a subject in need thereof, as compared to standard eye dropper use and dosage volumes). In certain aspects, therapeutically effective low dosage volumes may be delivered to an eye of, e.g., ¾, ½, ¼, ⅙, ⅛, (e.g., ~0.02-0.75) etc. of the volume of a standard eye dropper volume. By way of example, in certain embodiments, from 0.5 µl-10 µl of medicament composition may be delivered to the eye of a subject, as compared to approximately 25 µl to approximately 70 µl by way of a standard eye dropper, while obtaining equivalent or improved therapeutic efficacy.

In addition, in certain aspects, therapeutically effective low dosage volume medicament compositions comprising lower concentrations of active agents, e.g., as compared to standard eye dropper compositions, may be utilized to deliver a comparable therapeutic dosage of active agent to a subject in need thereof. In this regard, due to the particular controlled delivery methodologies of the present disclosure, therapeutically effective low dosage volume medicament compositions may be delivered to the eye of a subject in a reproducible manner such that the dosage and volume of active agent required for delivery may be reduced, as compared to standard eye droppers. Without intending to be limited by theory, in this way, safety and efficacy may be improved and unwanted side effects may be minimized.

Dosing strategies also may incorporate various approaches to initiating treatment, stopping treatment, switching treatment and responding to different subject states. Examples of dosing modes or strategies include once-a-day dosing, twice-a-day dosing, three times-a-day dosing, continuous dosing, bolus dosing, weekly dosing, monthly dosing, taper dosing, need-based dosing, and feedback dosing by a physician, provider, subject, or family. In addition, dosing schemes may include dosing per eye, as needed. The clinical scenarios where these can be employed include chronic disease, disease exacerbation, need for suppression treatment, need for recurrence treatment, or state of treatment like medicament tolerance.

One embodiment provides a method of delivering a therapeutically effective low dosage volume medicament composition to an eye of a subject in need thereof, as compared to dosage volume of a standard eye dropper, the method comprising: (a) generating a directed stream of droplets of the low dosage volume medicament composition, wherein the droplets have a desired average drop size and average initial ejecting velocity; and (b) delivering a therapeutically effective amount of the droplets of the low dosage volume medicament composition to the eye of the subject, wherein the droplets deliver a desired percentage of the ejected mass of the droplets to the eye. In certain aspects, the directed stream of droplets may be ejected with a controllable charge, to thereby improve delivery of the droplets to the eye.

Devices capable of providing and delivering therapeutically effective low dosage volume medicament compositions to the eye are described herein. By way of example, the directed stream of droplets may be generated via an ejector mechanism, the ejector mechanism comprising a generator plate and a piezoelectric actuator, wherein the generator plate includes a plurality of openings formed through its thickness. The piezoelectric actuator may be operable to directly or indirectly oscillate the generator plate, at a frequency to generate a directed stream of droplets of the low dosage volume medicament composition. In certain aspects, the ejector mechanism may be charge isolated, and may provide a controllable charge to the ejected droplets.

More particularly, the stream of droplets may be generated by devices described herein in a controllable distribution of sizes, each distribution having an average droplet size. In certain embodiments, the average droplet size may be in the range of about 15 microns to about 100 microns, about 20 microns to about 100 microns, greater than 20 microns to about 100 microns, about 20 microns to about 80 microns, about 25 microns to about 75 microns, about 30 microns to about 60 microns, about 35 microns to about 55 microns, etc. However, the average droplet size may be as large as 2500 microns, depending on the intended application. Further, the droplets may have an average initial ejecting velocity of about 0.5 m/s to about 20 m/s, e.g., about 0.5 m/s to about 10 m/s, about 1 m/s to about 10 m/s, about 1 m/s to about 5 m/s, about 1 m/s to about 4 m/s, about 2 m/s, etc. As used herein, the ejecting size and the ejecting initial velocity are the size and velocity of the droplets when the droplets leave the ejector plate. The stream of droplets directed at a target will result in deposition of a percentage of the mass of the droplets including their composition onto the desired location.

In certain aspects of the disclosure, the ejector devices will eject droplets without substantial evaporation, entrainment of air, or deflection off a target surface (e.g., the surface of an eye), which facilitates consistent dosing. Average ejecting droplet size and average initial ejecting velocity are dependent on factors including fluid viscosity, surface tension, ejector plate properties, geometry, and dimensions, as well as operating parameters of the piezoelectric actuator including its drive frequency. In some implementations, about 60% to about 100%, about 65% to about 100%, about 75% to about 100%, about 80% to about 100%, about 85% to about 100%, about 90% to about 100%, about 95% to about 100%, etc., of the ejected mass of droplets are deposited on the surface of the eye, such deposition being repeatable independent of operating and use conditions. The direction of flow of the stream of droplets may be horizontal, or any direction a user chooses to aim the actuation mechanism during use.

Droplet performance is generally related to particle diameter. Without intending to be limited, ejected droplets are slowed to a stop by air drag (i.e., stopping distance of the ejected droplets). Ejected droplets also fall vertically due to gravity. After a short acceleration time, the droplets reach terminal velocity where the drag force equals the force of gravity. The ejected droplets may carry air along with them, which creates an entrained airstream, which aids to then carry the ejected droplets beyond the calculated stopping distance. However, increased levels of entrained air may cause the ejected droplets to flow across an impact surface (e.g., an eye surface) because the entrained airflow must turn 90 degrees at such a surface. Small, ejected droplets (e.g., droplets having an average diameter less than about 17 microns, less than about 15 microns, etc.) are carried along the surface of the eye by the airstream and may not impact the surface. Contrasted to this, larger ejected droplets create less entrained air than an equivalent mass of smaller droplets, and have enough momentum to impact the surface. The ejected droplet stopping distance is a measure of this effect.

Also provided is a method of delivering a therapeutically effective low volume dosage medicament composition to a subject in need thereof, by controlling droplet charge, droplet size and/or deposit parameters of the low dosage volume medicament composition, the method comprising: (a) determining a desired dosage of the low dosage volume medicament composition for the subject in need thereof; (b) generating a directed stream of droplets of the low dosage volume medicament compositions having the desired dosage, wherein the droplets have a desired charge, average drop size, average initial ejecting velocity, or a combination thereof; and (c) delivering a therapeutically effective amount of the droplets of the low dosage volume medicament composition to the eye of the subject in a single application or multiple applications based on the determined desired dosage, wherein the droplets deliver a desired percentage of the ejected mass of the droplets to the eye.

Many factors, including those described herein, can influence the desired dosage. Once the desired dosage is determined, and also if needed, desired frequency, such doses can be delivered. Frequency of dosing can vary by number of times, periodicity or both.

In yet other aspects, the disclosure includes devices and methods for controlling charge on the ejected stream of droplets to thereby improve delivery of the fluid to a target. In this regard, the methods comprise providing an ejected stream of droplets via an ejector device configured to controllably charge ejected droplets, thereby improving delivery of the ejected droplets to a desired site of administration.

By way of example and without intended to be limited, a controllable charge on ejected droplets may improve administration of the ejected droplet stream to a target delivery site by increasing the adherence, distribution, residence time, absorption, transportation, biotransformation and/or bioavailability of the ejected droplets upon administration to a desired surface. More particularly, controlled droplet charge may improve delivery of ejected droplets due, at least in part, to interactions between the droplet change and the charged properties of the surface of administration, e.g., the surface of the eye, oral mucosa, lungs, or other tissue of interest. For instance, positively charged droplets spread onto and pass through the net negatively charged surface of the eye, e.g., thereby enhancing bioavailability of medicaments comprised in the droplets.

Ejector devices and ejector mechanisms are disclosed, which controllably charge ejected droplets and/or control droplet size and droplet deposit parameters, to thereby improve delivery of the ejected droplets to a desired site of administration. However, the disclosure is not so limited and any suitable manner of providing a directed stream of droplets having controllable charge, droplet diameter, and/or droplet deposit parameters, may be used. By way of example, piezoelectric actuated ejector devices configured to controllably charge ejected droplets via induced charging and/or tribocharging may be used.

For instance, in certain aspects, an ejector device or ejector mechanism of the disclosure may charge ejected droplets via induction. Such devices and ejector mechanisms may be configured to generate an electric field that causes a controllable charge, positive or negative, on an ejected fluid. In certain configurations, the droplet fluid is not charged or exposed to an electric field other than during ejection (e.g., prior to ejection). The droplet fluid is only charged, controllably and repeatedly, during ejection to a desired site of administration.

In certain embodiments, the methods described herein may be used to treat, ameliorate, or prevent various eye diseases, conditions, discomforts, infections, and disorders in a subject in need thereof, including but not limited to glaucoma. Medicament compositions include, without limitation, any suitable composition for use in connection with administration to the eye of a subject, which composition, e.g., may be a suspension or emulsion and may have any suitable viscosity in a range capable of droplet formation using an ejector mechanism of the disclosure. As explained in further detail herein, in accordance with certain aspects of the present disclosure, the ejector mechanism of an ejector device may form a directed stream of droplets, which may be directed toward a target.

In this regard, any suitable medicament showing a desired ophthalmic activity may be administered. In an aspect, the medicament is available by prescription. In another aspect, the medicament is available over the counter. In an aspect, the medicament is or comprises a biologic agent. In an aspect, the biologic agent is selected from the group consisting of a full-length antibody, an active fragment of a full-length antibody, a peptide, a pegylated peptide, and an enzymatic ingredient. In another aspect, the biologic ingredient is selected from the group consisting of bevacizumab, ranibizumab, FV fragments, bi-specific antibodies, fusion molecules, pegaptanib, plasmin, and microplasmin. In a further aspect, the biologic agent is selected from the group consisting of ranibizumab antibody FAB (including Lucentis™), VEGF Trap fusion molecule (including VEGF Trap-Eye™), microplasmin enzyme (including Ocriplasmin™), macugen pegylated polypeptide (including Pegaptanib™), and bevacizumab (including Avastin™).

In another aspect, a medicament to be administered is or comprises a small molecule. For instance, the medicament to be administered may comprise cyclosporine, neomycin, biomonidine, and aminoglycoside antibiotics, including for example, tobramycin, gentamycin, and latanoprost.

In an aspect, the medicament to be delivered comprises a medicament selected from the group consisting of carboxymethylcellulose sodium, tetrahydrozoline HCl, pheniramine maleate, ketotifen fumarate, oxymetazoline HCl, naphazoline HCl, pheniramine maleate, moxifloxacin hydrochloride, bromfenac, proparacaine hydrochloride, difluprednate, gatifloxacin, travoprost, bepotastine besilate, gatifloxacin, loteprednol etabonate, timolol ophthalmic, olopatadine hydrochloride, phenylephrine hydrochloride, levofloxacin, ketorolac tromethamine, latanoprost, bimatoprost, and BAK-free latanoprost. In another aspect, the medicament is selected from the group consisting of Refresh Tears™, Visine Advanced Relief™, Naphcon A™, Sensitive Eyes™, Renu™, Opti-free™ rewetting drops, Visine A.C.™, Hypo Tears™, Alaway™, Visine L.R.™, Visine original, Rohto Cool™, Soothe XP™, Zaditor™, Bausch & Lomb Advanced Eye Relief Redness™, Visine A™, Opcon-A™, Walgreens artificial tears, Visine™ dry eye relief, Advanced Eye Relief Dry Eye™, Opti-free Replenish™, Clear Eyes™ redness relief, Vigamox™, Bromday™, Durezol™, Zymaxid™, Travatan Z™, Tropicamide™, Bepreve™, Zymar™, Lotemax™, Istalol™, Pataday™, AK-Dilate™, Toradol™, Xalatan™, and Lumigan™.

In another aspect, the medicament to be delivered comprises a medicament selected from the group consisting of fluorosilicone acrylate, sodium carboxymethylcellulose, hydroxypropyl methylcellulose, tetrahydrozoline HCl, carboxymethylcellulose sodium, propylene glycol, hypromellose, zinc sulfate, dorzolamide HCl timolol maleate, azithromycin, brimonidine tartrate, nepafenac, brinzolamide, besifloxacin, dorzolamide HCl, prenisone acetate, loteprednol etabonate, tobramycin/dexamethasone, and cyclosporine. In a further aspect, the medicament is selected from the group consisting of Tears Naturale II™, Optimum NWN™, Thera Tears™, Systane Ultra™, GenTeal™, Systane Lubricant Eye Drops™, Blink™ tears, Visine Max Redness Relief™, Refresh Optive™, Muro128™, Systane Balance™, Rohto Hydra™, Rohto Ice™, Walgreens sterile artificial tears, Rohto Arctic™, Clear Eyes™ natural tears lubricant, Similasan™ pink eye relief, Similasan™ allergy eye relief, Cosopt™, AzaSite™, Alphagan P™, Nevanac™, Azopt™, Besivance™, Trusopt™, Alrex™, and Restasis™.

In an aspect, an ophthalmic medicament to be delivered is used to treat glaucoma. In an aspect, a glaucoma medicament is selected from the group consisting of travoprost, timolol ophthalmic, latanoprost, bimatoprost, dorzolamide HCl timolol maleate, brimonidine tartrate, brinzolamide, dorzolamide HCl, and BAK-free latanoprost. In a further aspect, a medicament is selected from the group consisting of travoprost, timolol ophthalmic, latanoprost, bimatoprost, and BAK-free latanoprost. In another aspect, a medicament is selected from the group consisting of dorzolamide HCl timolol maleate, brimonidine tartrate, brinzolamide, and dorzolamide HCl. In an aspect, a glaucoma medicament is selected from the group consisting of Travatan™, Istalol™, Xalatan™, Lumigan™, Cosopt™, Alphagan P™, Azopt™, and Trusopt™. In another aspect, a medicament is selected from the group consisting of Travatan™, Istolol™, Xalatan™, and Lumigan™. In a further aspect, a medicament is selected from the group consisting of Cosopt™, Alphagan P™, Azopt™, and Dorzolamide HCl™.

The term "therapeutically effective" amount refers to an amount of an active agent used to treat, ameliorate, prevent, or eliminate the identified ophthalmic condition (e.g., disease or disorder), or to exhibit a detectable therapeutic or preventive effect. The effect can be detected by, for example, chemical markers, antigen levels, or time to a measurable event, such as morbidity or mortality. The precise effective amount for a subject will depend upon the subject's body weight, size, and health; the nature and extent of the condition; and the therapeutic or combination of therapeutics selected for administration. Effective amounts for a given situation can be determined by routine experimentation that is within the skill and judgment of the clinician. Any of the agents can be provided in an effective amount.

For any active agent, the effective amount can be estimated initially either in cell culture assays, e.g., in animal models, such as rat or mouse models. An animal model may also be used to determine the appropriate concentration range and route of administration. Such information can then be used to determine useful doses and routes for administration in humans.

In an aspect, the concentration of an active ingredient in a medicament is measured as a percentage of the active ingredient in solution. In an aspect, the concentration of active ingredient ranges from about 0.0001% to about 5%. In another aspect, the concentration of active ingredient in a medicament ranges from about 0.0005% to about 1%. In other aspects, the concentration of active ingredient ranges from about 0.0005% to about 0.0001%, from about 0.0001% to about 0.001%, or from about 0.0005% to about 0.001%. In other aspects, the concentration of active ingredient ranges from about 0.005% to about 0.001% or from about 0.001% to about 0.01%. In another aspect, the concentration of active ingredient ranges from about 0.001% to about 0.5%. In various other aspects, the concentration of active ingredient is selected from the group consisting of about 0.0001%, about 0.0005%, about 0.001%, about 0.0025%, about 0.005%, about 0.01%, about 0.025%, about 0.05%, about 0.1%, about 0.2%, about 0.3%, about 0.4%, about 0.5%, about 0.75%, about 1%, about 1.5%, about 2%, about 2.5%, about 3%, about 4%, and about 5% measured as a percentage of the solution. However, given the lower dosing amounts afforded by the methods of the present disclosure, higher concentrations may be used depending on the intended use. For example, about 10%, about 20%, about 25%, of the active ingredient in the medicament, measured as a percentage of the solution, may be utilized.

In other aspects, the disclosure generally relates to ejector devices useful, e.g., in the delivery of a directed stream of droplets for ophthalmic, topical, oral, nasal, or pulmonary use, more particularly, for use in the delivery of ophthalmic fluid to the eye. Droplets may be formed by an ejector mechanism from fluid contained in a reservoir coupled to the ejector mechanism. Except as otherwise described herein, the ejector mechanism and reservoir may be disposable or reusable, and the components may be packaged in a housing of an ejector device. More particularly, exemplary ejector devices and ejector mechanisms are illustrated in U.S. Application No. 61/722,589, filed Nov. 5, 2012, entitled Charge Isolated Ejector Mechanisms, Ejector Devices, and Methods of Use; U.S. application Ser. No. 13/712,784, filed Dec. 12, 2012, entitled "Ejector Mechanism, Ejector Device, and Methods of Use," and U.S. application Ser. No. 13/712,857, filed Dec. 12, 2012, entitled "High Modulus Polymeric Ejector Mechanism, Ejector Device, And Methods of Use," each of which are herein incorporated by reference in their entirety.

For example, referring to FIG. 1, ejector assembly 1600 may include an ejector mechanism 1601 and reservoir 1620. Ejector mechanism 1601 may include an oscillating plate assembly or hybrid mechanism with ejector plate 1602 coupled to generator plate 1632 including one or more openings 1626, which can be activated by (e.g. piezoelectric) actuator 1604. Actuator 1604 vibrates or otherwise displaces ejector plate 1602 to deliver fluid 1610 from reservoir 1620, as droplets 1612 from one or more openings 1626 to form a stream of droplets ejected from one or more openings 1626, along direction 1614.

In some applications, ophthalmic fluid may be ejected toward eye 1616, for example in a human adult or child, or an animal. The fluid may contain a pharmaceutical agent to treat a discomfort, condition, or disease of the human or an animal, either in the eye or on skin surface, or in a nasal or pulmonary application.

The attachment of ejector 1604 to ejector plate 1602 may also affect operation of ejection assembly 1600, and the creation of single droplets or streams thereof. In the implementation of FIG. 1, for example, ejector 1604 (or a number of individual ejector components 1604) may be coupled to a peripheral region of ejector plate 1602, on surface 1622 opposite reservoir 1620.

Central region 1630 of ejector plate 1602 includes ejection region 1632 with one or more openings 1626, through which fluid 1610 passes to form droplets 1612. Ejection region (or droplet generator) 1632 may occupy a portion of central region 1630, for example the center, or the ejection hole pattern of ejector region 1632 may occupy substantially the entire area of central region 1630. Further, open region 1638 of reservoir housing 1608 may correspond substantially to the size of ejection region 1632, or open region 1638 may be larger than ejection region 1632.

As shown in FIG. 1, ejector plate 1602 is disposed over or in fluid communication with reservoir 1620, containing fluid 1610. For example, reservoir housing 1608 can be coupled to ejector plate 1602 at a peripheral region 1646 of the first major surface 1625, using a suitable seal or coupling such as O-rings 1648a to seal against reservoir wall 1650. A portion 1644 of reservoir housing 1608 may also be provided in the form of a collapsible bladder. However, the disclosure is not so limited, and any suitable bladder or reservoir may be used.

Prior to excitation, droplet generation device (or ejection mechanism) 1600 is configured in a resting state. When a voltage is applied across electrodes 1606a and 1606b on opposite surfaces 1634 and 1636 of (e.g., piezoelectric) actuator 1604, ejector plate 1602 deflects to change between relatively more concave shape 1700 and relatively more convex shape 1701, as shown in FIGS. 2A and 2B, respectively.

When driven with an alternating voltage, actuator 1604 operates to reverse the convex and concave shapes 1700 and 1701 of ejector plate 1602, inducing periodic movement (oscillation) of ejector plate 1602 in ejection region (droplet generator) 1632. Droplets 1612 are formed at apertures or openings 1626, as described above, with the oscillatory motion of ejection region 1632 causing one or more droplets 1612 to be ejected along fluid delivery (ejection) direction 1614, for example in a single-droplet (droplet on demand) application, or as a stream of droplets.

The drive voltage and frequency may be selected for improved performance of the ejection mechanism, as described above. In particular aspects, the oscillation frequency of actuator 1604 may be selected at or near a resonance frequency of ejector plate 1602, or at one or more frequencies selected to oscillate ejector plate 1602 at such a resonance via superposition, interference, or resonant coupling.

When operated at or near a resonant frequency (for example, within the full width at half maximum of a resonance), ejector plate 1602 may amplify the displacement of ejector region (droplet generator) 1632, decreasing the relative power requirements of the actuator, as compared to a direct-coupling design. The damping factor of the resonance system, including ejector plate 1602 and droplet generator 1632, may also be selected to be greater than the piezoelectric actuator input power, in order to reduce fatigue and increase service life without substantial failure.

Exemplary hybrid ejector mechanisms are disclosed in U.S. application Ser. No. 13/712,784, filed Dec. 12, 2012, entitled "Ejector Mechanism, Ejector Device, and Methods of Use," and U.S. application Ser. No. 13/712,857, filed Dec.

Figure 3A:
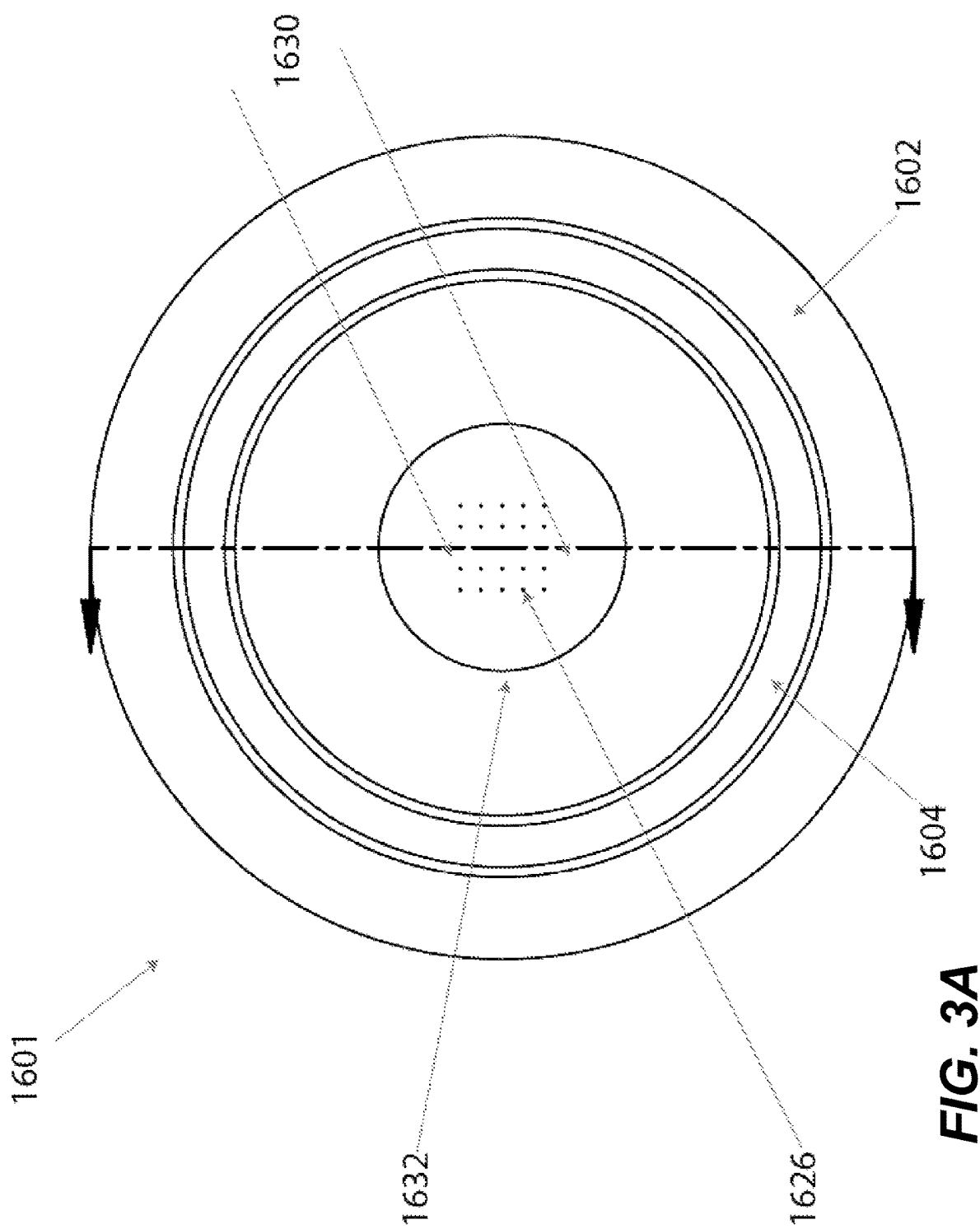
FIG. 3A is a schematic view of an ejector mechanism according to certain aspects of the disclosure.

12, 2012, entitled "High Modulus Polymeric Ejector Mechanism, Ejector Device, And Methods of Use," which are incorporated by reference herein. In one particular embodiment, ejector plate mechanism 1601 may include a rotationally symmetric ejector plate 1602 coupled to a generator plate-type actuator 1604, for example as shown in FIG. 3A. However, the disclosure is not so limited. In the particular configuration of FIG. 3A, generator plate-type actuator 1604 incorporates one or more individual piezoelectric devices or other actuator elements, as described above, for driving rotationally symmetric ejector plate 1602. Drop generator (ejector) region 1632 of ejector plate 1602 includes or is formed by a pattern of openings 1626 in center region 1630, and is driven using a suitable drive signal generator circuit as described below. Exemplary techniques for generating drive voltages are illustrated in U.S. Provisional Patent Application No. 61/647,359, "Methods, Drivers and Circuits for Ejector Devices and Systems," filed May 15, 2012, as incorporated by reference herein.

Figure 3B:
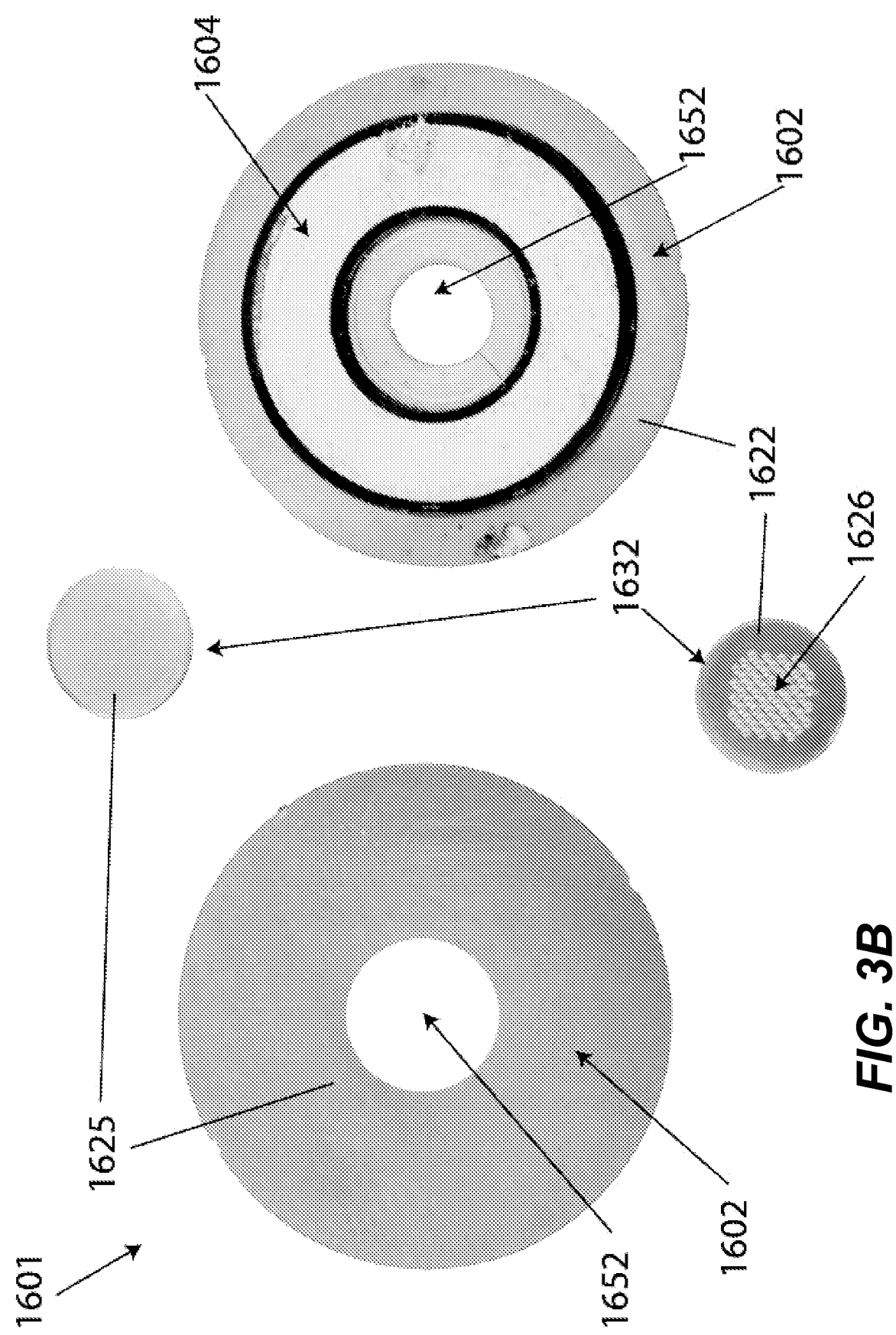
FIG. 3B is a disassembled view of an ejector mechanism according to certain aspects of the disclosure.

FIG. 3B is a disassembled view of symmetric ejector mechanism 1601. In this embodiment, ejector plate 1602 utilizes a discrete (separate) drop generator element (ejector region) 1632, as shown on the left and right of FIG. 5B from back (face down) surface 1625 and front (face up) surface 1622, respectively. Drop generator element 1632 is mechanically coupled to ejector plate 1602 in central aperture 1652, and includes a pattern of openings 1626 configured to generate a stream of fluid droplets when driven by generator-plate type actuator 1604, as described above.

Figure 3C:
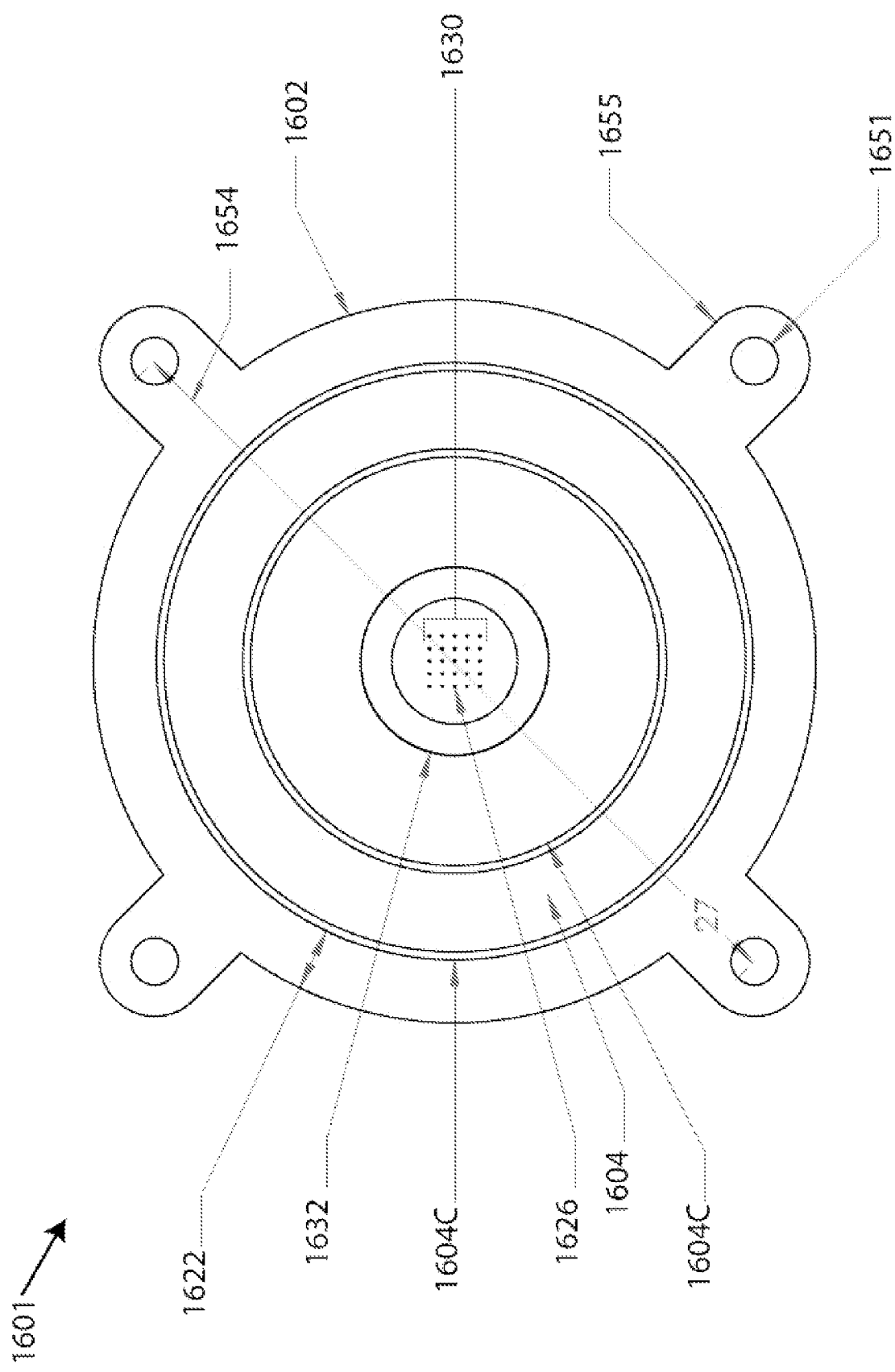
FIG. 3C is a plan view of an ejector mechanism according to certain aspects of the disclosure.

FIG. 3C is a plan view of symmetric ejector mechanism 1601. Ejector mechanism 1601 includes ejector plate 1602 with mechanical couplings 1604C to generator plate-type actuator 1604 and droplet generator 1632 with a pattern of openings 1626 in central region 1630, as described above. Ejector mechanism 1601 may be coupled to a fluid reservoir or other ejection device component via apertures 1651 in tab-type mechanical coupling elements 1655, or using another suitable connection as described above with respect to FIG. 3.

As shown in FIG. 3C, ejector mechanism 1601 and ejector plate 1602 may be defined by overall dimension 1654, for example about 21 mm, or in a range of about 10 mm or less to about 25 mm or more, depending upon application. Suitable materials for ejector plate 1602 and drop generator 1632 include, but are not limited to, flexible stress and fatigue-resistant metals such as stainless steel.

For orientation purposes, the different elements of ejector mechanism 1601 as shown in FIGS. 3A-3C may be described relative to the location of fluid 1610 or reservoir 1620, as described above with respect to FIG. 1. In general, the proximal elements of mechanism 1601 are located closer to fluid reservoir 1620 and the distal elements are located farther from fluid reservoir 1620, as defined along the droplet stream or ejection direction 1614.

In certain aspects, the ejector devices include a piezoelectric ejector mechanism configured to generate an electric field that causes a controllable charge, positive or negative, on a fluid to be ejected as a directed stream of droplets. In various embodiments, the ejector devices include an ejector assembly including a charge isolated ejector mechanism configured to generate a controllable stream of droplets of fluid with a controllable charge.

When a piezoelectric element has an electric field applied to it with alternating polarity, periodic movement of the element occurs. In certain configurations, applying an electric field to a piezoelectric device may be accomplished by connecting two different voltages, or potentials, to the two electrodes of the device. In certain instances, voltages over 60 volts may be necessary to adequately drive piezoelectric devices. In battery powered systems, high output voltages are difficult to create due to input voltage and voltage converter limitations. It can be difficult to drive many piezoelectric battery powered systems in a single ended configuration. (i.e., configurations having only one electrode driven by an electrical signal, with the other being grounded).

Differential signaling increases the effective voltage swing from a single supply, and may be used to overcome battery limitations on the electric field that can be applied to the piezoelectric (i.e., equal amplitude and opposite polarity electrical signals are applied to each electrode of the piezoelectric). However, differential signaling is not without consequence in a device configured to eject a directed stream of droplets, in that fluid in direct contact with a differentially driven surface can charge and discharge with time. For instance, if the surface potential oscillates in time, the fluid will charge and discharge. Electromotive forces can also pull generated droplets towards the alternating potential surface upon ejection, thereby reducing system ejection performance and resulting in fluid deposition on the ejection surface. Electro-wetting can also occur in electrolytic fluids, pulling fluid out of ejector holes and flooding the ejector surface.

In certain embodiments, the droplet ejector device may be a piezoelectric actuated droplet ejector device including a droplet ejector plate, wherein the potentials from driving the piezoelectric are completely isolated from the droplet ejector plate. In this regard, the ejector mechanism may be a charge isolated ejector mechanism that is configured so as to allow differential signaling, e.g., for portable, battery powered devices, while maintaining a grounded ejector surface. In general, the piezoelectric element is bounded on one side by metallization and the other side a conducting ring. The conducting ring is electrically isolated from the grounded ejector plate by a thin dielectric washer. This system provides two separate terminals for electrically driving the piezoelectric element, while still electrically grounding the ejector plate. In certain embodiments, the grounded ejector plate may itself comprise openings for generation of droplets of fluid, or it may be coupled to a generator plate which comprises openings, etc.

Except as otherwise described herein, exemplary device configurations may include charge isolated ejector mechanisms. Charge isolation, as well as prevention of electro-wetting, may be maintained with any static potential on the isolated charge ejector plate. In certain aspects, the potential, whether it is ground, a positive voltage, or negative voltage, will preferably be static, i.e., not change, during ejection. In this regard, the ejector plate may be insulator or conductor. However, if the ejector plate is an insulator, an electrode must be in contact with the plate at some point to provide static potential.

In one embodiment, the charge isolated ejector surface comprising a generator plate may have a proximal surface in contact with a fluid, and the generator plate may have one or more openings. In an aspect, the ejector surface may be in contact with a dielectric layer, separating the ejector surface from a conducting layer. In an aspect, the conducting layer may separate the dielectric layer from a piezoelectric actuator that is operable to oscillate upon application of a voltage.

In other aspects, ejector device configurations and mechanisms for applying a controllable electric field to ejecting fluid droplets upon administration are disclosed. In these configurations, the fluid is not charged or exposed to an electric field prior to administration. The fluid is only charged during ejection, to a controllable and repeatable charge, positive or negative, that is beneficial for deposition, drug transport, and bioavailability at the target site of administration. In certain embodiments, such ejector device configuration may include a charge isolated ejector mechanism, as described herein.

In certain aspects, when a droplet is ejected in accordance with the disclosure, the electric field causes charges in the fluid to separate so as to align with the field. As the static potential surface is kept at a set potential via an electrical source or ground, charge in contact with the ejector plate is stripped and drained by the supply/ground as the droplet leaves the ejector plate. The droplet retains a net electrical charge, which is positive if the ejector surface is at the higher potential and negative if the ejector surface is at a lower potential than the reference electrode. This process is shown in FIG. 4A-4B, with exemplary potentials and an inductive charging based ejection system. In this configuration, the fluid is not charged until the instant the droplet leaves the ejector plate. By moving the reference surface closer, the strength of the charging may be increased. The difference in potentials between the reference and the ejector plate can also be increased to increase the electric field. The charge deposited on each droplet is repeatable and is generally linear with applied field. Static potentials can be applied all the time or just during ejection.

More particularly, in certain embodiments, FIGS. 4A and 4B illustrate inductive charging of a droplet. FIG. 4A shows exemplary electrical signals, demonstrating piezoelectric drive signals which alternate between the maximum output voltage and ground. The ejector plate may be at any defined potential between the maximum output voltage and the negative of the maximum output voltage. FIG. 4B shows the E-field lines between an ejector plate and ground. As the droplet leaves the charged ejector plate, the charge in the liquid redistributes in the field and is stripped by the constant potential surface, leaving a charged droplet upon ejection.

Other embodiments of the disclosure may impart charge via tribocharging. Tribocharging is a known phenomenon where charge is stripped from a surface through friction as a material rubs against it at a certain velocity. Tribocharging is conventionally thought to be random, but this is only the case if potential of the ejecting surface remains floating (no defined potential from electrical source or ground). This is shown in FIG. 4C, where a droplet strips charge from the material, but as there is no electrical source or ground to drain off the charge imbalance. In this configuration, droplets are randomly charged positively or negatively in order to balance the charge on the ejector surface.

Contrasted to this, and in accordance with certain aspects of the disclosure, by controlling the potential of the ejector surface and equalizing the charge of the ejector surface between each droplet ejection, the tribocharge can be made always positive or always negative, relative to the system potential. Furthermore, by controlling the velocity of the droplet ejection, the amount of charge imparted to each droplet can be controlled. More particularly, with reference to FIG. 4C-4D, ejector mechanisms are illustrated wherein (C) the ejector surface charge is floating, i.e. has no defined potential, thus with each ejection, charge is randomly stripped from droplet or ejector surface to equalize charge on the ejector surface and, (D) the ejector surface is grounded to drain negative charge off, thus allowing charge stripping due to friction to maintain the same sign and magnitude with each ejection. A charge isolated ejector mechanism of the disclosure may be used to control tribocharging in this manner.

Figure 5:
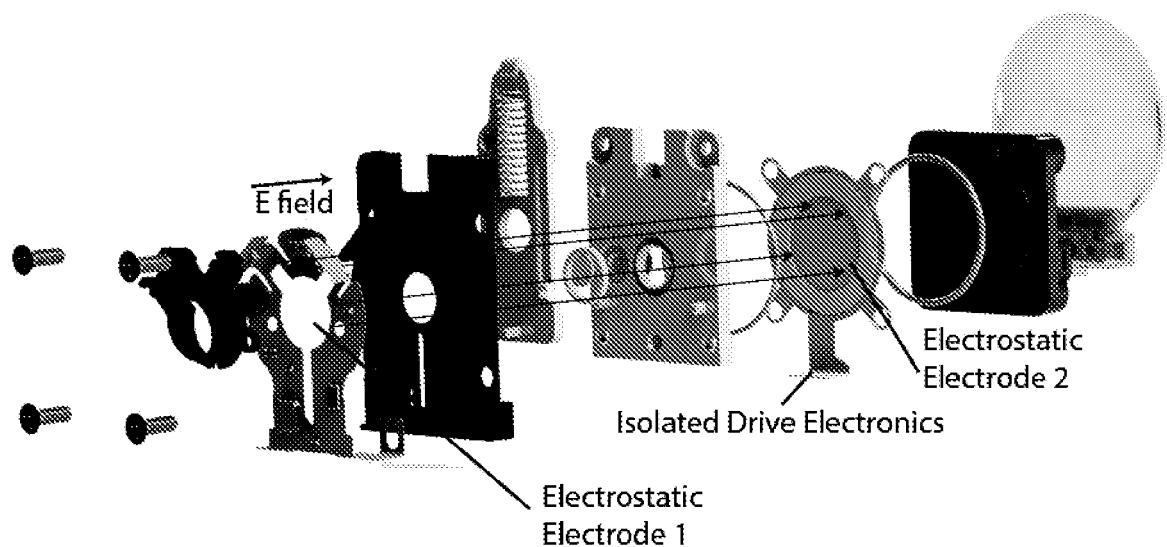
FIG. 5 shows a three-dimensional expanded view of a charge isolated ejector mechanism according to certain aspects of the disclosure.
Figure 6:
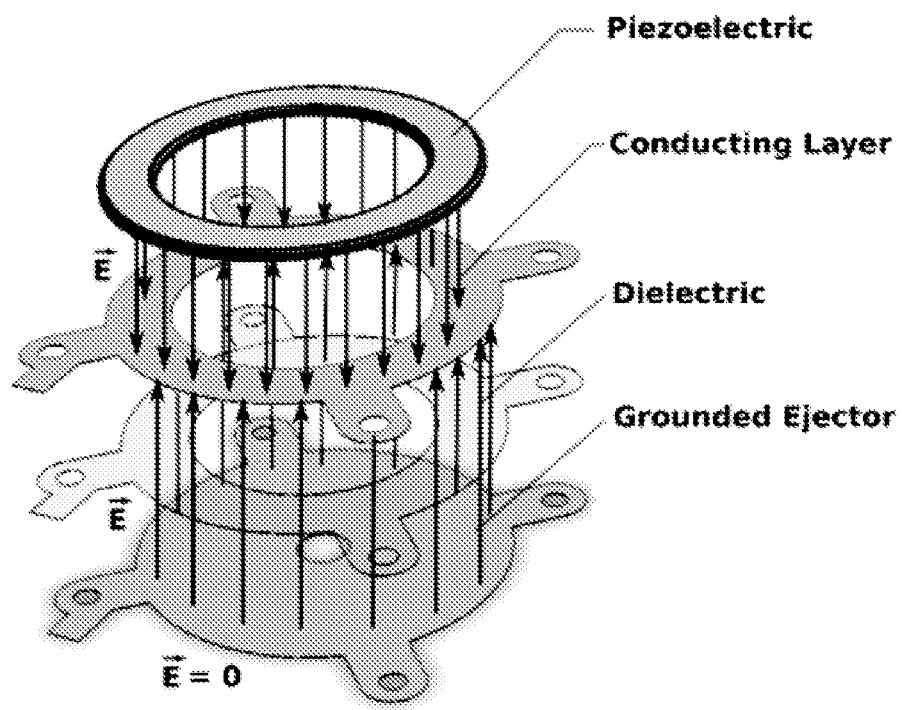
FIG. 6 shows a three-dimensional expanded view of a differential signal compatible, grounded ejector surface, droplet ejector mechanism having a charge isolated design according to certain aspects of the disclosure.

An exemplary charge isolated ejector mechanism capable of providing a controllable charge is shown in FIG. 5. In the embodiment shown, a ground layer forms the external reference potential. The ejector mechanism includes isolated electrodes for the piezoelectric drive signals and an electrode in contact with the ejector plate for static potential control. A positive potential on the ejector plate will result in a positive charge in this embodiment, while a negative potential will result in a negative charge.

As illustrated, the ejector plate may be isolated from the AC drive potentials and a static potential can be placed on the ejector plate. In certain embodiments, an external electrode can be placed in close proximity to the ejector plate with a different reference potential, and a constant voltage may be supplied to the ejector plate. An electric field may then be developed between the two surfaces. The polarity of the field is determined by which surface has the larger potential. The magnitude of the field is determined by the difference in voltages between the surfaces and their separation in the relationship $E=V/d$ for parallel surfaces. As the fluid to be ejected is only in contact with one charged surface and completely contained by insulators, the fluid will not conduct current itself. During ejection, the drug accelerates due to mechanical motion and experiences an electric field, $E=V/d$, at the instant it passes the plane of the ejection plate. Charge redistributes to align with the electric field, and due to the ejection velocity, the polarity charge of electrostatic electrode 1 is stripped from the fluid and drained off by electrostatic electrode 2. The fluid is then ejected as droplets, retaining the desired charge in transit.

In certain embodiments, a retainer flex circuit ground layer may form the reference potential with the surface of the ejector plate. A static voltage is applied to the ejector plate, resulting in a charge being applied to the droplets as they are ejected but not while the fluid is in storage. The charge can be varied linearly by changing the surface potential in this configuration. Additionally, zero charge can be imparted to the fluid during ejection by keeping the ejector surface grounded. The ejector surface can be electrically insulating or conductive. Electrically insulating layers require an electrode connection and cannot be left floating (electrically). Plastic parts between the retainer flex and ejector surface do not significantly affect charging.

With reference to FIG. 6, an ejector mechanism 1601 may comprise a distal piezoelectric actuator 1604, separated from a proximal ejector plate 1602 first by a conducting layer 1660 and then by a dielectric layer 1662. In an aspect, the distal side of piezoelectric actuator 1604 is bounded on one side by metallization and on the proximal side by a conducting layer 1660. In an aspect, distal side of the dielectric layer 1662 is located proximal to the conducting layer 1660 and dielectric layer 1662 both separates and charge isolates ejector plate 1602. The proximal side of ejector plate 1602 contacts the fluid 1610 and is in fluid communication with the reservoir 1620. The distal side of ejector plate 1602 is in contact with the proximal side of dielectric layer 1662. In an aspect, the ejector plate 1602 may be grounded and electrically isolated from the conducting layer 1660 by the dielectric layer 1662. In an aspect, ejector mechanism 1601 provides two separate terminals for electrically driving the piezoelectric, electrode 1606*a* on surface 1634 (e.g., distal surface) and electrode 1606*b* on surface 1636 (e.g., proximal surface). In an aspect, dielectric layer 1662 separating conducting layer 1662 provides for a charge isolated ejector plate 1602. In a further aspect, the charge isolated ejector plate 1602 may be grounded.

In an aspect according the present disclosure the dielectric layer 1662 may comprise a plastic, glass, porcelain, etc. The dielectric layer may be any suitable size and shape to accommodate the piezoelectric element and ejector surface (exemplary dimensions are shown in FIG. 8), but the disclosure is not so limited), but not so as to impede droplet generation and ejection. In certain aspects, the dielectric layer may range in thickness from 10 μm to 30 μm, 12 μm to 25 μm, 15 μm to 25 μm, etc. In preferred configurations, the dielectric layer is concentric in shape with the piezoelectric element and/or ejector surface, and its thickness is minimized to reduce stiffness of the charge isolated ejector mechanism.

In an aspect, the dielectric layer may be a plastic selected from polystyrene, polyvinyl chloride, or nylon. In an aspect, the dielectric layer may be selected from the group consisting of polyester (PES), polyethylene terephthalate (PET), polyethylene (PE), high-density polyethylene (HDPE), polyvinyl chloride (PVC), polyvinylidene chloride (PVDC), low-density polyethylene (LDPE), polypropylene (PP), polystyrene (PS), pigh impact polystyrene (HIPS), polyamides (PA) (e.g., nylon), acrylonitrile butadiene styrene (ABS), polycarbonate (PC), polycarbonate/acrylonitrile butadiene styrene (PC/ABS), polyurethanes (PU), melamine formaldehyde (MF), plastarch material, phenolics (PF), polyetheretherketone (PEEK), polyetherimide (PEI) (Ultem), polylactic acid (PLA), polymethyl methacrylate (PMMA), polytetrafluoroethylene (PTFE), or urea-formaldehyde (UF).

In an aspect according the present disclosure the conducting layer 1660 may comprise a metal, graphite, or a polymer. The conducting layer may be any suitable size and shape to accommodate the piezoelectric element and ejector surface, but the disclosure is not so limited), but not so as to impede droplet generation and ejection. In certain aspects, the conducting layer may range in thickness from 10 μm to 30 μm, 12 μm to 25 μm, 15 μm to 25 μm, etc. In preferred configurations, the conducting layer is concentric in shape with the piezoelectric element and/or ejector surface, and its thickness is minimized to reduce stiffness of the charge isolated ejector mechanism.

In an aspect the conducting layer 1660 may be copper, aluminum, silver, or gold. In an aspect, the polymer may be a melanin. In another aspect, the polymer may be a poly(fluorene), a polyphenylene, a polypyrene, a polyazulene, a polynaphthalene, a poly(pyrrole) (PPY), a polycarbazole, a polyindole, polyazepine, a polyaniline (PANI), a poly(thiophene) (PT), a poly(3,4-ethylenedioxythiophene) (PEDOT), a poly(p-phenylene sulfide) (PPS), a poly(acetylene) (PAC), or a poly(p-phenylene vinylene) (PPV).

In aspects of the disclosure, at least one or more layers of the charge isolated ejector mechanism may be configured as a flexible printed circuit (FPC), e.g., two signal layers and a ground layer. Operation of the ejection mechanism may generally be impacted by stiffness of the materials of construction. Stiffness is generally impacted by the use of adhesives, their rigidity, and their thickness. As such, in certain aspects, construction and configuration of the charge isolated ejector mechanism optimized to improve performance in this regard. In certain embodiments, the FPC layers may then be coupled to the remaining layers of the charge isolated ejector mechanism, e.g., an ejector surface, piezoelectric element, etc.

The layers of the charge isolated ejector mechanism configured as a FPC can be designed and fabricated in any suitable manner. In certain aspects, the FPC may be configured so as minimize its thickness. In this regard, adhesiveless construction may be preferred, but the disclosure is not so limited. In certain embodiments, the FPC layers may comprise the dielectric layer and the conducting layer of the charge isolated ejector mechanism, as well as bonding layers (e.g., adhesiveless bonding layers), flying lead connections, etc. to aid in fabrication and assembly, as explained in further detail herein.

Figure 7A:
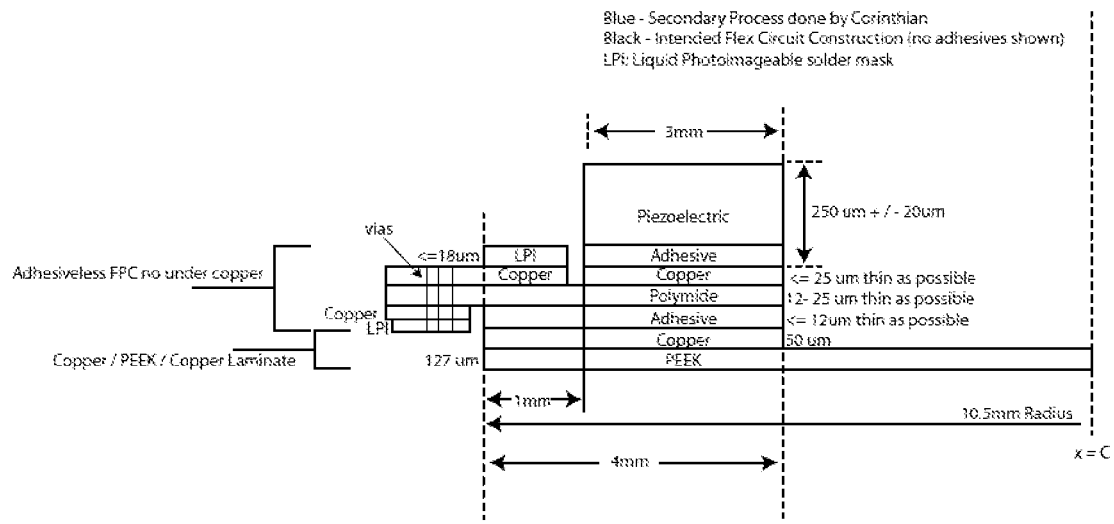
FIG. 7A-7B shows a cross section of FPC bonded to copper/PEEK/copper ejector surfaces for (A) no under copper design and (B) under copper design according to certain aspects of the disclosure.
Figure 7B:
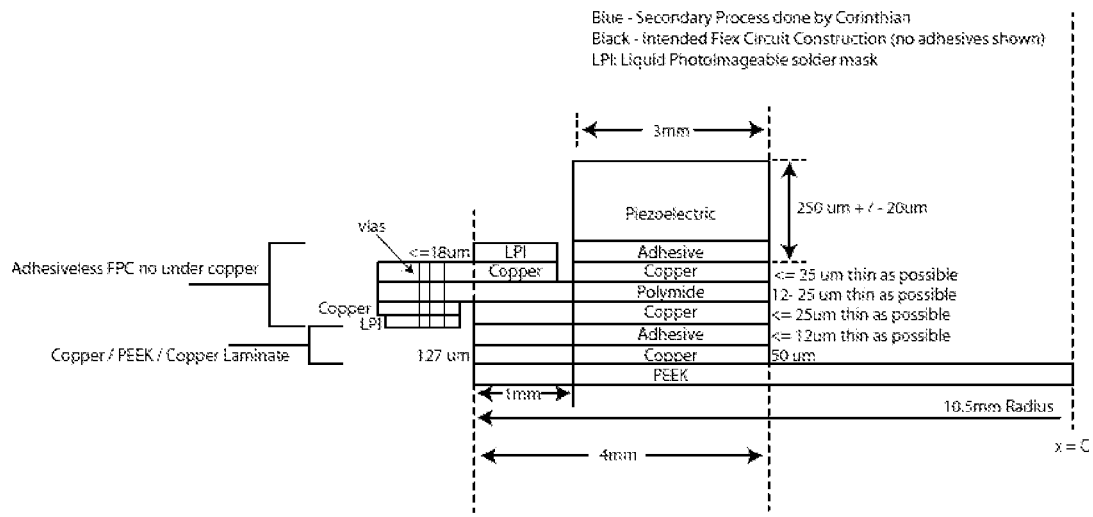

With reference to FIGS. 7A-7B, exemplary conducting layer/dielectric layer designs are shown. As shown in FIGS. 7A-7B, the core of the circuit is built from dual copper clad polyimide laminate (adhesiveless). The polyimide may be punched or drilled out, along with any copper under it. A photoresist coating may be applied and imaged to allow patterning of the copper on both sides. Finally, an LPI (liquid photo-imageable) soldermask or polyimide cover coating may be applied to provide electrical protection of the top copper and bottom. In certain embodiments, the LPI may be selected from a crosslinked photoresist used to provide electrical isolation without adhesive in a very thin layer. Electrical connection to the piezoelectric may be ensured by mixing epoxy with 5% nickel powder to give anisotropic conduction between the copper and piezoelectric (does not conduct sideways, only up and down). The top of the piezoelectric may be connected to the outside top copper ring in any suitable manner, e.g., run down tin/solder (large solder drop that cools as it runs down side of piezoelectric, connecting electrode on FPC and top of piezoelectric), by metallized epoxy applied from the top of the piezoelectric down the side and onto the FPC electrode, etc.

As shown, certain embodiments retain an additional under metal layer (FIG. 7B), and certain embodiments etch away and remove the under layer of metal (FIG. 7A) that is electrically floating between the dielectric and the ejector surface. Without intending to be limited by theory, this under metal layer acts to keep the FPC flat, to thereby assist in piezoelectric bonding, and to allow metal to metal bonding (rather than polymer to metal bonding). However, the addition of a metal layer adds to the stiffness of the FPC. As such, design parameters may be selected depending on the desired end use of the FPC and the charge isolated ejector mechanism.

FIG. 8 shows an exploded top view of the embodiment of FIG. 5B, illustrating exemplary configurations of the layers, which may conform to an exemplary piezoelectric element/ejector surface shape, and may include floating leads to aid in bonding.

Figure 9A:
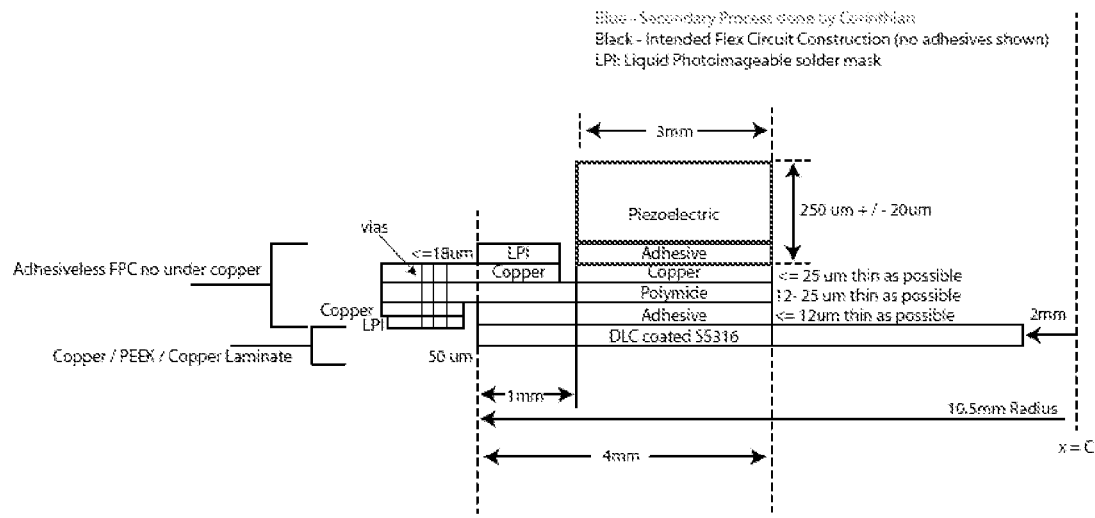
FIG. 9A-9B shows a cross section of FPC bonded to DLC coated SS316L ejector surfaces for (A) no under copper design and (B) under copper design according to certain aspects of the disclosure.
Figure 9B:
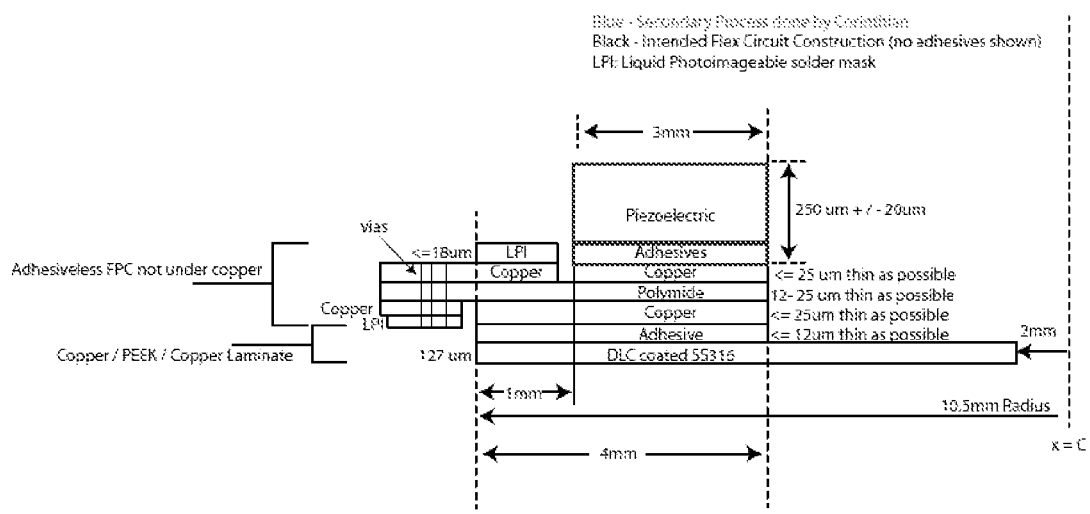
Figure 10:
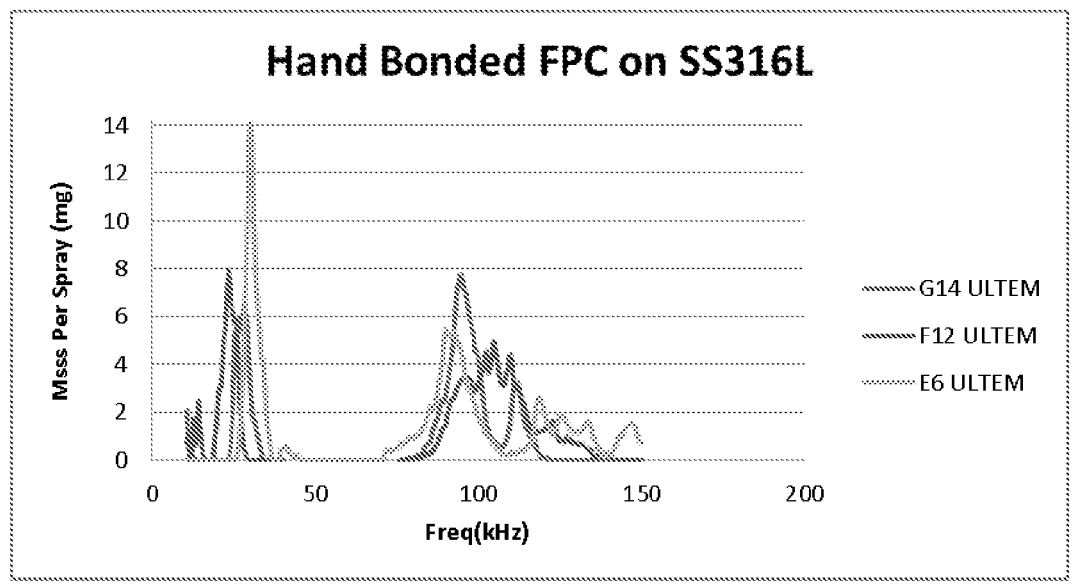
FIG. 10 illustrates exemplary performance evaluation of sample charge isolated ejector mechanisms according to certain aspects of the disclosure.

With reference to FIGS. 9A-9B, an FPC can be made in a similar manner with the same general configuration, and bonded to stainless steel (e.g., DLC (diamond like carbon) coated SS316L), gold, or other suitable ejector surface. Exemplary performance curves of fabricated devices are shown in FIG. 10.

Figure 11A:
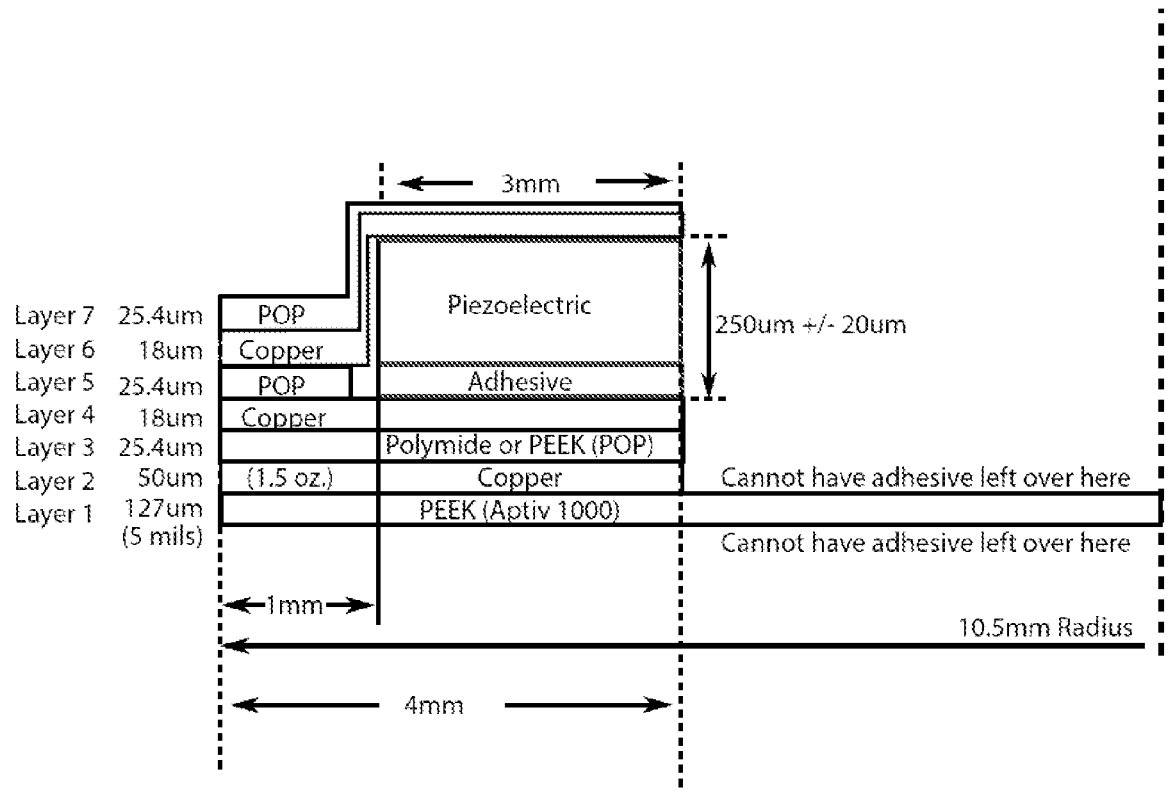
FIG. 11A-11B shows a cross section of multilayer flex circuit ejector (bonded to copper/PEEK/copper ejector surface) with and without flying lead connections according to certain aspects of the disclosure.
Figure 11B:
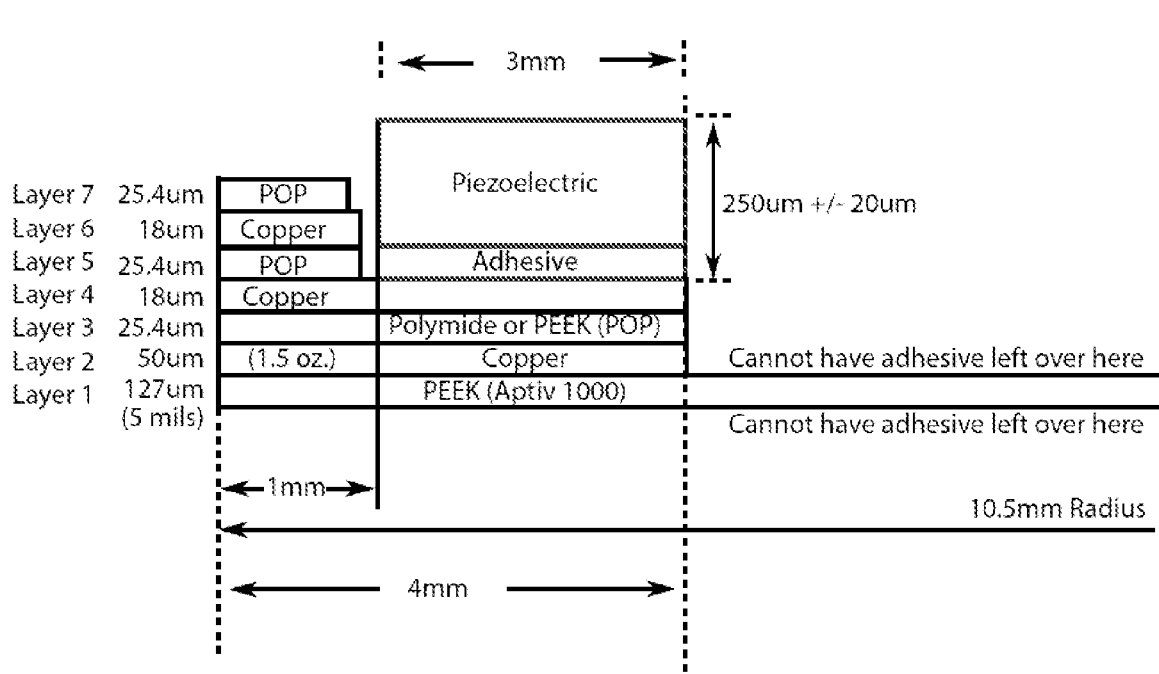

An alterntive FPC configuration utilizing adhesives is illustrated in FIGS. 9A and 9B. With reference to FIGS. 11A and 11B, a multilayer FPC bonded to copper/PEEK/copper ejector surfae with and without flying lead connections (i.e., floating metal leads that connect to the top of the piezoelectric) is shown. In alternative embodiments (not shown), this type of FPC can also be bonded to SS316L, in which case Layer 2 copper may optionally not be included.

Any suitable manner for bonding together of an FPC and an ejector surface may be used. In one embodiment, the bonding together a flexible printed circuit with an ejector surface (e.g., ejector plate coupled to a generator plate) may be achieved, e.g., through surface treatment (roughening through plasma etch, wet etch, mechanical sanding, etc.) and heat pressing past the plastic glass transition temperature at a high compression (typical values 750 F/350 psi polyimide, 350 F/350 psi PEEK, etc.), by applying a thin sheet of adhesive which is cured under heat and pressure specific to the adhesive, or other bonding.

By way of example, FIG. 12 illustrates an exemplary process for generating a charge isolated ejector mechanism from a FPC and a copper/PEEK/copper ejector surface. Generator plate openings may be laser micro-machined out of the PEEK after device fabrication (all photolithography and etching steps). Likewise, FIG. 11 illustrates a general process of bonding an ejector plate (passivated stainless steel sheet) to an FPC. The generator plate (active ejector mesh containing ejector openings) may be subsequently bonded using flexible medical adhesive (flexible glue may be preferred for active area to allow full moding and good ejection). The FPC may also be punched out and bonded to an ejector surface (e.g., stainless steel annuli or PEEK annuli) that are pre-punched, EDM, etched, laser machined, or otherwise fabricated.

In an alternative embodiment, each of the layers of the FPC may be separately cut, e.g., using laser, EDM, etched, punching, or other suitable technique, and then each aligned and bonded separately together with adhesive.

The present disclosure provides for and includes methods for generating droplets of a fluid using a charge isolated ejector surface. In some implementations, the method includes applying a voltage to a piezoelectric actuator operable to oscillate an ejector surface so as to generate droplets of a fluid. In an aspect, the ejector area may have a charge isolated, grounded ejector surface comprising a generator plate. In certain aspects, the charge isolated ejector surface may include an ejector plate coupled to a generator plate. In some further aspects, the charge isolated ejector surface may be grounded. In an aspect, the ejector surface, e.g., comprising an ejector plate and/or generator plate may be coated with an inert material.

Many implementations of the inventions have been disclosed. This disclosure contemplates combining any of the features of one implementation with the features of one or more of the other implementations. For example, any of the ejector mechanisms or reservoirs can be used in combination with any of the disclosed housings or housing features, e.g., covers, supports, rests, lights, seals and gaskets, fill mechanisms, or alignment mechanisms. Further variations on any of the elements of the inventions disclosed and within the scope of ordinary skill are contemplated by this disclosure. Such variations include selection of materials, coatings, or methods of manufacturing.

Any of the electrical and electronic technology can be used with any of the implementations without limitation. Furthermore, any networking, remote access, subject monitoring, e-health, data storage, data mining, or internet functionality is applicable to any and all of the implementations and can be practiced therewith. Further still, additional diagnostic functions, such as performance of tests or measurements of physiological parameters may be incorporated into the functionality of any of the implementations. Performance of glaucoma or other ocular tests can be performed by the devices as a part of their diagnostic functionality. Other methods of fabrication known in the art and not explicitly listed here can be used to fabricate, test, repair, or maintain the device. Furthermore, the device may include more sophisticated imaging or alignment mechanisms. For example, the device or base may be equipped with or coupled to an iris or retina scanner to create a unique identification to match a device to the user, and to delineate between eyes. Alternatively, the device or base may be coupled to or include sophisticated imaging devices for any suitable type of photography or radiology.

To assist in understanding the present inventions, the following examples are included. The experiments described herein should not, of course, be construed as specifically limiting the invention and such variations of the invention, now known or later developed, which would be within the purview of one skilled in the art are considered to fall within the scope of the invention as described herein and hereinafter claimed.

EXAMPLES

Example 1

This example relates to a clinical dilation study using an ejector device of the disclosure on human subjects. This example demonstrates that the delivery of a low dosage volume medicament composition as a directed stream of droplets via an ejector device of the disclosure provides equivalent dilation to that of a standard eye dropper using only ¼ of the dosage volume of the eye dropper.
Materials and Methods In the first arm of the study, thirty-five subjects are dosed with 2×3 µl doses of phenylephrine 2.5% and 2×3 µl doses of tropicamide 1% from an ejector device in one eye (3 minutes apart), and 1× drop (~26 µl) of phenylephrine 2.5% and 1× drop (~26 µl) of tropicamide 1% from a standard eyedropper in the fellow eye. In the second arm of the study, thirty-three subjects are dosed with 1×6 µl dose of phenylephrine 2.5% and 1×6 µl dose of tropicamide 1% from an ejector device in one eye, and 1× drop of phenylephrine 2.5% and 1× drop of tropicamide 1% from an eyedropper in the fellow eye. In the third arm of the study, thirty-four subjects are dosed with 1×1.5 µl dose of phenylephrine 2.5% and 1×1.5 µl dose of tropicamide 1% from an ejector device in one eye, and 1× drop of phenylephrine 2.5% and 1× drop of tropicamide 1% from an eyedropper in the fellow eye.

Figure 15A:
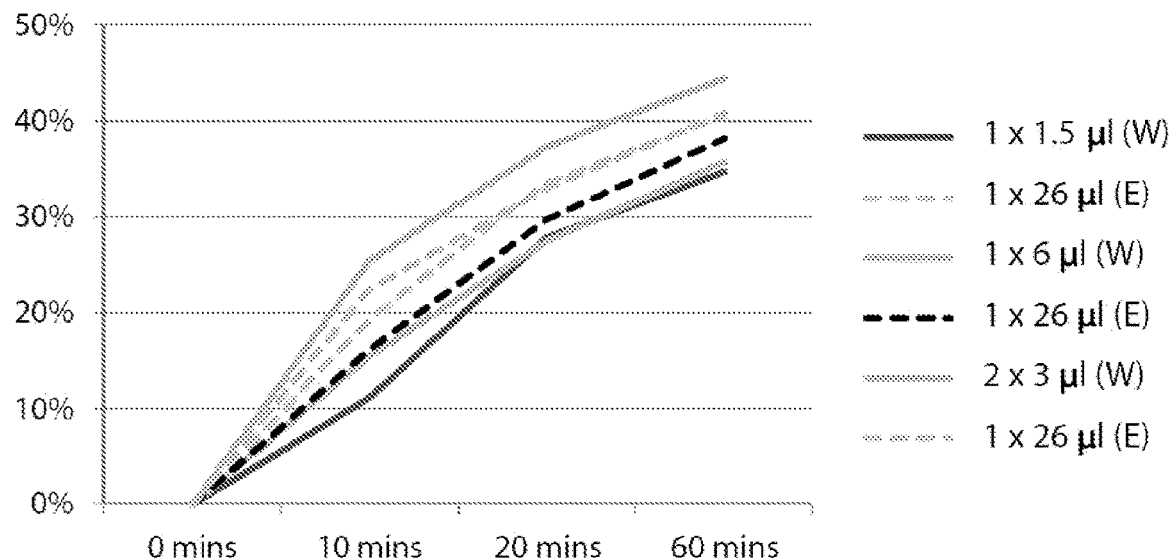
FIG. 15A illustrates mean % change in dilation from baseline using an ejector device of the disclosure (W) vs. standard eyedropper (E); dosages shown apply to each of phenylephrine 2.5% and tropicamide 1%.
Figure 15B:
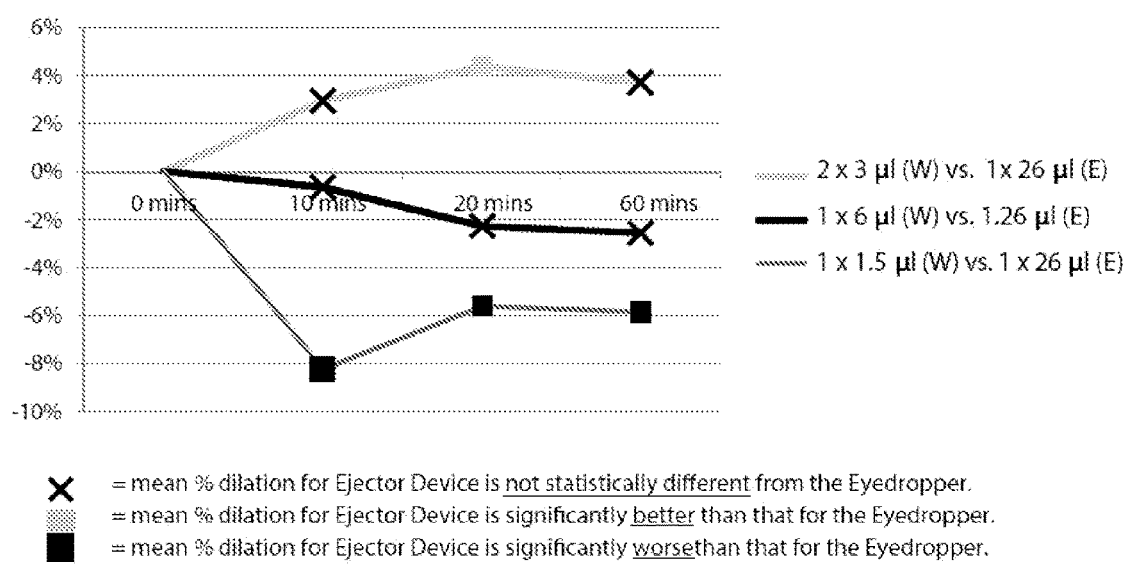
FIG. 15B illustrates mean differences in % dilation using an ejector device of the disclosure (W) vs. standard eyedropper (E); dosages shown apply to each of phenylephrine 2.5% and tropicamide 1% (relative to baseline dilation @ t=0 minutes).

The effectiveness of the three different dosages of 1×1.5 µl, or 1×6 µl, or 2×3 µl of phenylephrine 2.5% delivered by the ejector device versus one drop of phenylephrine 2.5% from the eyedropper, together with 1×1.5 µl, or 1×6 µl, or 2×3 µl of tropicamide 1% delivered by the ejector device versus one drop of tropicamide 1% from the eyedropper, are assessed by measuring the percentage increase in dilation of the subject's pupils at 10 minutes, 20 minutes, and 60 minutes after administering the dosage(s) relative to the pretreatment baseline.
Results FIG. 15A illustrates the mean percentage change in dilation measured from the pretreatment baseline for delivery via a spray ejector device of the disclosure, as compared to traditional eyedropper administration. FIG. 15B illustrates the mean percentage difference in dilation relative to the pre-dosage dilation baseline for the spray ejector device as compared to the eyedropper. Differences are calculated on a subject-specific basis and are then averaged.
Discussion FIG. 15A indicates that the dilation drugs delivered by both the ejector device (e.g., a direct stream of droplets of a low dosage volume medicament composition) and the standard eyedropper materially dilated subjects' eyes, and that the average degree of dilation increases monotonically as more time passed after administering the dosage, up to the maximum post-dosage measurement point of 60 minutes.

FIG. 15B indicates that while the 1×1.5 µl dosage from the ejector device did not achieve a statistically equivalent degree of dilation as the 1× drop from the eyedropper (2-tailed p-values on equivalence <0.001), all the 1×6 µl dosages and two of the three 2×3 µl dosages from the ejector device did achieve a statistically equivalent degree of dilation as the eyedropper (2-tailed p-values for 1×6 µl are all >0.20; 2-tailed p-values for 2×3 µl at 10 minutes and 60 minutes are 0.17 and 0.10, respectively). Moreover, for the 2×3 µl dosage it was the case that 20 minutes after dosing, the ejector device achieved a statistically significantly higher mean dilation than did the eyedropper (2-tailed p-value=0.05).

Example 2

Figure 16A:
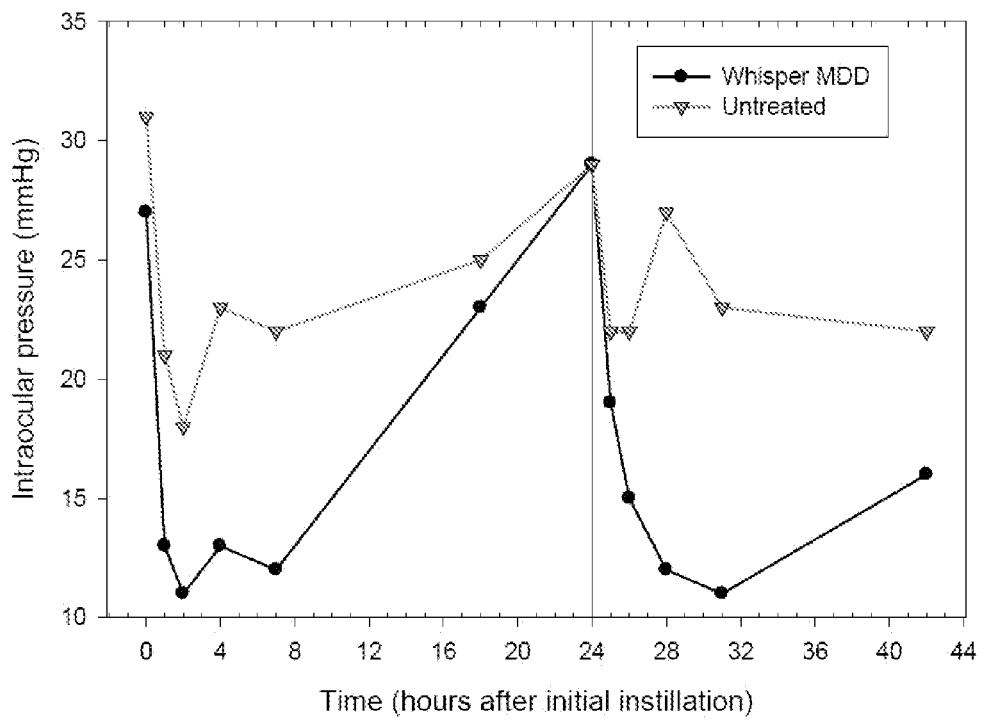
FIG. 16A illustrates intraocular pressure in one dog treated with 1.5 µl of 0.005% latanoprost via a spray ejector device of the disclosure (Whisper MDD).
Figure 16B:
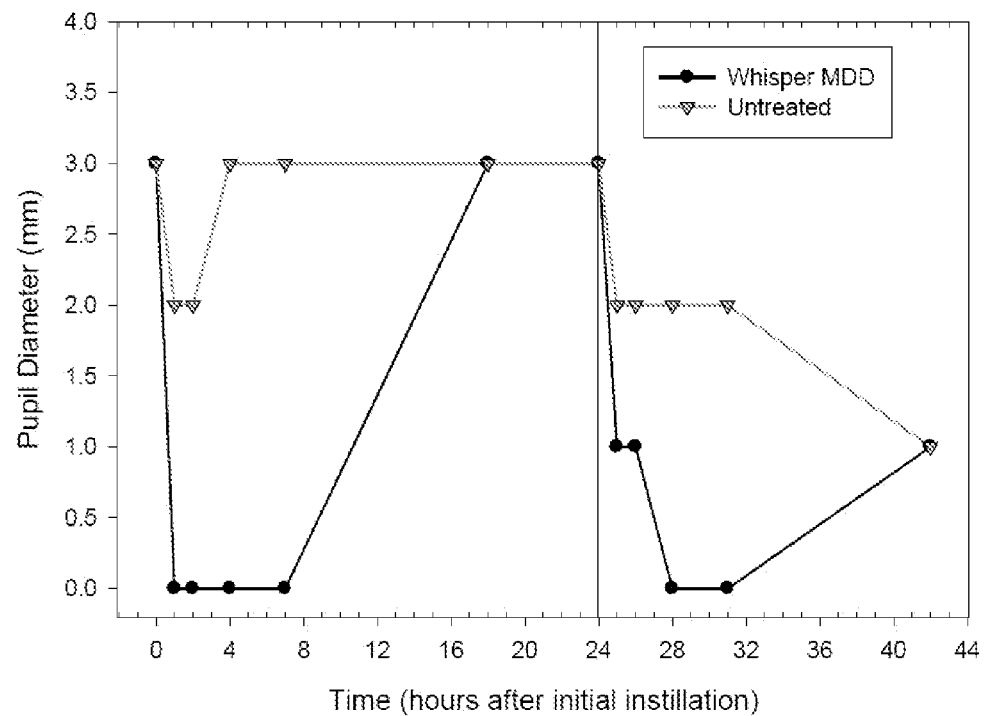
FIG. 16B illustrates pupil diameter in one dog treated with 1.5 µl of 0.005% latanoprost via a spray ejector device of the disclosure (Whisper MDD).

This example relates to a clinical study using glaucomatous beagles to evaluate the effects of latanoprost on intraocular pressure (IOP). More particularly, this study evaluates the reduction in IOP and pupil diameter (PD) following once-daily instillation of 1.5 µl of 0.005% latanoprost via a spray ejector device of the disclosure, as compared to an untreated eye.
Materials and Methods One glaucomatous beagle dog (female, aged 3 years) from the University of Florida MacKay Colony of Glaucomatous Beagles was chosen for this study. The animal was rested a minimum of one week before starting the study. Prior to the commencement of the study, the animal was assigned one eye to receive 1.5 µl of 0.005% latanoprost and the contralateral eye to remain untreated as a control. The basic measurement protocol was followed at all times and performed by the same operator. PD was measured via Jameson Caliper (mm horizontally). IOP was measured using a TonoVet instrument with clean probe (iCare). IOP and PD were measured at time 0, 1, 2, 4, 7 and 18 hours daily for two days. Immediately after the time 0 measurement, the animal received 1.5 µl of 0.005% latanoprost in its assigned eye with a spray device. The contralateral eye was left untreated. The spray device was checked for accuracy before and after every use, and required a 10% delivered dose accuracy in pretreatment. Standard measurements continued throughout each day at time 1, 2, 4, 7 and 18 hours. Possible endpoints included, but were not limited to, excessive ocular irritation, ocular damage, and other illness or injury. No statistical crossover was utilized for this study.
Results IOP in the treated eye was reduced to 11 mmHg, a maximum decrease of 16 mmHg from the initial value, by hour 2 (FIG. 16A). PD was reduced to pinpoint (0) by hour 1 and remained there through hour 7 (FIG. 16B).
Discussion The 1.5 µl dose of 0.005% latanoprost delivered via the Whisper™ MDD device was demonstrated to be as effective at lowering IOP and constricting the pupil as traditional therapy. This study confirms that the spray ejector device is capable of delivering a 1.5 µl dose of latanoprost consistently.

Example 3

Figure 17A:
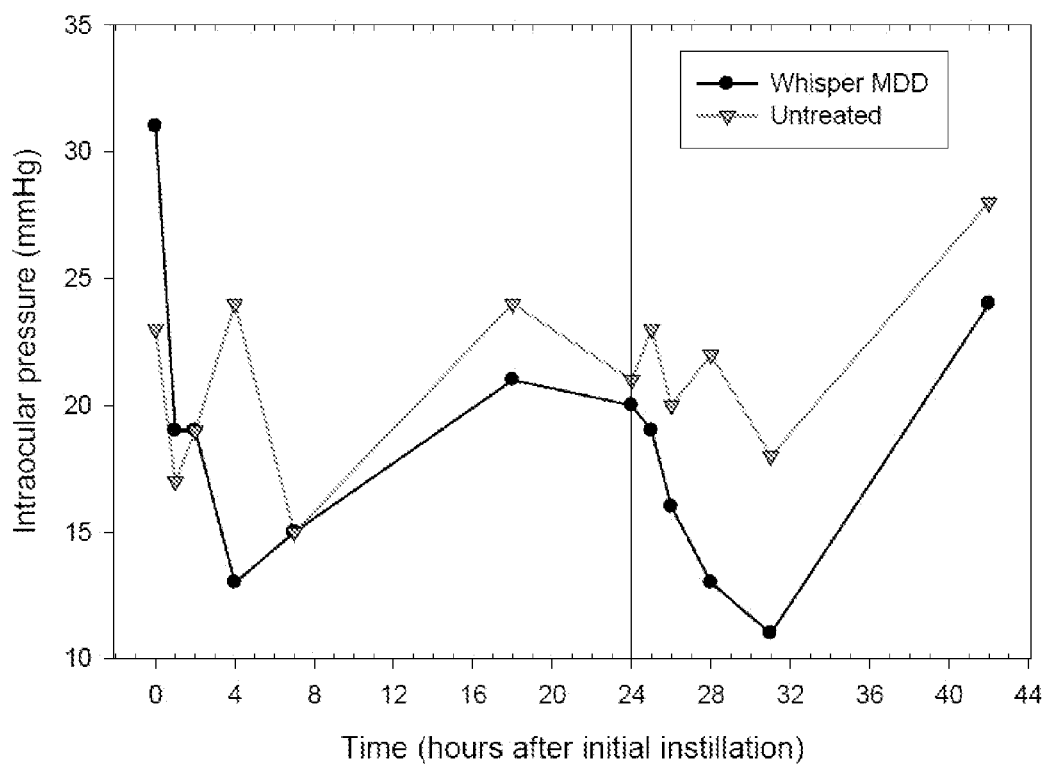
FIG. 17A illustrates changes in intraocular pressure in one dog treated with 3.0 µl of 0.005% latanoprost via a spray ejector device of the disclosure (Whisper MDD).
Figure 17B:
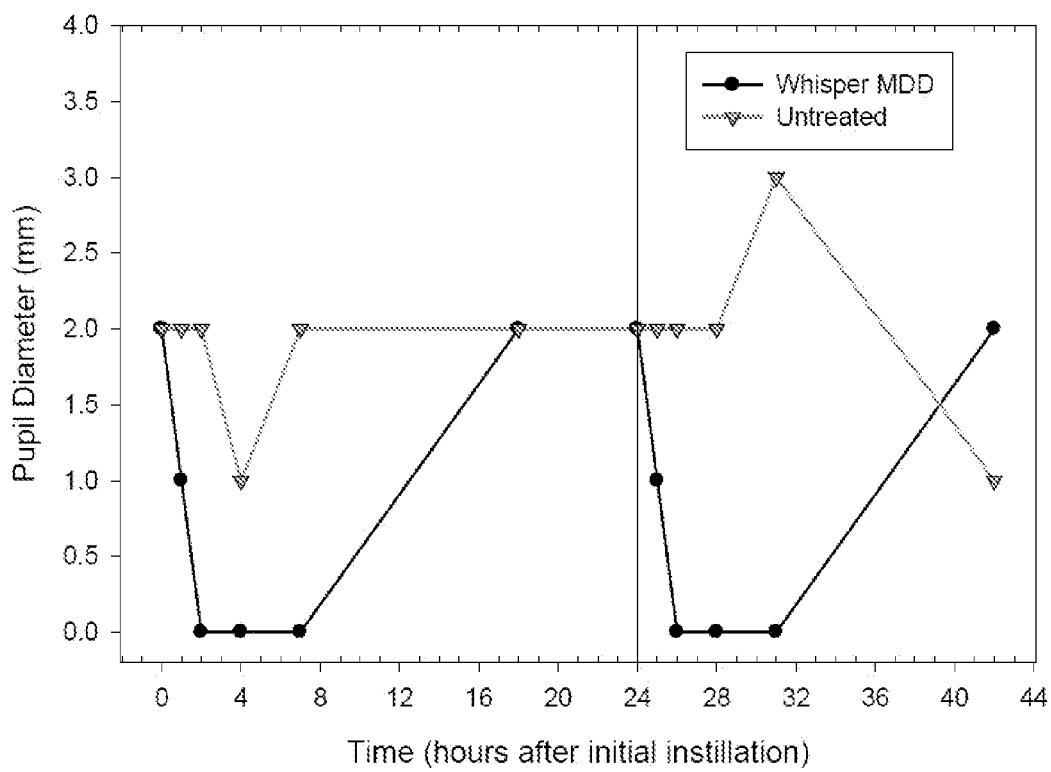
FIG. 17B illustrates pupil diameter in one dog treated with 3.0 µl of 0.005% latanoprost via a spray ejector device of the disclosure (Whisper MDD).

This example relates to a clinical study using glaucomatous beagles to evaluate the effects of latanoprost on intraocular pressure (IOP). More particularly, this study evaluates the reduction in IOP and pupil diameter (PD) following once-daily instillation of 3.0 µl of 0.005% latanoprost using a spray ejector device of the disclosure, as compared to an untreated eye.
Materials and Methods One glaucomatous beagle dog (female, aged 3 years) from the University of Florida MacKay Colony of Glaucomatous Beagles was chosen for this study. Prior to the commencement of the study, the animal was assigned one eye to receive 3.0 µl of 0.005% latanoprost and the contralateral eye to remain untreated as a control. The basic measurement protocol was followed at all times and performed by the same operator. PD was measured via Jameson Caliper (mm horizontally). IOP was measured using a TonoVet instrument with clean probe (iCare). IOP and PD were measured at time 0, 1, 2, 4, 7 and 18 hours daily for two days. Immediately after the time 0 measurements, the animal was administered 3.0 µl of 0.005% latanoprost in its assigned eye using a spray ejector device. The contralateral eye was left untreated. The spray ejector device was checked for accuracy before and after every use, and required a 10% delivered dose accuracy in pretreatment. Standard measurements continued throughout each day at time 1, 2, 4, 7 and 18 hours. Possible endpoints included, but were not limited to, excessive ocular irritation, ocular damage, and other illness or injury. No statistical crossover was utilized for this study.
Results IOP in the treated eye was reduced to 19 mmHg, a decrease of 12 mmHg from the initial value, by hour 2 (FIG. 17A). The maximum decrease was seen at hour 7 on day 2. PD was reduced to pinpoint (0) by hour 1 and remained there throughout hour 7 (FIG. 17B).
Discussion Results indicate that, as with the 1.5 µl dose, the 3.0 µl dose of 0.005% latanoprost is as effective at lowering IOP and constricting the pupil as traditional eyedropper therapy. This study confirms that the spray ejector device is capable of delivering a 3.0 µl dose of latanoprost consistently.

Example 4

This example relates to a clinical study using glaucomatous beagles to evaluate the effects of latanoprost on intraocular pressure (IOP). More particularly, this study evaluates the effects on intraocular pressure (IOP) of once-daily installation of 9 µl of latanoprost via a spray ejector device of the disclosure, as compared to an average of 26 µl of latanoprost delivered once daily by traditional eyedropper.
Materials and Methods Six glaucomatous beagle dogs (4 males and 2 females, aged 3-8 years) from the University of Florida MacKay Colony of Glaucomatous Beagles were chosen for this study. Conditions for inclusion included elevated IOP and documented glaucomatous disease state as determined by gross eye exam by a boarded veterinary ophthalmologist.

All animals were rested for a minimum of one week before starting the trials. IOP and pupil diameter (PD) were measured 5 times (at 0, 1, 2, 4, and 7 hours) daily for four days (study days 1-4) to establish initial baseline levels. The basic measurement protocol was followed at all times and performed by the same operator. PD was measured via Jameson Caliper (mm horizontally). IOP was measured with a TonoVet instrument with clean probe (iCare). After three rest days, one eye was randomly assigned to receive 9 µl of 0.005% latanoprost delivered via a spray ejector device, and the contralateral eye was administered traditional latanoprost from a traditional eyedropper container (26-30 µl).

On study days 5-9, IOP and PD measurements were taken at approximately 0900 h (time 0) Immediately after time 0 measurements, each animal received a once-daily dose of 9 µl of generic 0.005% latanoprost in its assigned eye via the spray ejector device. The contralateral eye received a clinical dose (one drop) of the same commercially available topical drug from a traditional eyedropper (positive control). The spray ejector device was checked for accuracy before and after every use and required a 10% delivered dose accuracy in pretreatment. Standard measurements continued throughout each day at 0, 1, 2, 4, and 7 hours. Possible endpoints included, but were not limited to, excessive ocular irritation, ocular damage, and other illness or injury. No statistical crossover was utilized for this study.

Results

Figure 18A:
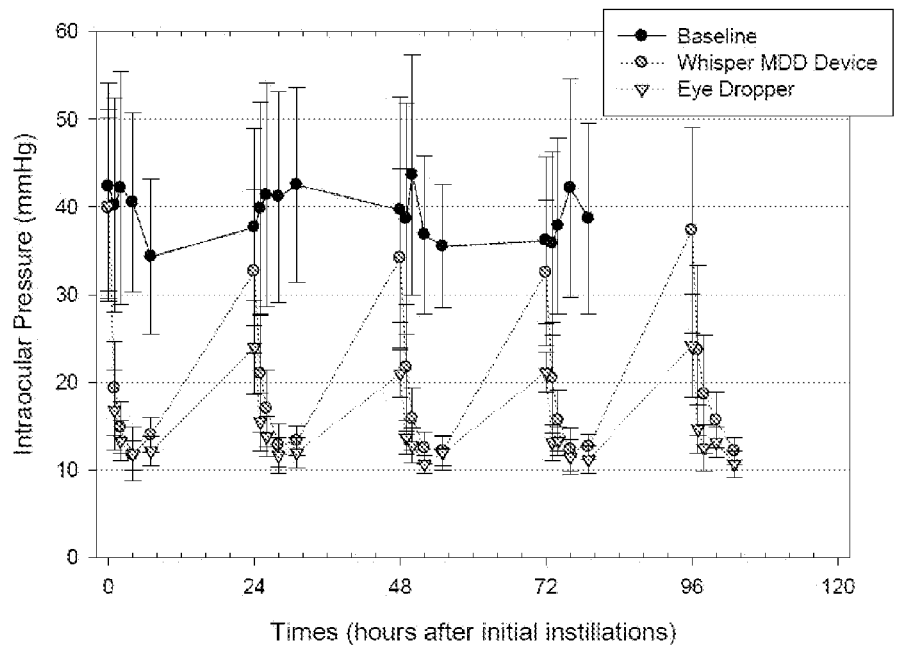
FIG. 18A illustrates intraocular pressure in animals treated with 9.0 µl of 0.005% latanoprost via a spray ejector device of the disclosure (Whisper MDD), compared to traditional eyedropper administration (Eye Dropper).
Figure 18B:
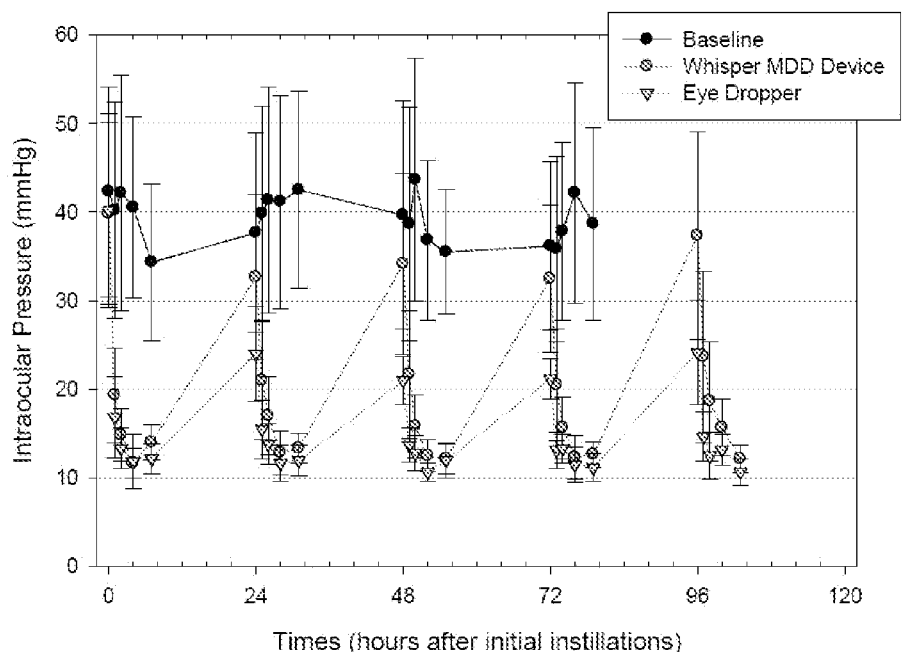
FIG. 18B illustrates pupil diameter in animals treated with 9.0 µl of 0.005% latanoprost via a spray ejector device of the disclosure (Whisper MDD), compared to traditional eyedropper administration (Eye Dropper).

Results for the spray ejector device and generic eyedropper treatments were similar. The 9 µl dose was as effective at lowering IOP and constricting the pupil as traditional therapy. The duration of action of the eyedropper dose was greater, but the spray ejector device therapy maintained values significantly lower than baseline for IOP (FIGS. 18A and 18B). Irritation in eyes treated using the spray ejector device was less than that observed in the eyedropper-treated eyes.

Discussion

Administration of 9 µl of 0.005% latanoprost in a single daily morning dose via a spray ejector device was as effective at controlling IOP as traditional eyedropper therapy, at approximately one-third the typical eyedropper dose over a seven-hour study period for five days. This pharmacodynamic (PD) study is the companion study to the pharmacokinetic (PK) study of Example 12, comparing the bioavailability of the acid of latanoprost in the aqueous humor following delivery of 9 µl of latanoprost via a spray ejector device, as compared to 26 µl of latanoprost delivered via eyedropper.

Example 5

This example relates to a clinical study using glaucomatous beagles to evaluate the effects of latanoprost on intraocular pressure (IOP). More particularly, the study evaluates the effectiveness of lower doses of latanoprost delivered via a spray ejector device in lowering IOP in a side-by-side, randomized, crossover study in six glaucomatous beagles. During the study, IPO of glaucomatous beagles is measured when latanoprost is delivered in two 6 µl doses using an ejector device of the disclosure (e.g., as a low dosage volume directed stream of droplets) versus when delivered as a single drop (~24 µl) from a standard eyedropper.

Materials and Methods

Six glaucomatous animals (4 males and 2 females aged 3-8 years) from the University of Florida (UF) MacKay glaucomatous Beagle colony are chosen for this study. Conditions for inclusion include elevated intraocular pressure (IOP) and documented glaucomatous disease state as determined by gross eye exam by a boarded veterinary ophthalmologist.

All animals are rested a minimum of one week before starting the trials. Intraocular pressure (IOP), pupil diameter (PD), and heart rate (HR) are measured 6 times (at 0, 0:30, 0:45, 1, 2, 7 hrs) daily for five days, for initial baseline levels (Study days 1-5). The basic measurement protocol is followed and performed by the operator. PD is measured via Jameson Caliper (mm horizontally). IOP is measured with a TonoVet instrument with clean probe (iCare). HR is monitored via palpation of the femoral vessels. After two rest days, one eye is randomly assigned to receive the drug delivered via the ejector device and the contralateral eye is given traditional latanoprost from an eye dropper container.

Active drug delivery begins on study day eight. For five days, IOP and PD measurements are taken at 0900. Immediately after 0900 measurements (time 0), each animal receives 6 µl of generic latanoprost in its assigned eye with the ejector device, followed by a second dosing 3 minutes later of an additional 6 µl (to avoid overloading the conjunctival sac). The contralateral eye receives a clinical dose (one drop) of the same commercially-available topical drug from FDA approved container (positive control). The ejector device is checked for accuracy before and after every use (Table 1). Standard measurements continue throughout each day (at 0:30, 0:45, 1, 2, 7 hrs). Possible endpoints include, but are not limited to, excessive ocular irritation, ocular damage, or other illness and injury.

TABLE 1

Calibration measurements for exemplary sample

| Pre-Spray #1 | Post-Spray #1 | Pre-Spray #2 | Post-Spray #2 | Average | Standard Deviation | Percent Variance |
|---|---|---|---|---|---|---|
| 6.8 | 6 | 5.9 | 6 | 6.175 | 0.419 | 6.79% |
| 6.6 | 5.5 | 6.9 | 6 | 6.25 | 0.624 | 9.99% |
| 6.8 | 6.4 | 6.7 | 6.5 | 6.6 | 0.182 | 2.77% |
| 6.7 | 6.5 | 6 | 6.1 | 6.325 | 0.330 | 5.22% |
| 7.2 | 6 | 6.4 | 6.6 | 6.55 | 0.500 | 7.63% |
| 6.9 | 6 | 6.1 | 6.1 | 6.275 | 0.419 | 6.68% |

* Units in µl

After 7 days of rest, starting on study day 22, the treatments are repeated with the only change being the use of opposite eyes for statistical control. All initially assigned drug eyes are now used as positive controls and receive a clinical dose (one drop) of the same commercially-available topical drug from FDA approved eye dropper container. The contralateral eyes now receive 6 µl of generic latanoprost in its assigned eye, followed by a second dosing 3 minutes later of an additional 6 µl, for a total of 12 µl of latanoprost.

Results

Figure 19A:
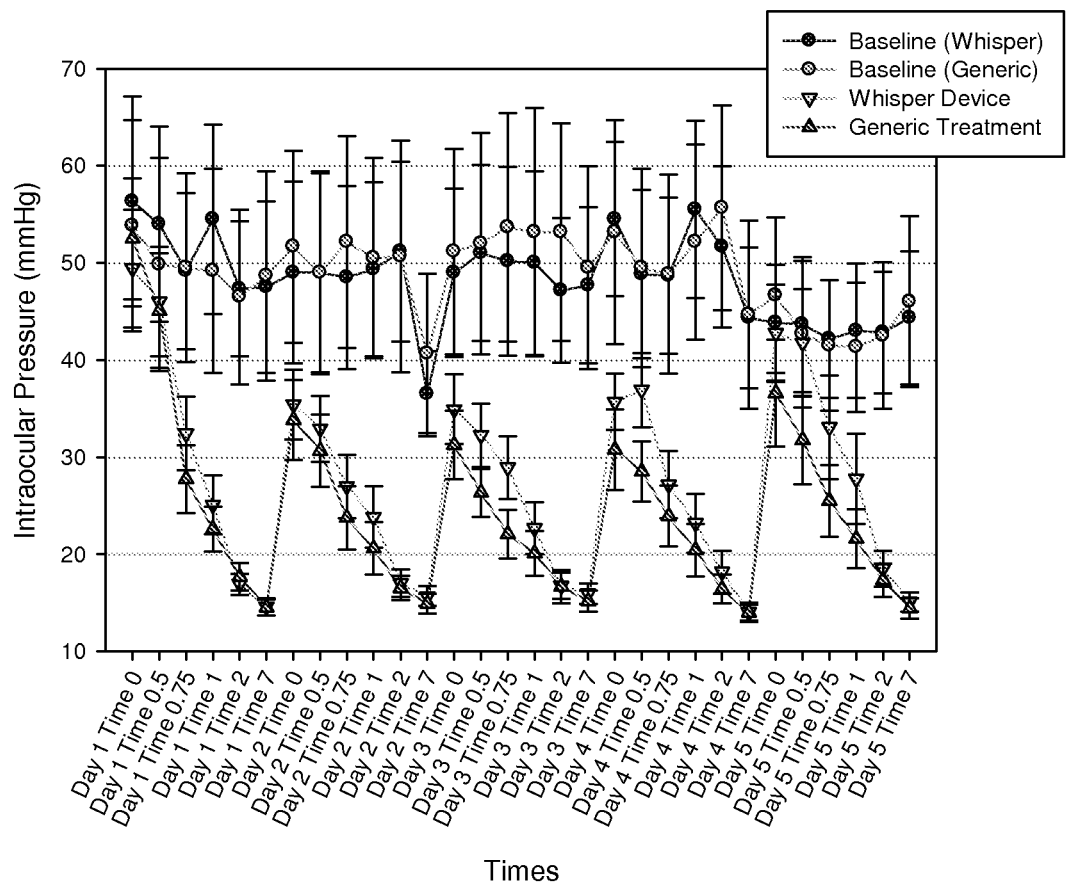
FIG. 19A illustrates intraocular pressure in animals treated with 12.0 µl of 0.005% latanoprost via a spray ejector device of the disclosure (Whisper), compared to traditional eyedropper administration (Generic).
Figure 19B:
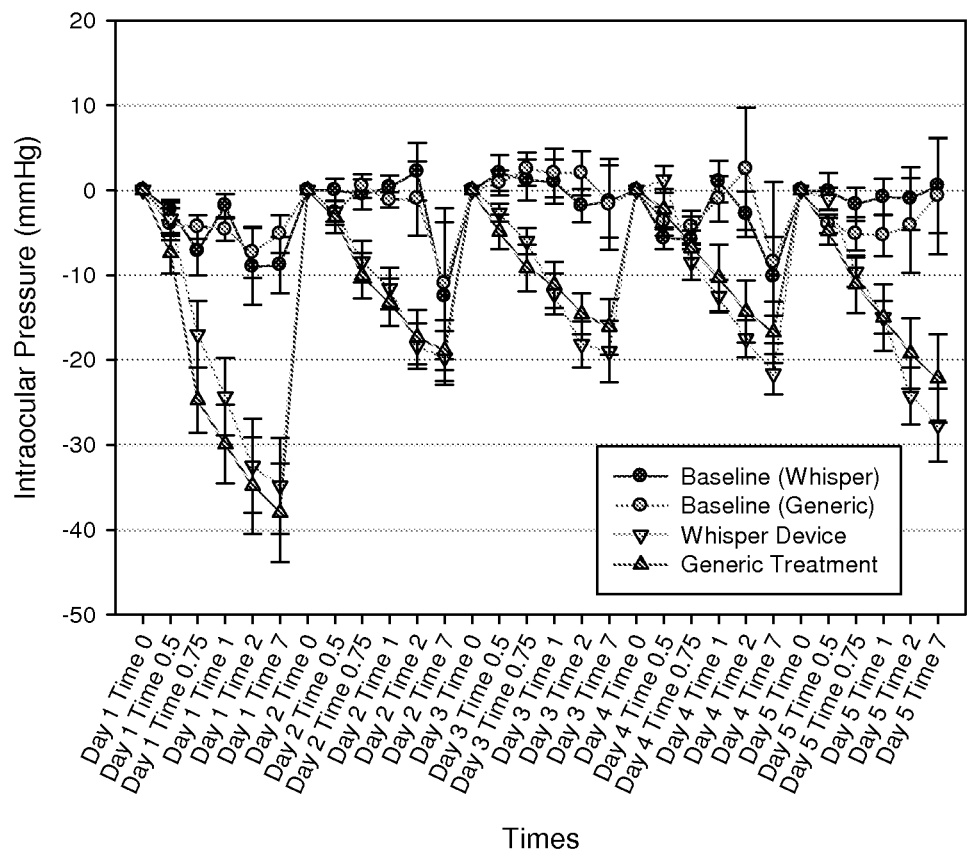
FIG. 19B illustrates changes in intraocular pressure in animals treated with 12.0 µl of 0.005% latanoprost via a spray ejector device of the disclosure (Whisper), compared to traditional eyedropper administration (Generic).
Figure 19C:
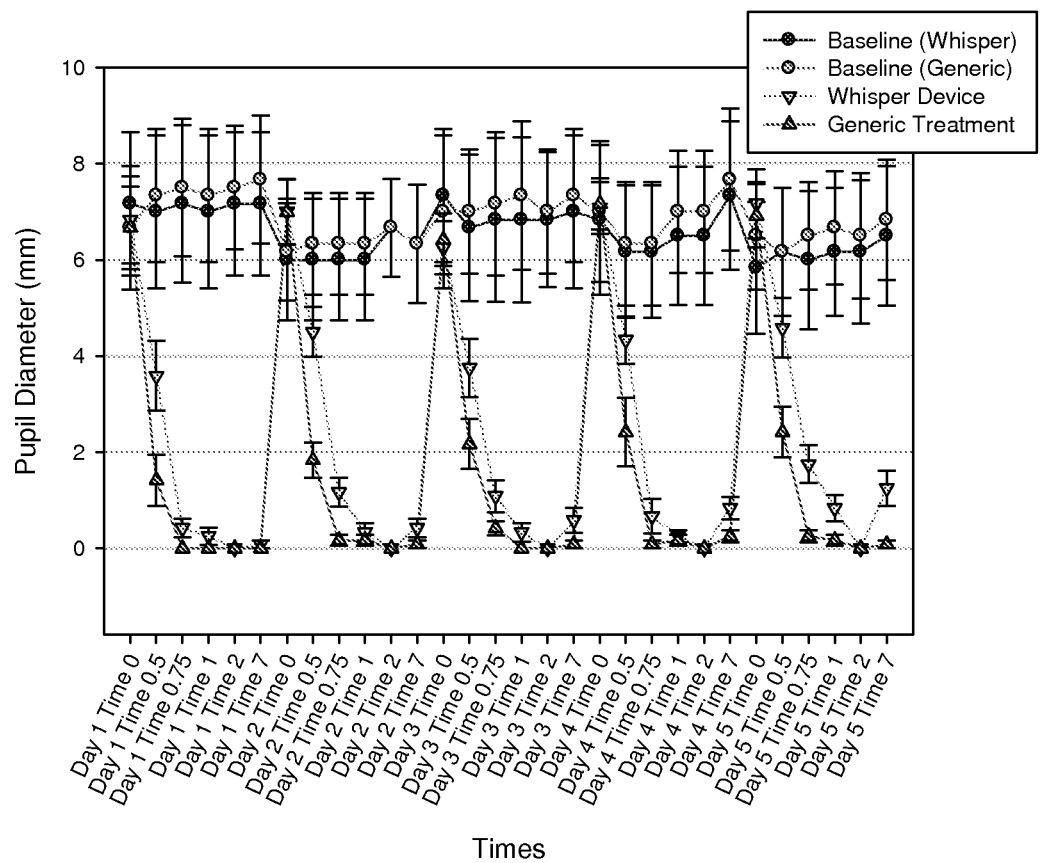
FIG. 19C illustrates pupil diamter in animals treated with 12.0 µl of 0.005% latanoprost via a spray ejector device of the disclosure (Whisper), compared to traditional eyedropper administration (Generic).

FIG. 19A-19C illustrate that the ejector device results generally align with those obtained using a conventional eyedropper. IOP pressure over the course of the study is shown in FIG. 19A, the change in IOP over the course of the study is shown in FIG. 19B, and pupil diameter over the course of the study is shown in FIG. 19C.

Both the ejector device (e.g., a direct stream of droplets of a low dosage volume medicament composition) and traditional eyedropper latanoprost treatments reduced IOP and caused iridal miosis. The ejector device changes in IOP became significantly different from baseline at timepoint 0:45 on day one. The maximum change in IOP during the first 7 hours was −34.8 mmHg (69%). The traditional treatment showed significance in IOP at timepoint 0:45 as well. The maximum change in IOP during the first 7 hours for the traditional treatment was −38.0 mmHg (72%). There were no significant differences between the ejector device treatments and the traditional treatments for IOP.

Significant pupil diameter changes were seen with the ejector device treatment at timepoint 0:30 on day one. The iris reached pinpoint status (maximum miosis) at 1 hour, and remained there for the remainder of the seven hours of monitoring. Significant pupil diameter changes were seen with the traditional latanoprost treatment at timepoint 0:30.

The iris reached pinpoint status at timepoint 1 hour, and remained there for the remainder of the seven hours of monitoring.

There were no changes in heart rate throughout the study with average values around 25 beats/15 seconds (100 bpm). There were no reports of excessive eye irritation or other eye issues. Some conjunctival irritation was noted in the traditional treatment eyes, related to prostaglandin use.

Discussion

In summary, 0.005% latanoprost at low dosage volume significantly lowers IOP in the glaucomatous beagle when instilled once daily, commensurate with standard eyedropper. The reduction in IOP ranged from about 20 mm Hg (45%) to 27 mm Hg (60%). The results show that the reduction in canine IOP achieved by an ejector device of the disclosure (e.g., as a low dosage volume directed stream of droplets) is statistically indistinguishable from that of the dosage volume of a standard eyedropper, even though the two 6 µl doses delivered via the ejector device of the disclosure is approximately ½ of the volume delivered via the standard eyedropper.

Example 6

This example relates to a clinical study using glaucomatous beagles to evaluate the effects of latanoprost on intraocular pressure (IOP). More particularly, the study evaluates the effects on intraocular pressure (IOP) of once-daily instillation of 30 µl of 0.005% latanoprost via a spray ejector device of the disclosure, as compared to once-daily instillation of approximately 26-30 µl by traditional eyedropper.

Materials and Methods

Two glaucomatous beagle dogs (2 females, aged 3-8 years) from the University of Florida MacKay Colony of Glaucomatous Beagles were chosen for this study. Both animals were rested a minimum of one week before starting the trials. Prior to the commencement of the study, each animal was assigned one eye to receive either 30 µl of 0.005% latanoprost delivered by a spray ejector device or one eye drop of 0.005% latanoprost. The basic measurement protocol was followed at all times and performed by the same operator. IOP was measured at time 0, 1, 2, 4, and 7 hours daily for two days using a TonoVet instrument with clean probe (iCare) Immediately after the time 0 measurements, each animal was administered 30 µl of 0.005% latanoprost in its assigned eye using the spray ejector device. The contralateral eye received a clinical dose (one drop) of the same commercially available topical drug from a traditional eyedropper (positive control). The spray ejector device was checked for accuracy before and after every use, and required a 10% delivered dose accuracy in pretreatment. Standard measurements continued throughout each day at time 1, 2, 4, and 7 hours. Possible endpoints included, but were not limited to, excessive ocular irritation, ocular damage, and other illness or injury. No statistical crossover was utilized for this study.

Results

Figure 20:
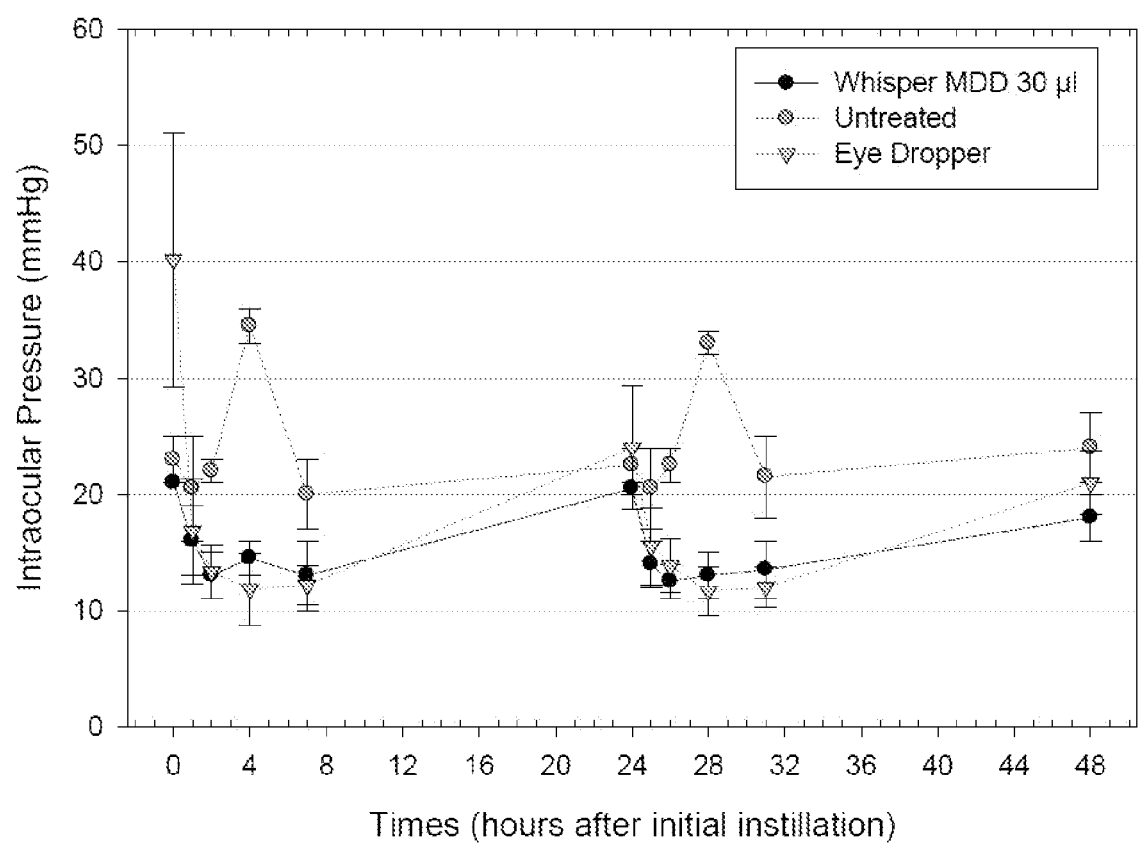
FIG. 20 illustrates intraocular pressure in 2 dogs treated with 30 µl of 0.005% latanoprost via a spray ejector device of the disclosure (Whisper MDD), compared to traditional eyedropper administration (Eye Dropper).

Reduction in IOP for animals treated with the spray ejector device and with the eyedropper were similar (FIG. 20). The 30 µl dose delivered via the spray ejector device was as effective at lowering IOP and constricting the pupil as the traditional eyedropper therapy.

Discussion

Results confirm that the spray ejector device is capable of delivering a 30 µl dose of 0.005% latanoprost. In this pilot study, drug delivery via the spray ejector device was demonstrated to be as effective in controlling IOP as traditional eyedropper therapy, with a trend toward increased duration of action. This study completes the spectrum of the effective dosage range for the delivery of prostaglandin pro-drugs, which is 1.5 µl to 30 µl in this series of studies.

Example 7

This example relates to a randomized cross-over clinical study using glaucomatous beagles to evaluate the effects of travoprost on intraocular pressure (IOP). More particularly, the study compares the effectiveness of a 9 µl dose of 0.004% travoprost (Travatan Z®, Alcon Laboratories, Fort Worth, Tex. USA) delivered by a spray ejector device of the disclosure, as compared to delivery by micropipette in suppressing and flattening the 24-hour intraocular pressure (IOP) dose/response curve and controlling the morning intraocular pressure (IOP) spikes. This study also compares delivery effectiveness of the spray ejector device, as compared to standard micropipette by monitoring IOP and ocular irritation.

Prior to the development of the spray ejector devices and methods of the disclosure, investigational and commercially available prostaglandin agonists have been delivered by eyedropper in volumes of approximately 26 µl. Patients who are intolerant to preservatives or who have concomitant ocular surface diseases (OSD) have been treated with single-dose pipettes using eyedropper-equivalent doses of pharmacy-compounded preservative-free drugs. This method is fraught with safety and ease-of-use issues. Recently, single-dose delivery of eyedropper-equivalent doses of preservative-free, IOP-lowering drugs has been marketed in sterile blow-fill pipettes. Eye injury and usability issues, however, remain.

For drugs delivered in low volume doses by a spray ejector device of the disclosure, the exposure to preservatives per dose may be reduced, and preservative-induced ocular irritation is further reduced by once-daily dosing.

Materials and Methods

Six glaucomatous beagles (3 males and 3 females, aged 3-8 years) from the University of Florida MacKay Colony of Glaucomatous Beagles were chosen for this study. Conditions for inclusion included elevated IOP and documented glaucomatous disease state as determined by gross eye exam by a boarded veterinary ophthalmologist.

All animals were rested a minimum of one week before starting the trials. Intraocular pressure (IOP), pupil diameter (PD), and heart rate (HR) were measured daily at time 0, 12, 13, 14, 16, and 19 hours for five days starting at approximately 2100 h to establish initial baseline levels (study days 1-5). The basic measurement protocol was followed at all times and performed by the same trained operator. PD was measured via Jameson Caliper (mm horizontally). IOP was measured using a TonoVet instrument with clean probe (iCare). HR was monitored via palpation of the femoral vessels. After two rest days, one eye of each animal was randomly assigned to receive 9 µl of 0.004% travoprost delivered via a spray ejector device, and the contralateral eye was assigned treatment with an identical dose delivered via micropipette.

Active drug delivery began on study day 8. For five days, IOP and PD measurements were taken at approximately 2100 h. Immediately after this measurements (time 0), each animal received 9.0±0.9 µl of 0.004% travoprost (Travatan Z®, Alcon Laboratories, Fort Worth, Tex. USA) in its assigned eye via the spray ejector device. The contralateral eye received an identical dose (9.0 µl) of the same drug (positive control) administered via micropipette. The spray ejector device and micropipette were checked for accuracy before and after every use. Standard measurements continued throughout each day at 12, 13, 14, 16, 19 hours. Possible endpoints included, but were not limited to, excessive ocular irritation, ocular damage, and other illness or injury.

After 7 days of rest, starting on study day 22 the treatments were repeated as above except using opposite eyes for statistical control. All initially assigned drug eyes were now used as positive controls and received 9 µl of 0.004% travoprost via micropipette. The contralateral eyes received 9 µl of 0.004% travoprost via the spray ejector device.

Results

Figure 21A:
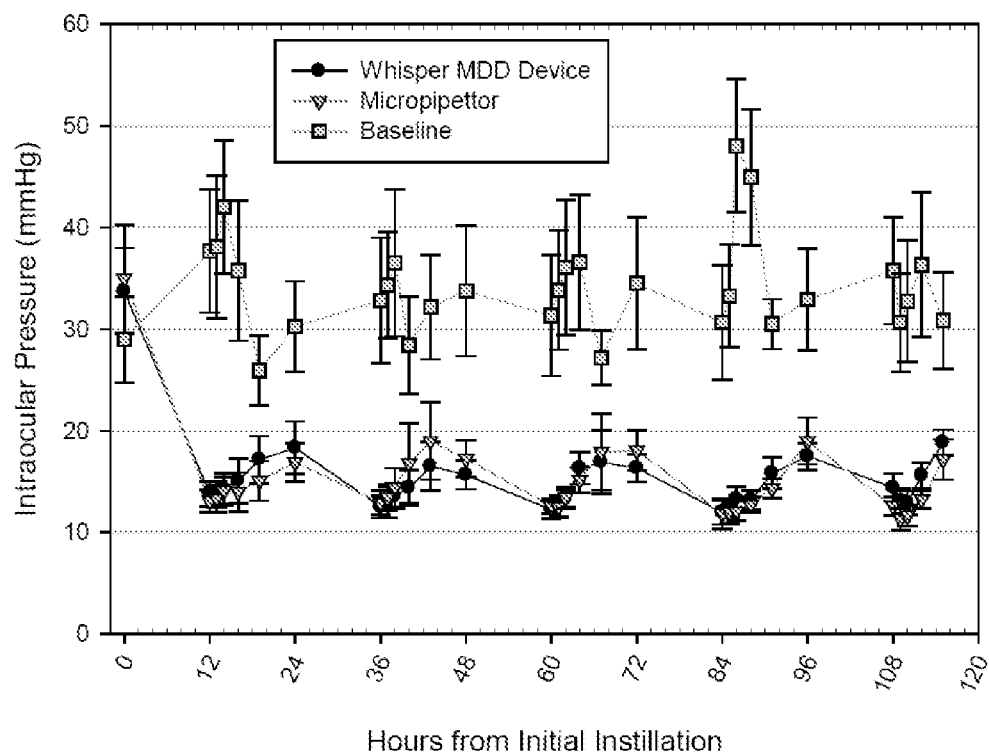
FIG. 21A illustrates intraocular pressure in animals treated with 9.0 µl of 0.004% travoprost via a spray ejector device of the disclosure (Whisper MDD), compared to traditional pippette administration (Micropipettior).
Figure 21B:
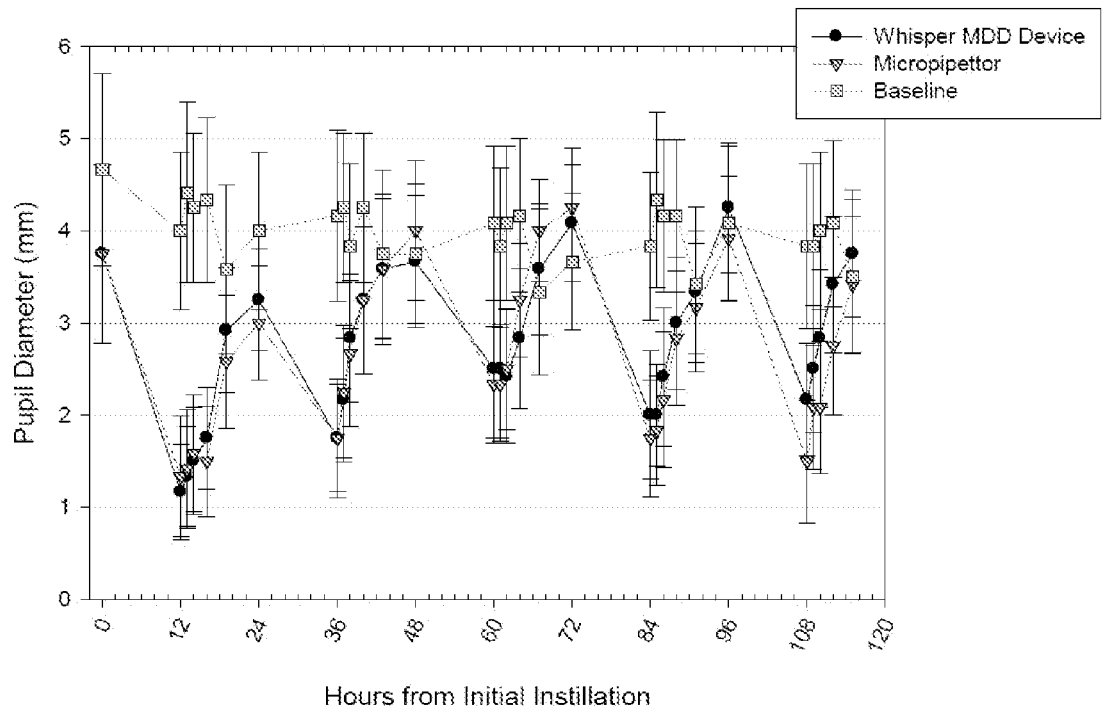
FIG. 21B illustrates pupil diameter in one dog treated with 9.0 µl of 0.004% travoprost via a spray ejector device of the disclosure (Whisper MDD), compared to traditional pippette administration (Micropipettior).
Figure 22A:
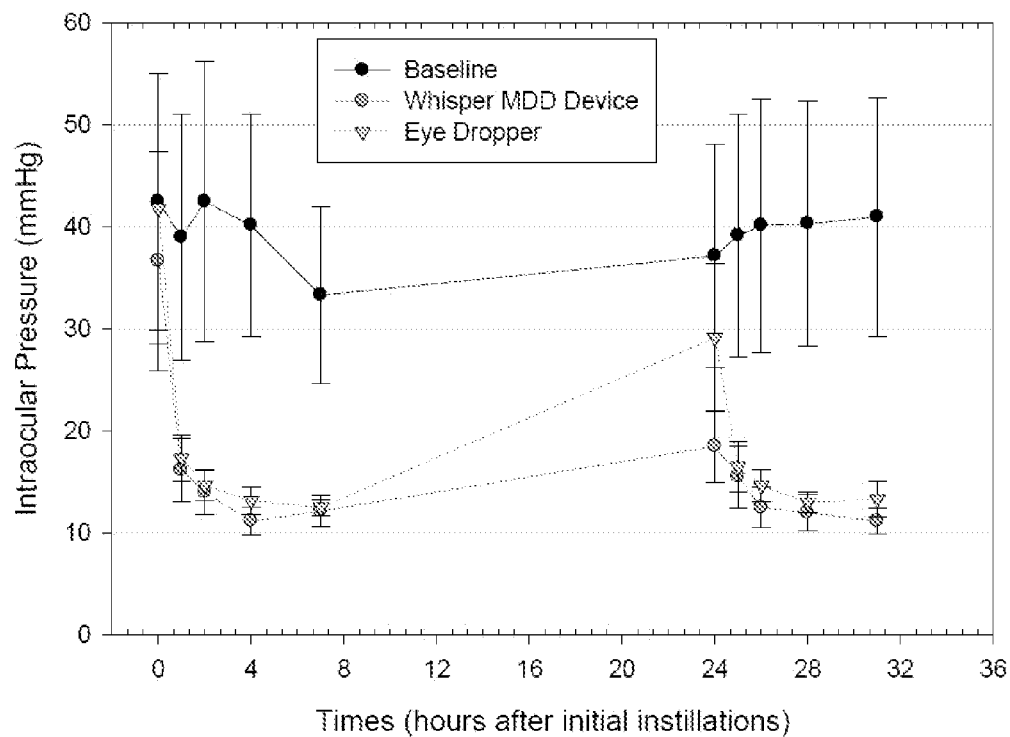
FIG. 22A illustrates intraocular pressure in animals treated with 18.0 µl of 0.004% travoprost in the morning via a spray ejector device of the disclosure (Whisper MDD), compared to traditional eyedropper administration (Eye Dropper).
Figure 22B:
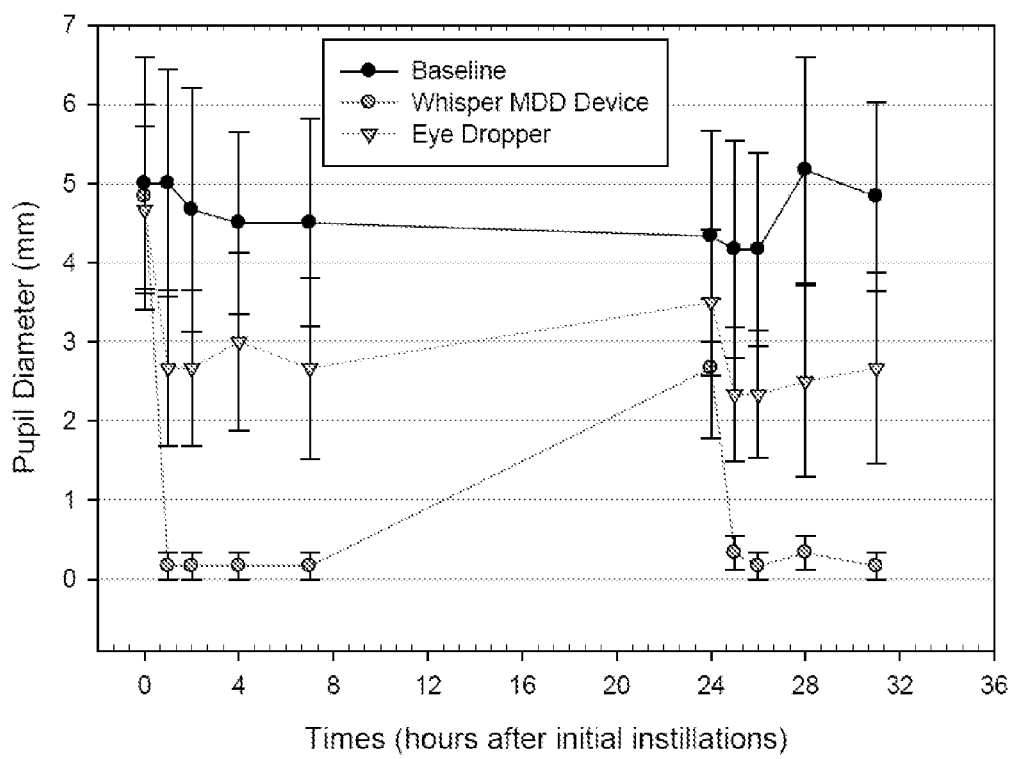
FIG. 22B illustrates pupil diameter in one dog treated with 18.0 µl of 0.004% travoprost in the morning via a spray ejector device of the disclosure (Whisper MDD), compared to traditional eyedropper administration (Eye Dropper).
Figure 22C:
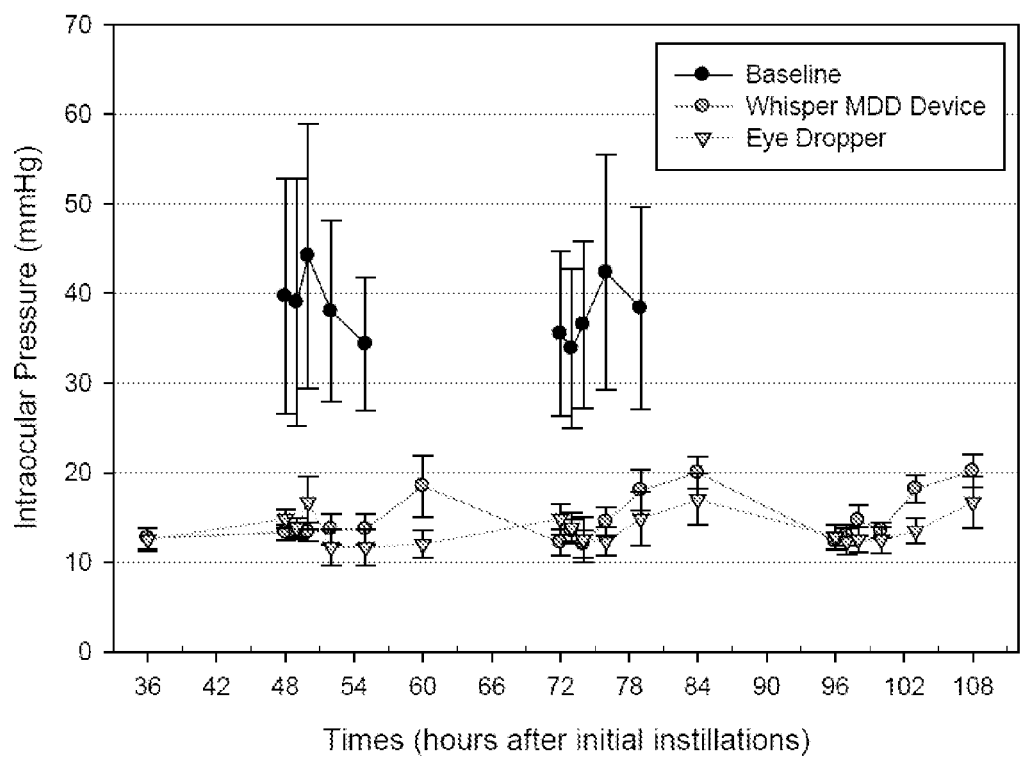
FIG. 22C illustrates intraocular pressure in animals treated with 18.0 µl of 0.004% travoprost in the evening via a spray ejector device of the disclosure (Whisper MDD), compared to traditional eyedropper administration (Eye Dropper).
Figure 22D:
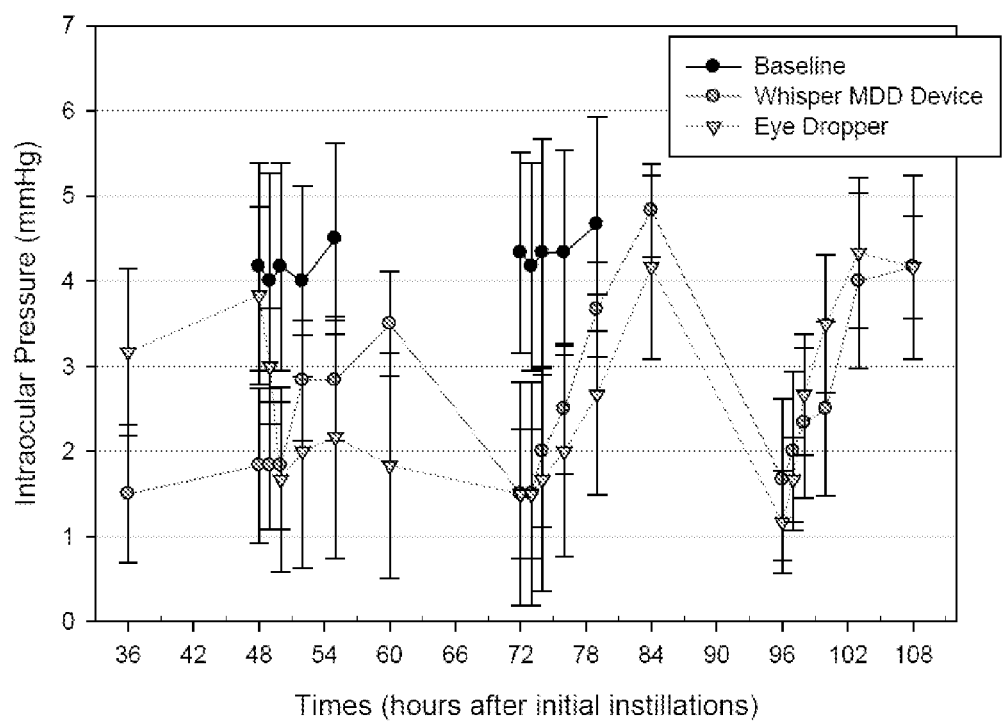
FIG. 22D illustrates pupil diameter in one dog treated with 18.0 µl of 0.004% travoprost in the evening via a spray ejector device of the disclosure (Whisper MDD), compared to traditional eyedropper administration (Eye Dropper).

The spray ejector device caused significant changes in IOP from baseline at time 12 hours on study day 1. The maximum change in IOP during the first 24 hours was −20.0 mmHg (59%). The initial average IOP level on day 1 was 33.75 mmHg; after 5 days of treatment, the highest average daily peak observed was 18.83 mmHg, well below similar baseline levels of 30.83 mmHg (FIG. 21A). Significant PD changes were seen with the spray ejector device treatment at time 12 hours on study day 1. The iris reached maximum miosis (1.17 mm) at time 12 hours and began rising to baseline levels over the remaining hours of monitoring (FIG. 21B). There were no changes in HR throughout the study, with values averaging 25 beats/15 seconds (100 bpm). There were no reports of excessive eye irritation or other eye issues.

Both the spray ejector device and the micropipette functioned well. There were no statistically significant differences between the treatments throughout the study ($p=0.7546$). This demonstrates the effectiveness of travoprost at low volume doses, regardless of delivery method. However, issues relating to delivery methods should be noted. Both treatment methods showed similar levels of overall irritation.

Discussion

Travoprost is the most effective of the prostaglandin agonists studied for lowering of IOP over a 24 hour period day after day including excellent control of morning IOP spike often seen with treatment with prostaglandin pro-drugs.

Example 8

This example relates to a randomized cross-over clinical study using glaucomatous beagles to evaluate the effects of travoprost on intraocular pressure (IOP). More particularly, the study evaluates the effects on intraocular pressure (IOP) following once daily, morning or evening, instillations of 18 µl of 0.004% travoprost by a spray ejector device of the disclosure, as compared to an average of 26 µl delivered once daily by traditional eyedropper.

Materials and Methods

Six glaucomatous beagle dogs (4 males and 2 females, aged 3-8 years) from the University of Florida MacKay Colony of Glaucomatous Beagles were chosen for this study. Conditions for inclusion included elevated intraocular pressure (IOP) and documented glaucomatous disease state as determined by gross eye exam by a boarded veterinary ophthalmologist.

All animals were rested a minimum of one week before starting the trials. IOP and pupil diameter (PD) were measured at time 0, 1, 2, 4, 7, and 12 hours daily for four days (study days 1-4) to establish initial baseline levels. The basic measurement protocol was followed at all times and performed by the same operator. PD was measured via Jameson Caliper (mm horizontally). IOP was measured using a TonoVet instrument with clean probe (iCare). After three rest days, one eye was randomly assigned to receive 18 µl travoprost delivered via a spray ejector device in two 9 µl doses, and the contralateral eye was administered a dose of travoprost (average 26 µl) from a traditional eyedropper container.

On study days 5 and 6, IOP and PD measurements were taken at approximately 0900 h. Immediately after this measurements (time 0), each animal was administered 18 µl of travoprost in its assigned eye via the spray ejector device. The contralateral eye received a clinical dose (one drop) of the same commercially available topical drug from a traditional eyedropper (positive control). The spray ejector device was checked for accuracy before and after every use and required a 10% delivered dose accuracy in pretreatment. Standard measurements continued throughout each day at time 0, 1, 2, 4, 7, and 12 hours.

On study days 7-9, immediately after the time 12 hour (approximately 2100 h) measurements, each animal was administered 18 µl of travoprost in its assigned eye via the spray ejector device. The contralateral eye received a clinical dose (one drop) of the same commercially available topical drug from a traditional eyedropper (positive control). The spray ejector device was checked for accuracy before and after every use and required a 10% delivered dose accuracy in pretreatment. Standard measurements continued throughout each day at time 0, 1, 2, 4, 7, and 12 hours. Possible endpoints included, but were not limited to, excessive ocular irritation, ocular damage, and other illness or injury. No statistical crossover was utilized for this study.

Results

Results for the spray ejector device and traditional eyedropper were similar. The 18 µl dosage delivered by the spray ejector device was as effective at lowering IOP and constricting the pupil as the traditional therapy. The difference in duration of IOP lowering following drug delivery with the spray ejector device, as compared with the eyedropper was not significant. Both treatments maintained IOP values much lower than baseline for a full 24 hours throughout the duration of the study (FIGS. 22A-22D). Irritation in eyes treated using the spray ejector device was less than that observed in the eyedropper-treated eyes.

Discussion

The delivery of an 18 µl morning or evening dose of travoprost via a spray ejector device is as effective at controlling IOP as traditional therapy, even at approximately two-thirds of the average eyedropper-delivered dose (26 µl). Post-treatment IOP remained consistently below 20 mmHg. Based upon mathematical models, including the effect of diurnal variation in IOP and prior studies in this series, once-daily evening dosing of travoprost should provide the best 24-hour lowering of IOP. The noted lack of ocular irritation with the spray ejector device indicate its use in prostaglandin pro-drug-sensitive patients, patients with concomitant ocular disease, and patients with severe glaucoma requiring optimal control.

Example 9

This example relates to a clinical study using glaucomatous beagles to evaluate the effects of bimatoprost on intraocular pressure (IOP). More particularly, the study evaluates the effects on intraocular pressure (IOP) and pupil diameter (PD) of once-daily morning instillations of 6 µl of 0.03% bimatoprost (Lumigan®; Allergan, Irvine, Calif.

USA) by a spray ejector device of the disclosure, as compared to delivery once daily of an average of 26 μl by traditional eyedropper.

Materials and Methods

Six glaucomatous beagle dogs (4 males and 2 females, aged 3-8 years) from the University of Florida MacKay Colony of Glaucomatous Beagles were chosen for this study. Conditions for inclusion included elevated IOP and documented glaucomatous disease state as determined by gross eye exam by a boarded veterinary ophthalmologist.

All animals were rested a minimum of one week before starting the trials. IOP and PD were measured at time 0, 1, 2, 4, and 7 hours daily for four days (study days 1-4) to establish initial baseline levels. The basic measurement protocol was followed at all times and performed by the same operator. PD was measured via Jameson Caliper (mm horizontally). IOP was measured using a TonoVet instrument with clean probe (iCare). After three rest days, one eye was randomly assigned to receive 6 μl of 0.03% bimatoprost delivered via a spray ejector device, and the contralateral eye was assigned to receive traditional bimatoprost from a traditional eyedropper container (26-30 μl).

On study days 5-9, IOP and PD measurements were taken at approximately 0900 h (time 0). Immediately after these measurements, each animal received 6 μl of 0.03% bimatoprost in its assigned eye via the spray ejector device. The contralateral eye received a clinical dose (one drop) of the same commercially available topical drug from a traditional eyedropper (positive control). The spray ejector device was checked for accuracy before and after every use and required a 10% delivered dose accuracy in pretreatment. Standard measurements continued throughout each day at 0, 1, 2, 4, and 7 hours. Possible endpoints included, but were not limited to, excessive ocular irritation, ocular damage, and other illness or injury. No statistical crossover was utilized for this study.

Results

Figure 23A:
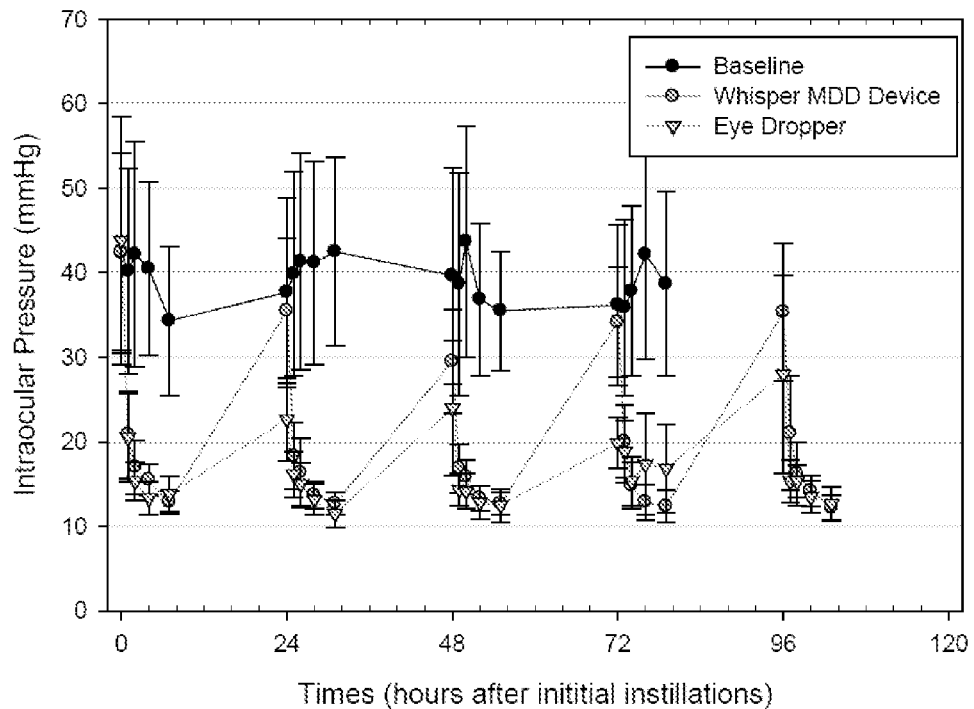
FIG. 23A illustrates intraocular pressure in animals treated with 6.0 µl of 0.03% bimatoprost via a spray ejector device of the disclosure (Whisper MDD), compared to traditional eyedropper administration (Eye Dropper).
Figure 23B:
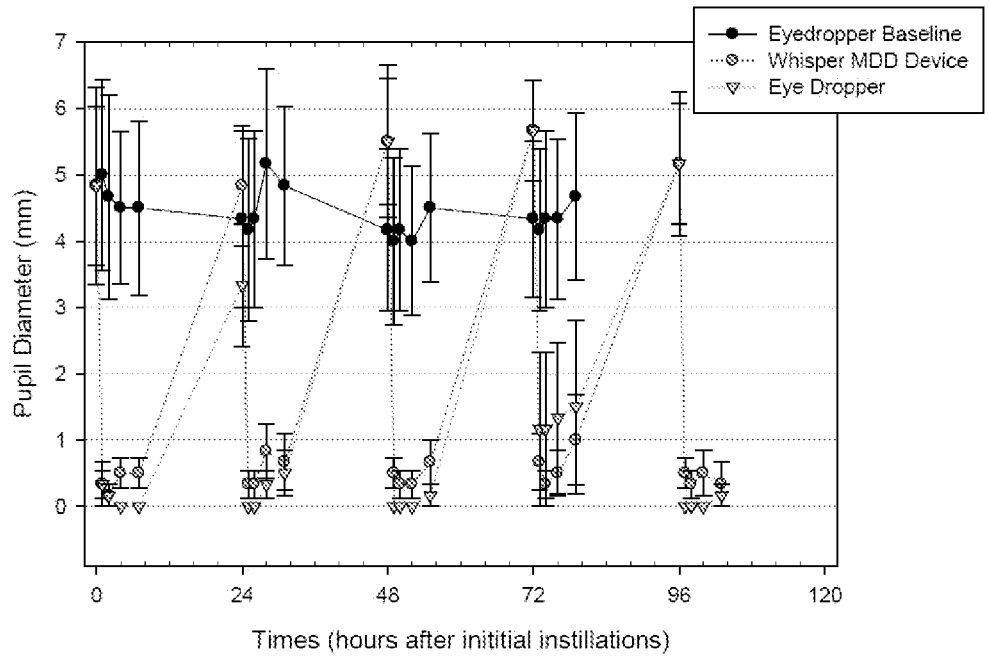
FIG. 23B illustrates pupil diameter in one dog treated with 6.0 µl of 0.03% bimatoprost via a spray ejector device of the disclosure (Whisper MDD), compared to traditional eyedropper administration (Eye Dropper).

Results for the spray ejector device and the traditional eyedropper were similar. The 6 μl dose was as effective at lowering IOP and constricting the pupil as traditional therapy. The duration of the dose administered by eyedropper was greater, but the spray ejector device therapy maintained IOP values that were lower than baseline (FIGS. 23A-23B). Markedly less irritation was observed in eyes treated using the spray ejector device, as compared to the eyes receiving the traditional eye drop treatment Discussion The once-daily morning delivery of 6 μl of 0.3% bimatoprost via a spray ejector device is as effective at controlling IOP as is the traditional therapy, even at less than one-fourth of the average eyedropper dose of 26 μl. Lack of ocular irritation was noted during the study.

Example 10

This example relates to a clinical study using glaucomatous beagles to evaluate the reduction in IOP achieved by low dosage volume medicament compositions comprising modified active agent concentrations, as compared to standard eyedroppers. More particularly, this study evaluates the effectiveness of lower-volume, higher-concentration latanoprost delivered via a spray ejector device in lowering IOP in a side-by-side, randomized crossover study in six glaucomatous beagles.

Materials and Methods

Six Beagle dogs with differing levels of hereditary glaucoma were used. All animals were from an existing colony of glaucomatous Beagles housed at the University of Florida. 4 males and 2 females aged three to nine years were selected for this study. All dogs weighed at least 5 kg. No acclimation or quarantine was necessary. Animals were identified by tattoo, microchip and markings.

Dogs were examined to ensure that they were healthy before placement on study. Dogs were housed in indoor runs large enough to exempt them from exercise requirements. Animals were exposed to natural environmental elements, such as temperature and humidity. Housing and sanitation were performed according to University of Florida Animal Care Services (UF ACS) protocols.

Dogs were provided a laboratory canine diet (Teklad Global 21% Protein Dog Diet). Diet certification and analysis were provided by the vendor, Harlan Teklad. Dogs were provided tap water ad libitum. No contaminants were known to exist in the water and no analysis outside that provided by the local water district and as specified in UF ACS protocols was performed. Environmental parameters (temperature and humidity) were measured daily.

Ophthalmic examinations (slit lamp with fluorescein and indirect ophthalmoscopy) were performed on the eyes of each animal prior to Study Day 1. Ocular findings were scored according to the McDonald-Shadduck Score System. Ocular findings were recorded using a standardized data collection sheet. Macroscopic observations were recorded in accordance with the Draize Scale for Scoring Ocular Lesions. Animals were assigned treatments based on basic randomization prior to study day one.

A 6.0±0.6 μl 5× concentration (0.025%) of latanoprost, formulated by Westlab Pharmacy, was instilled in one randomized eye of each animal using a spray ejector device. Each 6 μl dose from the ejector device included 5× the active agent concentration of standard eyedropper latanoprost. The reformulated latanoprost was targeted to contain the same amount of active agent as that of a standard drop from an eyedropper, but have only approximately ¼ the volume of liquid. The contralateral eye received one drop of commercially available generic latanoprost with supplied eye dropper. All spray ejector device treatments were verified for delivery accuracy using pretreatment and post treatment calibration measurements. All pretreatments were expected to be within 10% (0.6) of the target 6.0 μl before use.

Following a 7 day rest period, the eye choice was reversed. Measurements of IOP, heart rate and pupil diameter (PD) were made at 0:15, 0:30, 0:45, 1, 2, 4, 7, and 18 hours in the primary and crossover study. A veterinary ophthalmologist evaluated each test subject before and after the study for evidence of ocular side effects.

Results

Figure 24A:
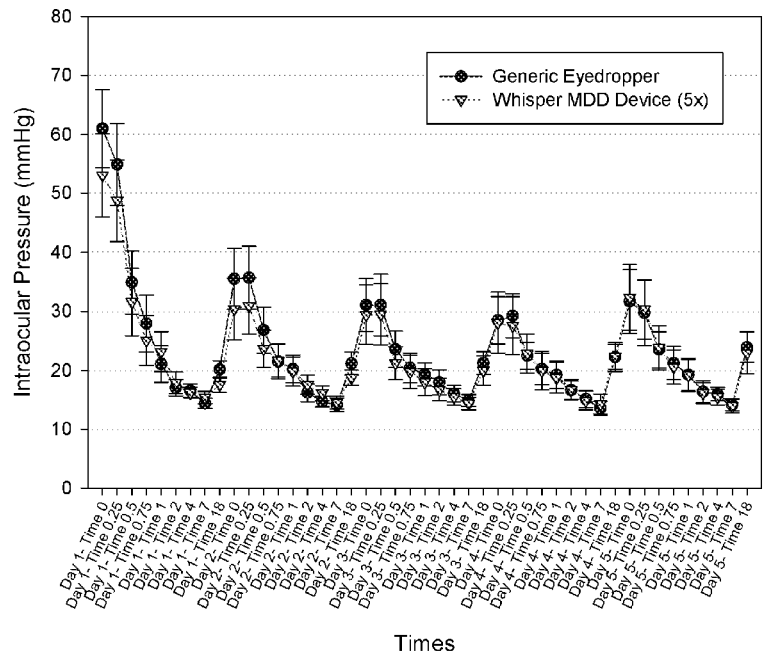
FIG. 24A illustrates intraocular pressure in animals treated with 6.0 µl of 0.025% (5×) latanoprost via a spray ejector device of the disclosure (Whisper MDD), compared to traditional eyedropper administration of 0.005% latanoprost (Eye Dropper).
Figure 24B:
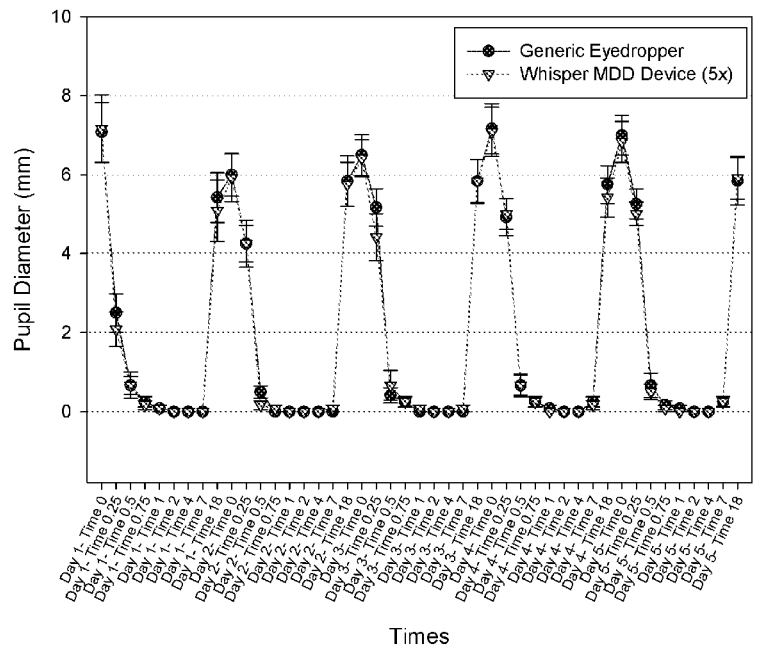
FIG. 24B illustrates pupil diameter in animals treated with 6.0 µl of 0.025% (5×) latanoprost via a spray ejector device of the disclosure (Whisper MDD), compared to traditional eyedropper administration of 0.005% latanoprost (Eye Dropper).

Both the spray ejector device (6.0 μl at 0.025%) and generic latanoprost (0.005%) eyedropper had similar results. There were no significant differences between intraocular pressure (IOP) ($p=0.823$) nor pupil diameter (PD) ($p=0.943$) at any point in this study. IOP decreased approximately 45.4 mmHg the first day of the study and 24.7 mmHg on subsequent days. PD decreased as predicted to pinpoint size (0 mm) by time 1 hour each day (FIGS. 24A and 24B). There were no abnormal or unexpected outcomes. Normal irritation caused by prostaglandin analogues was present.

Discussion

In summary, IOP and PD results for 0.025% latanoprost delivery via a spray ejector device at 6.0±0.6 μl are statistically equivalent to traditional delivery of 1 drop (approximately 26.0±10.0 μl) latanoprost once daily. Both treatments significantly lower IOP in the glaucomatous Beagle when instilled daily. Latanoprost delivered via spray ejector device in five times (5×) the concentration of that delivered by eyedropper resulted in no more irritation than that occurring following eyedropper administration. Use of equivalent doses in lower-volume, higher-concentration formulations delivered via a spray ejector device may improve therapeutic outcomes by allowing for lower preservative amounts per dose and reducing systemic toxicity due to less outflow into the pharynx.

Example 11

This example relates to a clinical study using glaucomatous beagles which evaluates the effects on intraocular pressure (IOP) of q12 h instillation (BID) of 12 µl of latanoprost by a spray ejector device, compared to once-daily instillation of an average of 26 µl via traditional eyedropper.

The current study instills a known effective dose of two 6 µl doses of 0.005% latanoprost, which is less than 50% of the dose volume delivered by traditional eyedropper. The 6 µl doses were administered q12 h by a spray device in a side-by-side randomized crossover comparison with once-daily, eyedropper-instilled 0.005% latanoprost in an attempt to decrease 24-hour fluctuations in IOP.

Materials and Methods

Four beagle dogs with differing levels of hereditary glaucoma were used. All animals were from an existing colony of glaucomatous beagles housed at the University of Florida.

Two males and two females aged 3-9 were selected for this study. All dogs weighed at least 5 kg. No acclimation or quarantine was necessary. Animals were identified by tattoo, microchip, and markings.

Ophthalmic examinations (slit lamp with fluorescein and indirect ophthalmoscopy) were performed on the eyes of each animal prior to study day 1. Ocular findings were scored according to the McDonald-Shadduck score system and macroscopic observations were recorded in accordance with the Draize scale for scoring ocular lesions. Ocular findings were recorded using a standardized data collection sheet.

The study used commercially available latanoprost (0.005%) instilled by a spray ejector device and by traditional eyedropper. The study eye was randomized Study animals received one dose via spray ejector device in the study eye and one drop via traditional eyedropper in the contralateral eye. Beginning on study day 1, baseline data were collected at time 0, 1, 2, 4, 7, and 12 hours for 5 days. On study day 7, the first dosing was administered at approximately 0900 h (study hour 0). A spray ejector device was used to deliver 6 µl into one randomly assigned study eye of each dog. After 5 seconds, a second 6 µl dose was given to the same eye. The contralateral eye (positive control) received one drop of generic 0.005% latanoprost via traditional eyedropper. Beginning at study hour 0 on study day 7, pupil diameter (PD), intraocular pressure (IOP), and heart rate (HR) were monitored daily at hours 0, 1, 2, 4, 7, and 12. Dosing was performed after the measurements at hours 0 and 12 each day. This procedure was repeated for 5 days. The study ended after the study hour 24 measurement.

Results

Baseline IOP, measured over 5 days, had a daily average of 48.4±1.16 mmHg. Baseline PD was 6.4±0.15 mm on average. There was no significant difference between morning and evening readings. Some trends in IOP indicated a slight diurnal effect, with lower pressures measured in the evening. Study day 7, time 0 measurements reflected the baseline data.

Figure 25A:
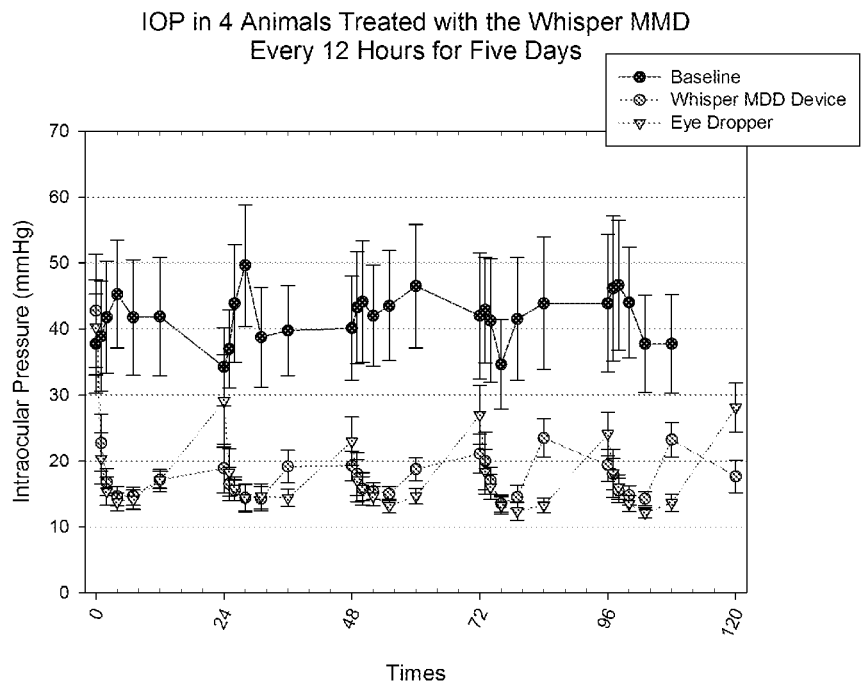
FIG. 25A illustrates intraocular pressure in animals treated with 12.0 µl of 0.005% latanoprost twic daily via a spray ejector device of the disclosure (Whisper MDD), compared to traditional eyedropper administration (Eye Dropper).

In eyes treated with a spray ejector device, IOP declined rapidly on study day 7, the first day of instillation, with a maximum decrease of 28 mmHg to a level of 15.5±2.2 mmHg at hour 7. On day 8, the maximum IOP was 17.2±3.0 mmHg, and the minimum was 13.6±1.2 mmHg at hour 7. On day 9, the maximum IOP was 26.2±6 3 mmHg, and the minimum 16.2±1.5 mmHg at hour 4. On day 10, the maximum IOP was 27.5±3 5 mmHg, and the minimum was 14.0±1.3 at hour 4. Day 11 was similar, with a maximum IOP of 26.5±2.8 mmHg and a minimum that day of 14.7±0.9 mmHg at hour 7 (FIG. 25A).

Eyes treated with the eyedropper also showed a decrease in IOP. These changes tracked published results, with a maximum decrease of 27.5 mmHg over the 5 days of the study. Daily maximum values were generally higher than in eyes treated with the spray ejector device. The average daily change for the eyedropper-treated eyes (maximum minus minimum) was 14.6 mmHg; for eyes treated using a spray ejector device, average daily change was 7.6 mmHg.

Figure 25B:
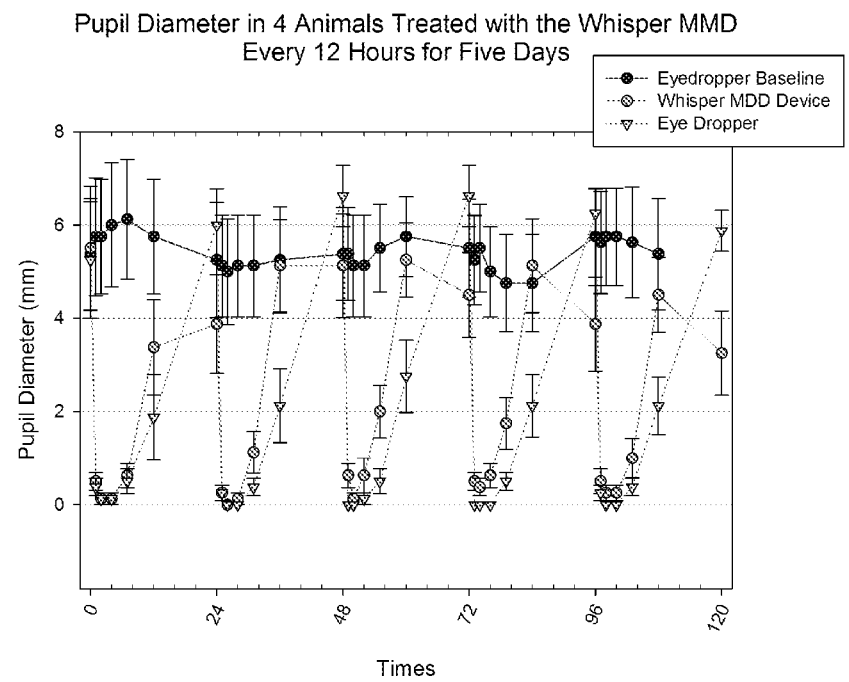
FIG. 25B illustrates pupil diamter in animals treated with 12.0 µl of 0.005% latanoprost twice daily via a spray ejector device of the disclosure (Whisper MDD), compared to traditional eyedropper administration (Eye Dropper).

PD changes were similar for both treatments: PD reached a minimum diameter (pinpoint) by time 1 hour on most days. Eyedropper-treated eyes returned to normal PD within 24 hours; in eyes treated using a spray ejector device, PD remained constricted much longer (FIG. 25B). There were no reported changes in heart rate. There were no significant reports of ocular irritation, injury, or discomfort with either treatment.

Discussion

In summary, 0.005% latanoprost delivery via a spray ejector device significantly lowered IOP in glaucomatous beagles when instilled BID. Twice-daily instillation of latanoprost resulted in fewer daily IOP fluctuations, while using less than 50% of the standard doses. Dosing with a spray ejector device consistently prevented the anticipated morning IOP spike as compared to eyedropper delivery.

The lower dosage was associated with less irritation to the eye often seen with heavy use of prostaglandin analogues. The average fluctuation in IOP was 7.6 mmHg (30%), representing a substantial reduction relative to once-daily dosing. PD remained low for a longer duration following spray ejector device delivery, as compared to that following eyedropper delivery of latanoprost.

A distinct trend is shown in this series of studies (Examples 1-11), illustrating that drugs delivered via a spray ejector device of the disclosure are effective in lower total doses, lower total dosage volumes, and higher dosage concentrations, with less ocular irritation.

Example 12

This example relates to a pharmacokinetic clinical study using glaucomatous beagles to compare the levels of acid of latanoprost in the aqueous humor (AH) following delivery of 9 µl of 0.005% latanoprost via a spray ejector device of the disclosure, as compared to delivery of an average of 26 µl of 0.005% latanoprost via traditional eyedropper.

Materials and Methods

Eight normal laboratory beagles were chosen for this study. Conditions for inclusion included normal overall health and normal ophthalmic state as determined by gross eye exam by a boarded veterinary ophthalmologist. Pre- and post-dosing mass deposition calibrations of the spray device were consistently within 10% of the intended dose of 9 µl. A 9.0 µl dose of a commercially available prostaglandin pro-drug, latanoprost, was instilled topically in two eyes of each of eight normotensive beagle dogs using the spray ejector device. Levels of the acid of latanoprost were measured in aqueous humor (AH) obtained by aqueocentesis over a 7-hour period each day for 5 days. This protocol was repeated for latanoprost 0.005% delivered by eyedropper (average dose 26 µl).

Part 1

All dogs received a washout and acclimation period of two weeks. In Week 1, all animals were assigned to a group, with two animals each in Groups 1, 2, 4, and 7. On study day 1, at hour 0 (±15 minutes) each animal received 9 µl of 0.005% latanoprost in each eye via the spray ejector device. At hour 1, two Group 1 dogs were sedated (Torbugesic®, 0.1 to 1 mg/kg) and given topical ocular anesthetic (Proparacaine Hydrochloride Ophthalmic Solution USP, 0.5%). IOP and PD were measured while the topical anesthetic took effect. Sedation protocol was modified using dexmedetomidine 1 mcg/kg with excellent results when anxiety and movement was noted, preventing researchers from obtaining four aliquots of AH for testing. Each eye was then gently cleansed with a 0.1% betadine solution. In each eye, a 27 g or 30 g needle was used to carefully collect a minimum of 50-75 µl of AH from the anterior chamber. Each sample was placed in a sterile 1.5 ml eppendorf tube, labeled, and stored first on dry ice and later in a −80° C. ultra-freezer. The needle puncture was held with direct pressure from a sterile swab. Topical antibiotics were applied to the eye as a final caution each day. This was repeated for each pair of grouped dogs at hours 2, 4, and 7 (16 samples per day for 5 days). A total of 76 AH samples were collected over a 5-day period. Week 2 was used as a washout and healing week for the animals.

Part 2

Week 3 followed the Week 1 protocol, with the substitution of eyedropper-delivered 0.005% latanoprost at an average dose of 26 µl at time 0. A total of 74 AH samples were collected in 80 aqueocentesis attempts over a period of 5 days. All AH samples were frozen to −80° C., stored overnight on dry ice, and then analyzed for the acid of latanoprost using a latanoprost-specific HPLC methodology. At the conclusion of the study, the animals were physically examined and prepared for adoption or other uses as deemed appropriate.

Results

Part 1

Following dosing with 9 µl of 0.005% latanoprost delivered by the spray ejector device, AH samples taken at 1, 2, 4, and 7 hours were found to have acid of latanoprost levels of 0.43±0.11 µg/ml, 0.54±0.10 µg/ml, 0.28±0.08 µg/ml, and 0.30±0.06 µg/ml, respectively (Table 2).

TABLE 2

Average levels of acid of latanoprost in the AH after instillation of 9 µl of 0.005% latanoprost via a spray ejector device of the disclosure

| Hour | Average level (µg/ml) | Std. Dev. |
|---|---|---|
| 1 | 0.4329529 | 0.1064908 |
| 2 | 0.5371379 | 0.1026815 |
| 4 | 0.2790276 | 0.0811741 |
| 7 | 0.3043631 | 0.0645884 |

Part 2

Following administration of an average dosage of 26 µl of 0.005% latanoprost delivered by eyedropper, AH samples taken at 1, 2, 4, and 7 hours were found to have acid of latanoprost levels of 0.50±0.14 µg/ml, 0.15±0.03 µg/ml, 0.28±0.09 µg/ml, and 0.27±0.04 µg/ml, respectively (Table 3).

TABLE 3

Average levels of acid of latanoprost in the AH after instillation of an average of 26 µl of 0.005% latanoprost via traditional eyedropper.

| Hour | Average level (µg/ml) | Std. Dev. |
|---|---|---|
| 1 | 0.4974834 | 0.1433618 |
| 2 | 0.1543346 | 0.0270988 |
| 4 | 0.2811312 | 0.0912668 |
| 7 | 0.2654899 | 0.0402795 |

Figure 26A:
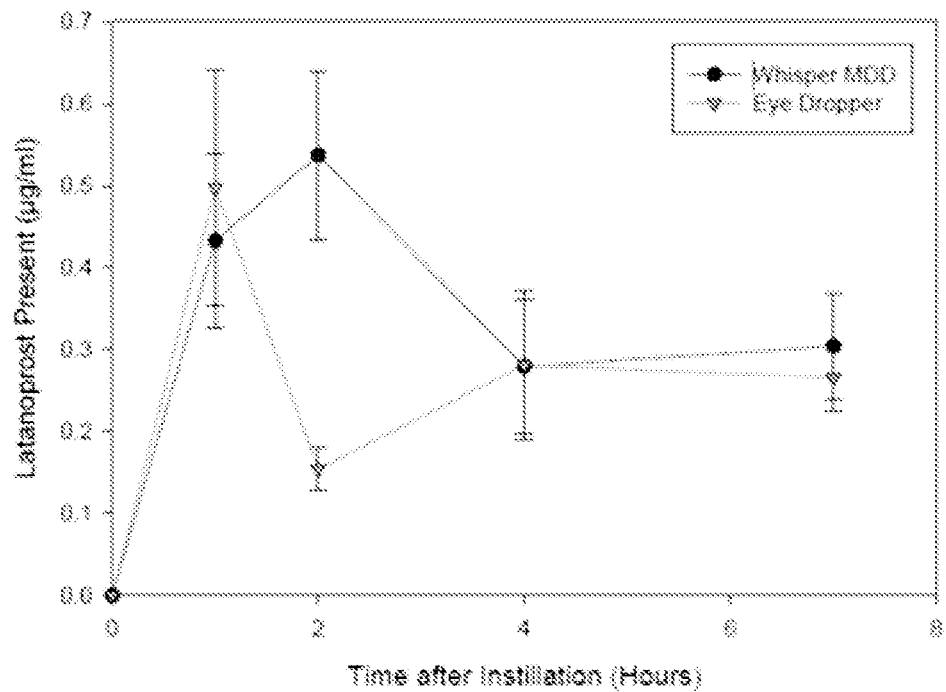
FIG. 26A illustrates weekly average levels of acid of latanoprost present in the AH after administration of 9.0 µl of 0.005% latanoprost via a spray ejector device of the disclosure (Whisper MDD), compared to traditional eyedropper administration (Eye Dropper).
Figure 26B:
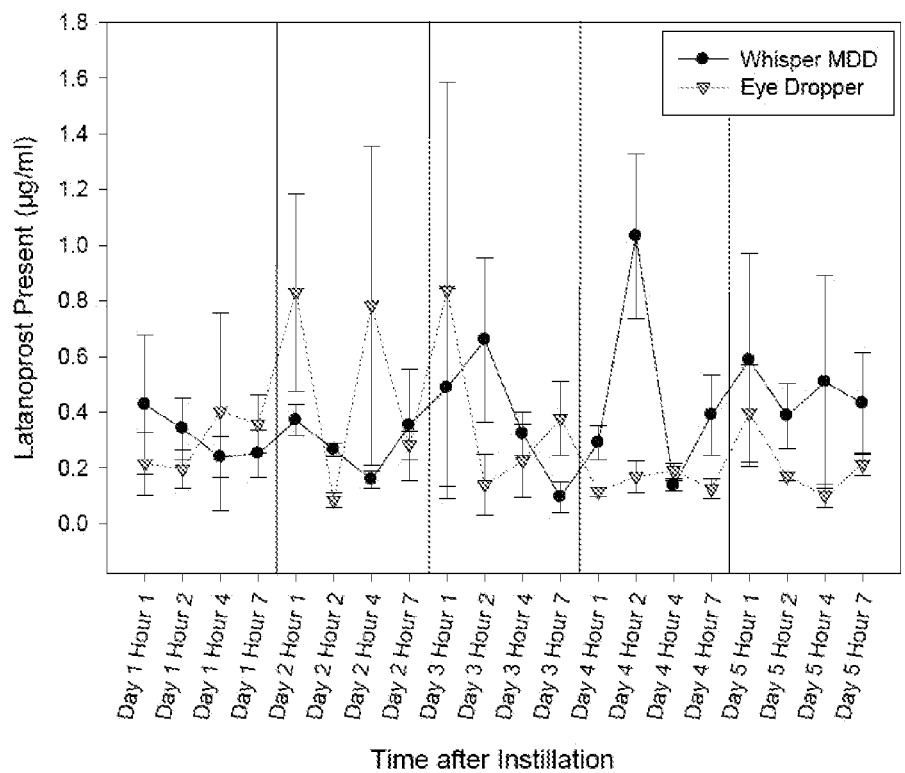
FIG. 26B illustrates latanoprost present in the AH after administration of 9.0 µl of 0.005% latanoprost twice daily via a spray ejector device of the disclosure (Whisper MDD), compared to traditional eyedropper administration (Eye Dropper).

Weekly and daily average levels of acid of latanoprost for parts 1 and 2 of the study are shown in FIGS. 26A and 26B. A mathematical analysis of FIG. 26A (Table 4) highlights the greater maximum concentration (CMAX) and area under the curve (AUC) for the pharmacologically active acid of latanoprost levels following dosing via the spray ejector device.

TABLE 4

Mathematical analysis of FIG. 26A

| Whisper™ MDD | Tmax | 2 hours | Total area under the curve (hours* µg/ml) | 2.392773 |
|---|---|---|---|---|
| | Cmax | 0.5371379 µg/ml | | |
| Eyedropper Bottle | Tmax | 1 hour | Total area under the curve (hours* µg/ml) | 1.830043 |
| | Cmax | 0.4974834 µg/ml | | |
| | | | Area Difference: | 0.56273 |

Discussion

After 1 hour, the level of acid of latanoprost in AH is higher following the delivery of 26 µl latanoprost by eyedropper than after delivery of 9 µl of latanoprost by a spray ejector device of the disclosure. At hour 2 the acid of latanoprost level in eyes receiving the latanoprost delivered by the spray ejector device rose by more than 25%, while the level in eyes treated by eyedropper decreased by more than 80%. At hours 4 and 7, the amount of acid of latanoprost delivered by the spray ejector device leveled out at 50% of its initial level, and eyedropper-delivered latanoprost in its acid form leveled out at approximately 40%. IOP reduction and decrease in PD were comparable for both delivery methods (9 µl delivered by the spray ejector device and 26 µl delivered by eyedropper) over the 7-hour study period in the companion study of Example 4.

The results of this study suggest that passive diffusion, osmosis, and active transport are occurring with both delivery systems, and that the prostaglandin pro-drug delivered by the spray ejector device is absorbed at a higher (three-fold) rate and has a longer duration than eyedropper-delivered drug in higher doses. Droplet size, droplet momentum, volume of dose, and other factors appear to influence the pharmacokinetics and the IOP- and PD-decreasing effects of the sprayed prostaglandin pro-drug latanoprost.

Example 13

This example evaluates the charging of an ejector surface and fluid loading of a charge isolated spray ejector device of the disclosure.

Figure 14A:
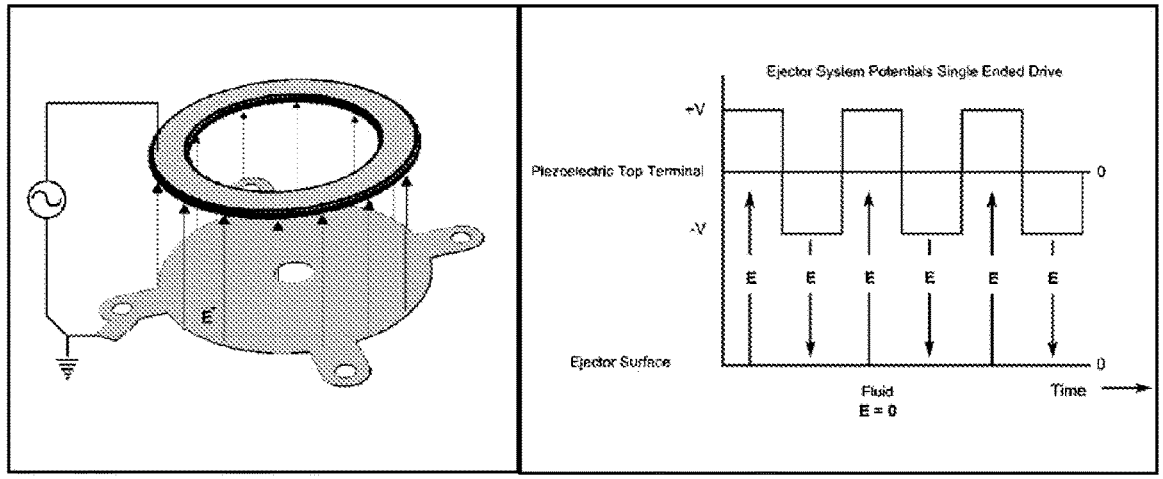
FIGS. 14A-14C illustrate alternative implementations of ejector mechanisms, ejector system drive signals and associated electric fields according to certain aspects of the disclosure. 14A: a single ended drive applied only to the top terminal of a piezoelectric with the ejector surface grounded and drive signals and associated fields; 14B: a differentially driven ejector system where both the piezoelectric and the ejector surface are alternatively driven by a voltage while the other electrode is grounded and drive signals and associated fields; 14 C: a charge isolated implementation having an added third conductor and dielectric and drive signals and associated fields.
Figure 14B:
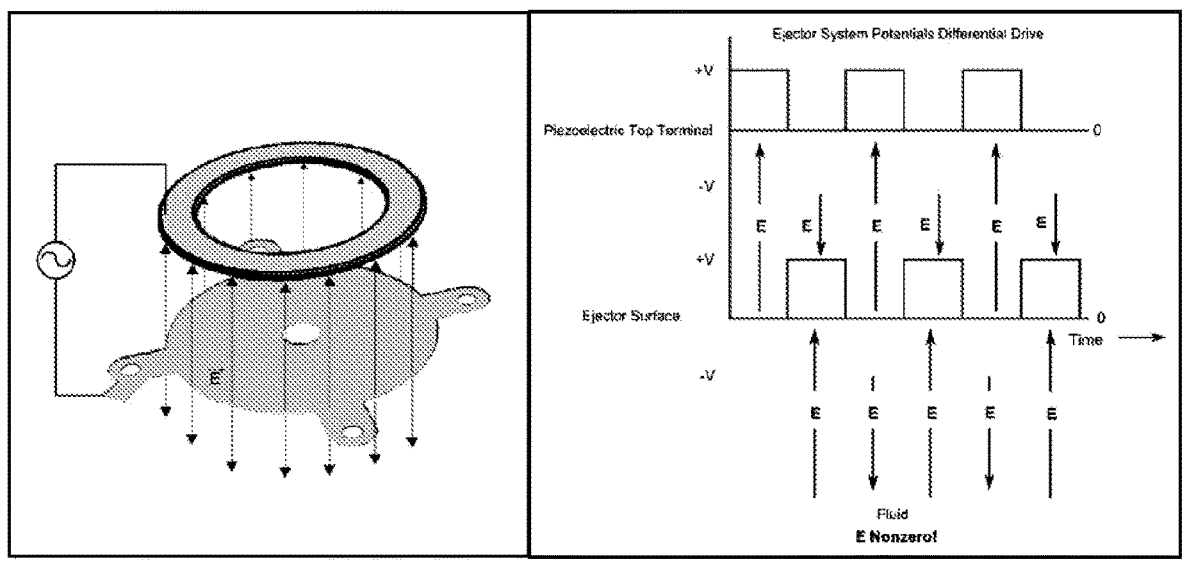
Figure 14C:
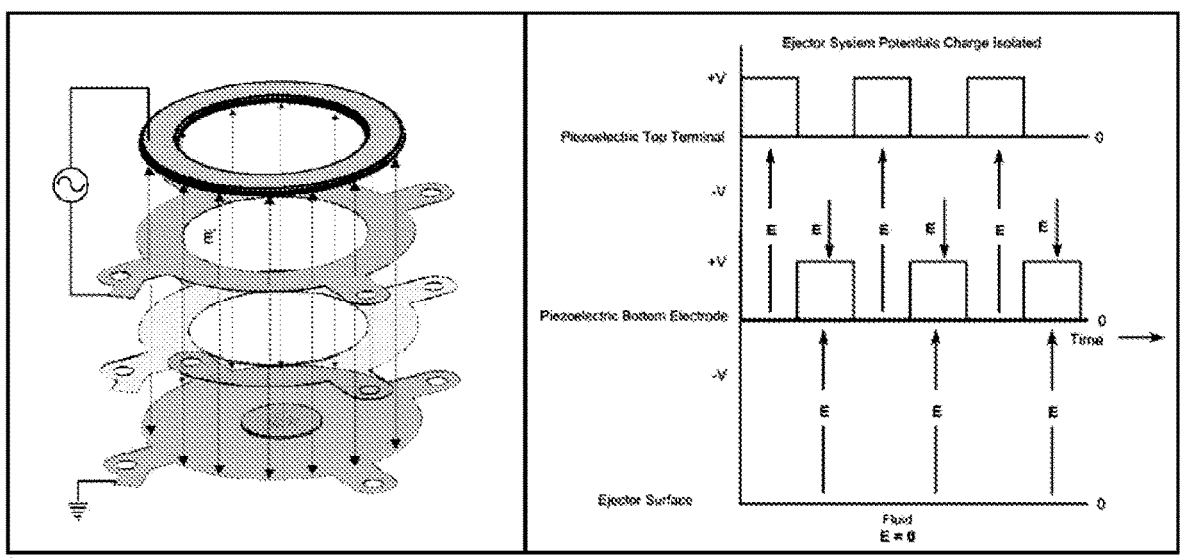

With reference to FIG. 14A-14C, ejector system signals on each conducting surface for 14A: a single ended drive applied only to the top terminal of a piezoelectric with the ejector surface grounded, 14B: a differentially driven ejector system where both the piezoelectric and the ejector surface are alternatively driven by a voltage while the other electrode is grounded, and 14C: where a third conductor and dielectric are added to drive the piezoelectric differentially while grounding the ejector surface.

A standard piezoelectric ejector topology is shown in FIGS. 14A-14B, where a piezoelectric is bonded to an ejector plate that may be a hybrid ejector or a single membrane with ejector nozzles. In the device in FIG. 14A: a standard piezoelectric ejector topology is shown where the ejector surface remains grounded. The other electrode of the piezoelectric is driven by a single ended electrical signal, i.e. it oscillates with equal and opposite polarity with respect to the ground electrode. Due to the constant potential of the ejector surface, which is grounded, no voltage is applied to the fluid and the electric field in the fluid is or nearly is zero.

Figure 27A:
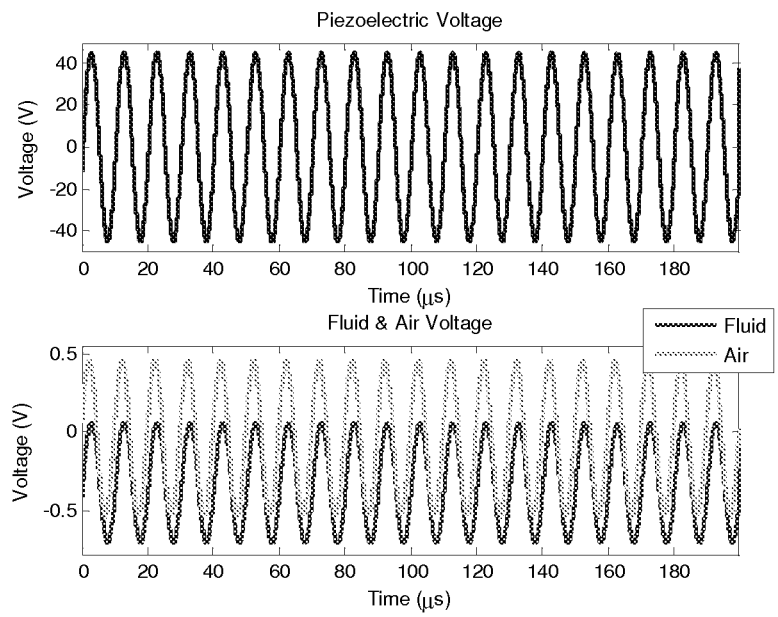
FIG. 27A shows a plot of single ended drive waveforms measured for an implementation of an ejector system of FIG. 14A showing a small periodic voltage in the fluid resulting from current flow through the oscillating plate.
Figure 27B:
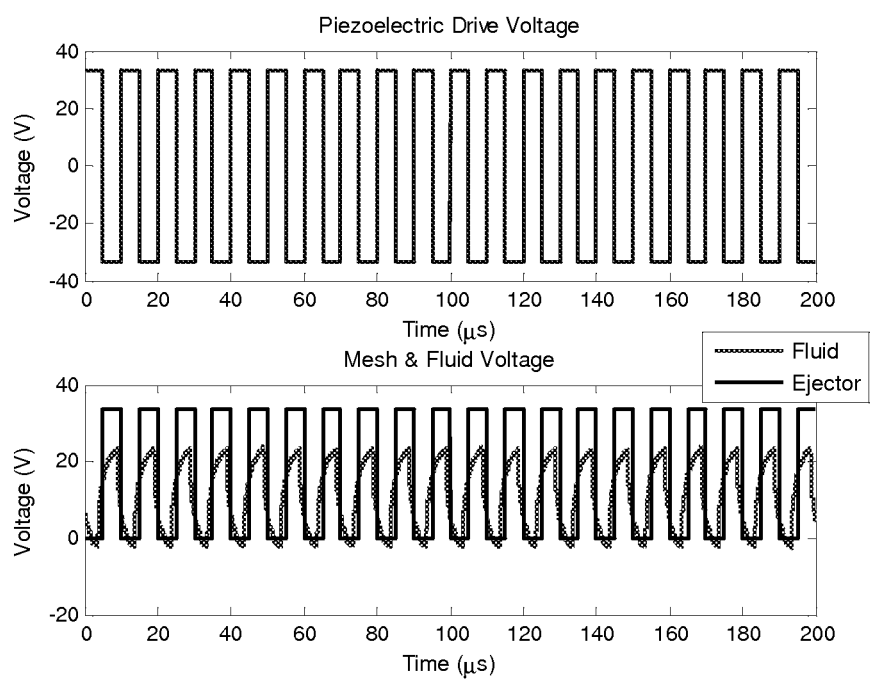
FIG. 27B shows a plot of single ended drive waveforms measured for an implementation of an ejector system of FIG. 14B showing a large periodic voltage in the fluid due to the direct contact with the alternating potential of the oscillating plate.

FIG. 27A shows single ended drive waveforms measured in the lab for the ejector system of FIG. 14A. A small periodic voltage develops in the fluid due to the current flow through the ejector plate. The voltage developed in the fluid (distilled water) is lower than the voltage induced on an infinitely small dipole by the Electric field locally around the fluid reservoir (directly on top) and orders of magnitude smaller than the signal applied to the piezoelectric. FIG. 27B shows that while the ejector plate is grounded, a finite voltage still develops on the ejector plate due to resistive losses when current flows through the plate to ground. The fluid thus experiences a small voltage fluctuation lower than the voltage induced on an infinitely small dipole by the local Electric field around the fluid reservoir and approximately two orders of magnitude below the piezoelectric drive signal.

In the device in FIG. 14B, a standard piezoelectric ejector topology is shown where the ejector surface and the piezoelectric electrode are driven differentially, i.e. with equal signals offset by a half period. While one electrode is driven, the other electrode is either grounded equal and opposite polarity. No part of the ejector system is directly grounded in this system. Voltages on each electrode are referenced to the power supply ground and fields form between the varying potentials of the two electrodes, exciting the piezoelectric. Due to the varying potential of the ejector surface, which is not grounded, a voltage is periodically applied to the fluid corresponding to the ejector electrode and an alternating polarity electric field exists in the fluid which is extremely large amplitude relative to the driving signal. An actual laboratory measurement of this configuration with distilled water shows that under differential drive, the fluid acts as a capacitor which stores energy and returns it back to the ejector surface. This induces current flow in the fluid which extremely harmful for fluids with electrolytic properties, as the current flow increases for these fluids.

FIG. 27B shows a differential drive waveforms measured in the lab for the ejector system of FIG. 14B. A large periodic voltage develops in the fluid due to the direct contact with the alternating potential of the ejector plate. The fluid charges and discharges periodically similar to a capacitor following the ejector surface potential. Electrolytic fluids are more similar to resistors and will follow the waveform directly.

Contrary to this, in accordance with the present disclosure, in the device of FIG. 14C, a charge isolated ejector topology is shown where the ejector surface remains grounded while the piezoelectric element is driven differentially. The electric field is largely confined between the differentially driven electrodes in the case of opposite polarity, equal amplitude signals on each electrode. The ejector surface remains grounded. In the case of alternating same polarity signals, as shown in FIG. 14C the electric field at the ejector surface is zero when the piezoelectric electrode is driven and one fourth of the single ended case of FIG. 14A (half voltage of single ended drive on that electrode and field split by ½, ½ goes to piezoelectric electrode and other ½ goes to ejector surface). The result of this configuration is near perfect field screening with respect to the fluid when both electrodes are driven with equal and opposite polarity signals. When both electrodes are driven time offset with alternating ground and positive polarity signals, as shown in FIG. 14C, lab measurements, shown in FIG. 27C, demonstrate that less than one half the voltage seen in the single ended case of FIG. 27B and over two orders of magnitude less than the piezoelectric signal. For true differential drive, the voltage imparted into the fluid would be further reduced an order of magnitude or more.

Figure 27C:
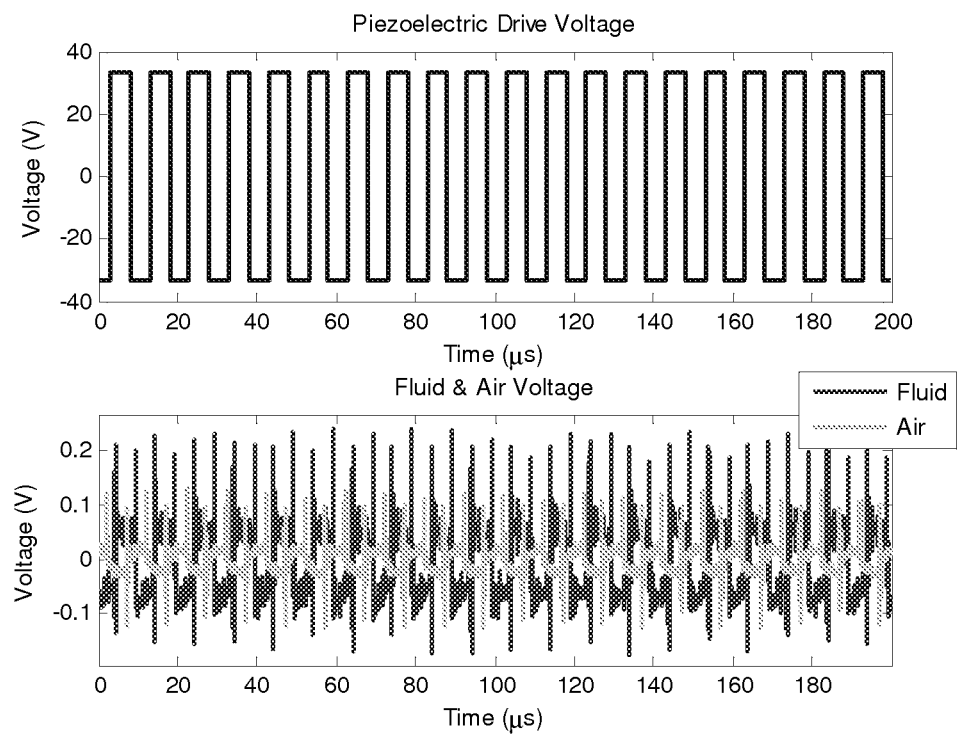
FIG. 27C shows a plot of single ended drive waveforms measured for an implementation of an ejector system of FIG. 14C showing a small periodic voltage in the fluid due to the current flow through the oscillating plate that is one half or less the level of the standard system of FIG. 14A.

FIG. 27C shows a charge isolated ejector waveforms measured in the lab for the ejector system of FIG. 14C in accordance with an embodiment of the present disclosure. A small periodic voltage develops in the fluid due to the current flow through the ejector plate that is one half or less the level of the standard system of FIG. 14A. The voltage developed in the air shows how well the system screens the electric field produced by standard systems near the fluid reservoir.

Figure 28:
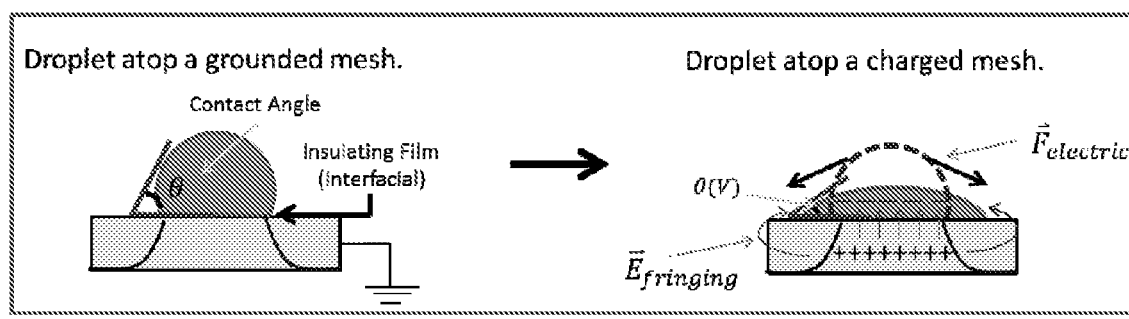
FIG. 28 illustrates a droplet experiencing electro-wetting while oscillating in an opening of a charged oscillating plate according to an embodiment of the present disclosure.
Figure 31:
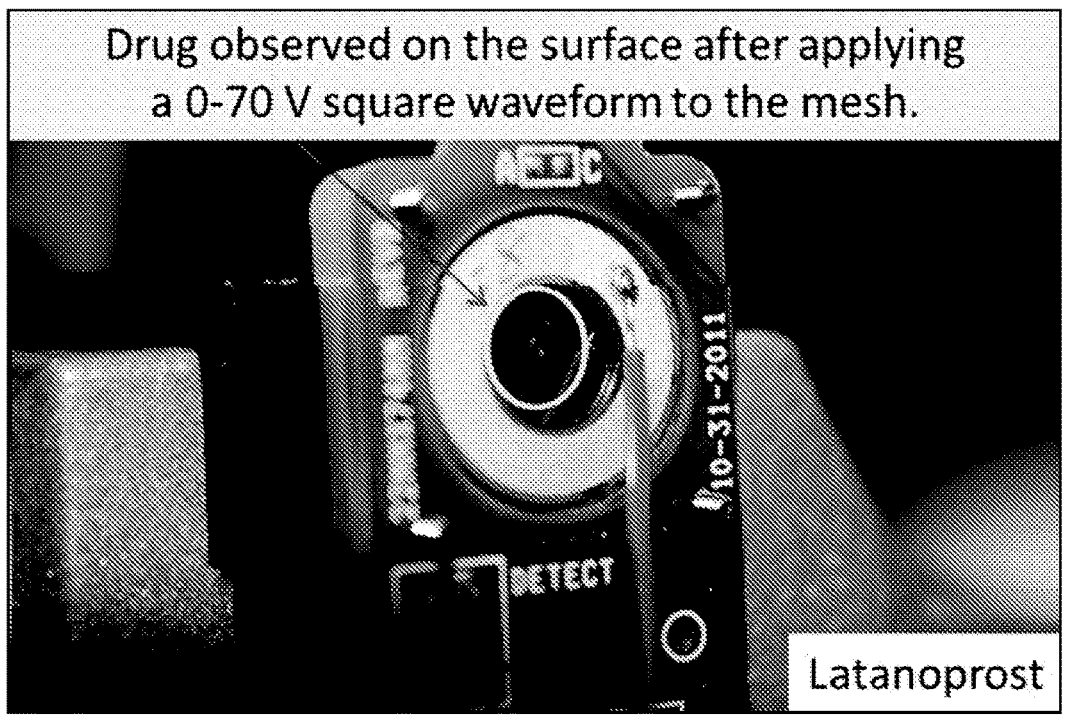
FIG. 31 shows an image of the surface of an ejector after applying a square waveform according to an implementation of an ejector of FIG. 14A with a fluid having the drug latanoprost.
Figure 32:
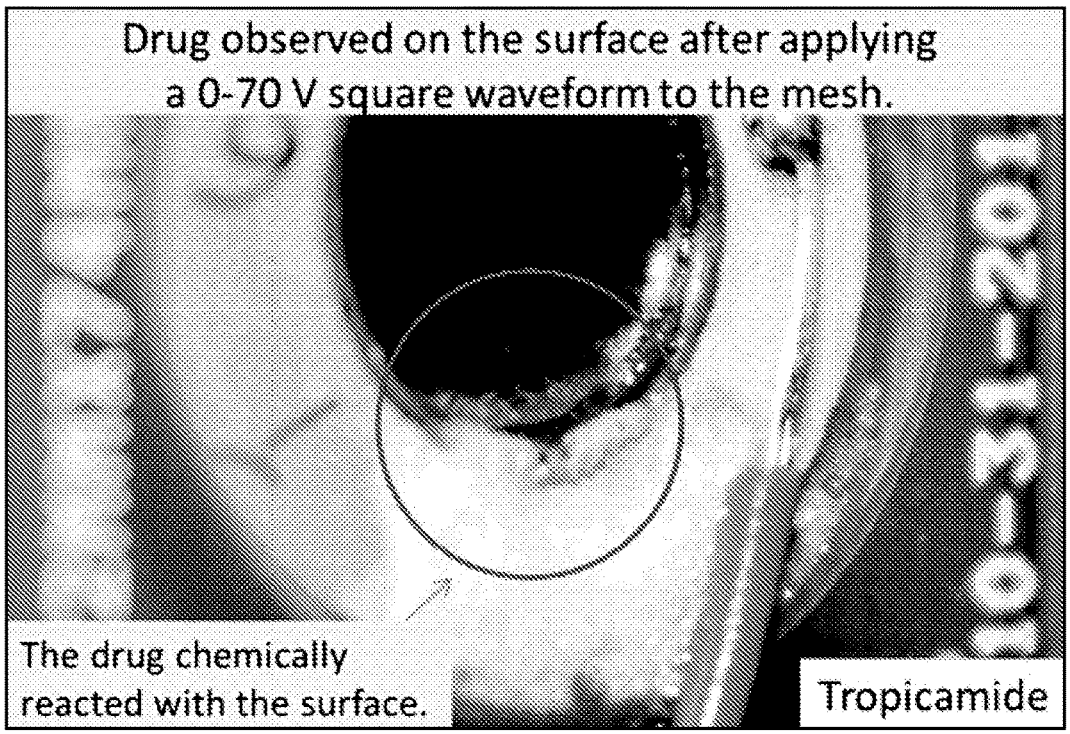
FIG. 32 shows an image of the surface of an ejector after applying a square waveform according to an implementation of an ejector of FIG. 14A with a fluid having the drug tropicamide.

The fluid in contact with the ejector alternately charges and discharges while in its containment reservoir. This charging and discharging can catalyze corrosive reactions for unpassivated, conducting surfaces. Upon oscillation in an ejection hole, the charge of the ejector can reverse polarity with respect to the fluid, causing electric fields from the drop to the ejector surface which result in electromotive force pulling the fluid onto the ejector surface (electro-wetting). After electro-wetting has formed a fluid bead on the surface of the ejector, the process can continue pumping non ejected fluid toward the surface which interferes with subsequent ejected droplets. Vibration of the mesh in a spraying mode only enhances this problem. FIG. 28 demonstrates the process of electro-wetting.

When a voltage (V) is applied between the substrate and the fluid the contact angle θ decreases (to a certain critical or "saturated" value) according to the following relationship.

$$\cos\theta(V) = \cos\theta(0) + \frac{\varepsilon_0 \varepsilon}{2t\gamma} V^2$$

In the equation above $\varepsilon$, $\varepsilon_\theta$, are the permittivity of the insulating film at the interface between the fluid and conducting substrate and the permittivity of free space respectively. The thickness of the insulating film is represented by t, the term γ is the surface tension of the fluid. Fringing electric field lines toward the edge of the droplet force the fluid closer to the surface (contact angle θ decreases as a function of applied voltage) which increases the area of the droplet in contact with the substrate. This phenomenon is called electro-wetting. When a drug electrowets the surface of the mesh a film is left over after the bulk of the leaked drug has evaporated that degrades and/or prevents fluid ejection.

Example 14

This example evaluates the mass deposition achieved by a charge-isolated ejector mechanism of the disclosure. To measure the mass deposition of an ejector device, an ejector device is clamped in a testing apparatus, a ground wire and positive wire of the device is connected to an operational amplifier and a current probe and voltage probe are connected to an oscilloscope. The frequency and voltage are set, for example, to a 90V peak to peak (90Vpp) sine wave at a frequency of 50 kilohertz (kHz) and the spray from the ejector device is measured 5 times on a 24 mm×60 mm No. 1 glass coverslip using a scale with a 1 milligram (mg) sensitivity and calibrated with a 1 mg class 1 weight with traceable certificate. For each measurement, the coverslip is placed on the scale and the scale is zeroed. The slide is placed in the spray path of the ejector device and the voltage applied for a predetermined time. The slide is returned to the scale and the mass is determined and recorded. The coverslip is cleaned, the scale re-zeroed before each measurement. A total of 5 measurements are recorded for each frequency. The process is repeated with the frequency incrementally changed based on a predetermined step size (normally 1 kHz).

The mass deposition profile of a charge isolated ejector device was determined. The results are presented in FIG. 29 which shows excellent performance. With a charge isolated ejector mechanism configured as illustrated in FIG. 14C, the ejector surface is always grounded, preventing charging effects and electro-wetting induced beading while still allowing the electrical benefits of differential signaling.

Example 15

This example evaluates the electro-wetting and corrosion of the surface of a charge isolated ejector mechanism of the disclosure. To examine electro-wetting of a charge isolated ejector mechanism by an oscillating electric field, an ejector device is set up according to FIG. 14C with either the ejector plate or the piezoelectric actuator grounded. In the experiments, the fluid is either distilled water (nonconductive) or water with salt added to make it conductive. To uncouple effects due to electro-wetting from injection induced droplet formation, the ejector device is driven at a frequency of 1 kHz that is a non-ejection frequency.

In a first experiment, an ejector surface is grounded and the piezoelectric actuator is driven by a 0 to 70V square wave form. There is no change observed either with distilled water or salt water because the fluid does not experience any electric field because the ejector plate surface is held at a constant potential of zero (ground).

In a second experiment, a piezoelectric actuator is grounded and the ejector surface is driven by a 0 to 70V square wave form. The ejector surface is driven with a 0 to 70V square waveform with the piezoelectric actuator tied to ground to ensure that the fluid behind the ejector surface sees an electric field similar to the one applied under actual operating conditions. When the fluid is distilled water, there are no observed changes as the distilled water is non-conducting, In a third experiment, a piezoelectric actuator is grounded and the ejector plate 1602 is driven by a 0 to 70V square wave form as in experiment two above, but the distilled water is exchanged with salt water. As shown in FIGS. 30A-30C, changes are observed almost immediately (Compare initial image FIG. 30A to intermediate image FIG. 30B) where a droplet of liquid begins to form. As the experiment continues, a chemical reaction becomes evident as seen in FIG. 30C.

To assess the potential electro-wetting and corrosive effects of a pharmaceutical solutions on an charge isolated ejector mechanism, the experiments are repeated using exemplary pharmaceutical solutions rather than water/saltwater. The pharmaceutical solutions include various salts, and may be partially acidic, which makes them similar to saltwater.

In an experiment, the fluid comprises the pharmaceutical, latanoprost. The ejector surface is driven by a 0 to 70V square wave form and the piezoelectric actuator is grounded as described above. After 2 minutes, the fluid containing latanoprost can be observed on the surface of the ejector plate as shown in FIG. 31.

In another experiment, fluid comprises the pharmaceutical active agent, tropicamide. The ejector surface is driven by a 0 to 70V square wave form and the piezoelectric actuator is grounded as described above. After 2 minutes, the fluid containing tropicamide can be observed on the surface of the ejector plate and the drug reacts chemically with the surface of the ejector plate as shown in FIG. 32.

Example 16

This example evaluates the charging of droplets ejected via a spray ejector mechanism.

Materials and Methods

All measurements were made using a faraday cup housed in a faraday cage connected to an electrometer with devices ejecting saline or other test fluid. All ejection surfaces were set 1-2 cm above the faraday cup. Charge measurements were normalized to ejection mass to account for mass differences in ejection methods. When necessary, ground surfaces were arranged above and below the ejector mechanism.

The faraday cup output is connected to the electrometer input while the electrometer ground is referenced to a common ground rail. The faraday cage is also referenced to common ground throughout the experiment. A conductive tube is placed on top of the faraday cage to increase the signal to noise ratio by limiting electrical interference that is received inside the faraday cage. The dual sides of the DC power supply are connected in series to facilitate voltages up to 125V DC. A resistor is placed at the output of the power supply as a safety measure. The lab stand is arranged to hold the mechanical sprayer at a set height of 11 mm above the faraday cage. The ejector plate of the ejector mechanism serves as an electrode to inductively charge the reservoir. The electrode is connected to either polarity of the power supply while the opposite polarity is connected to common ground. This allows the formation of an electric field in the space between the electrode and the faraday cage.

The electrometer is warmed up and zeroed, meanwhile the selected ejector is mounted to the mechanical sprayer and reservoir filled with saline (or other test fluid). The average mass per drop from the ejector is measured and recorded. A baseline is taken from the floating reservoir, then a grounded reservoir with the electrometer zeroed after each measurement. For the inductive charging analysis, once the baseline has been taken the electrode is connected to the power supply and measurements are taken from 25V to 125V in 25V steps from each polarity. The procedure is repeated for each ejector assembly. To suppress the effects of tribocharging, velocity was reduced to near zero by forcing fluid through mesh holes using a syringe. Droplet velocity was as close to zero as possible.

For the tribocharging analysis, the faraday cup is tied to the same potential as the ejector surface. The ejector surface is swept in potential from −125V to +125V to determine tribocharge effects.

Results and Discussion

As shown, in accordance with aspects of the disclosure, inductive charging of droplets is controllable and repeatable, with charge polarity and amplitude being controllable. Several configurations of ejector mechanisms of the disclosure were evaluated in this regard.

For instance, certain configurations comprise a hybrid ejector mechanism with a generator plate mounted on top of stainless steel ejector plate. In certain embodiments, the stainless steel ejector plate is passivated with a diamond-like coating (DLC) on the side that is in contact with fluid. In certain embodiments, the generator plate is mounted on the DLC passivated side of the ejector plate, which for this case would be the fluid. In other configurations, the generator plate is mounted opposite the DLC/fluid side. Certain embodiments include PEEK generator plates, while others include passivated plated NiCo generator plates. The configurations may include various combinations of non-passivated or DLC stainless steel ejector plates, PEEK or gold passivated NiCo generator plate, and fluid or non-fluid side mounting of the generator plate, etc. Other embodiments include a non-hybrid ejector mechanism comprising a generator plate including perforations in monolithic PEEK or "PIMP". PIMP configurations are may be set as a 4-post mounted, full piece of PEEK either "virgin" or talc filled with an ejector hole pattern drilled in the center.

In certain configurations, the ejector mechanism may be "shielded", in that the stainless steel ejector plate is held at ground (0) potential. In non-hybrid configurations, a stainless steel ring is mounted on top of the PIMP ejector and held at ground (0) potential. In this configuration, the stainless steel ring is used because PEEK is an insulating material, and draining charge from it would be difficult. The shielded configurations were useful to test the tribocharging effects of the generator plate alone.

In certain configuration, the placement of charging electrodes is also varied. In one configuration, the annulus (ejector plate) is held at a high/hot or positive potential and the flex circuit attached to the retainer plate (retainer flex) is held to ground ("AHFG"). Other configurations are the reverse of AHFG, in that the annulus (ejector plate) is held to ground and the retainer flex is held at a hot potential ("AGFH").

Figure 33A:
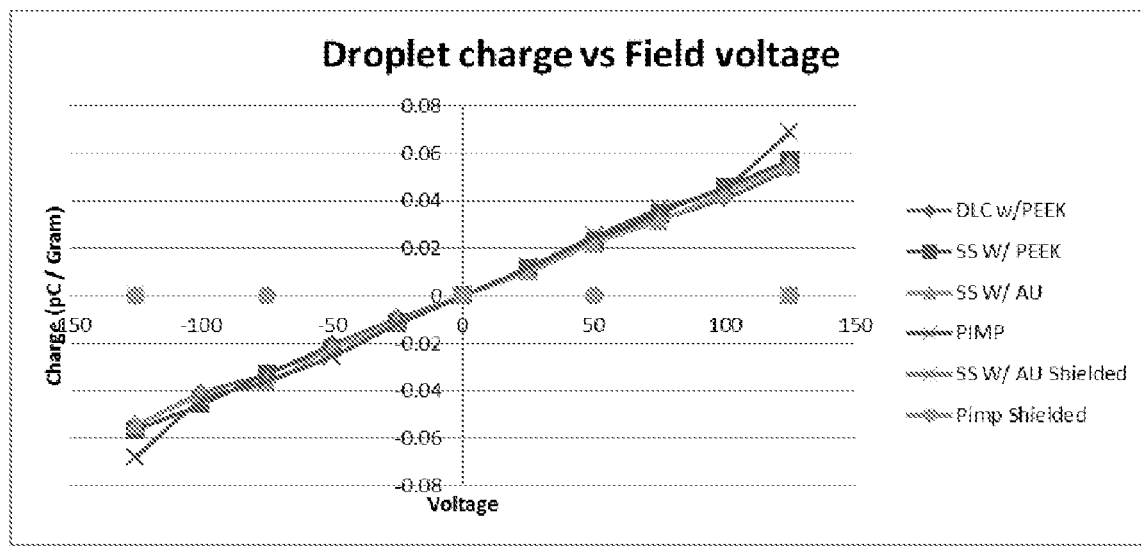
FIGS. 33A-33I illustrate controllable droplet charging according to certain aspects of the disclosure.
Figure 33B:
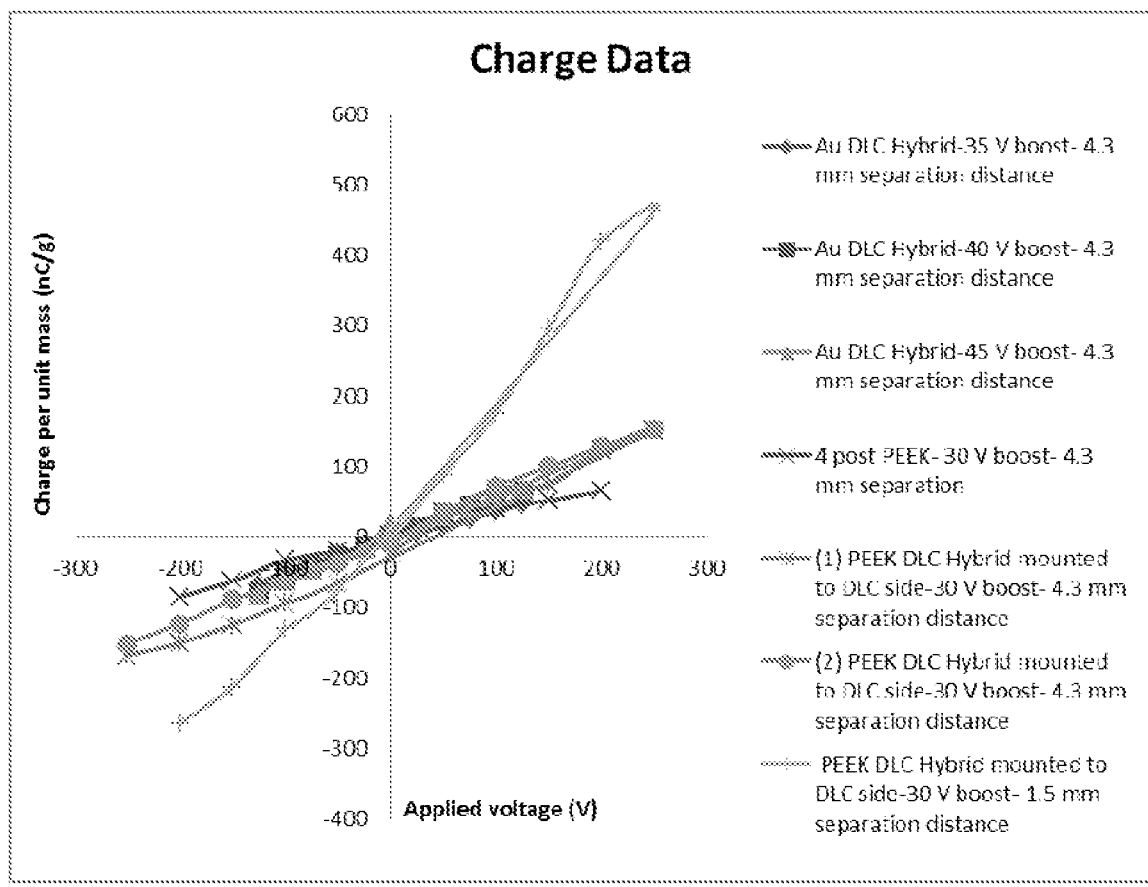
Figure 33C:
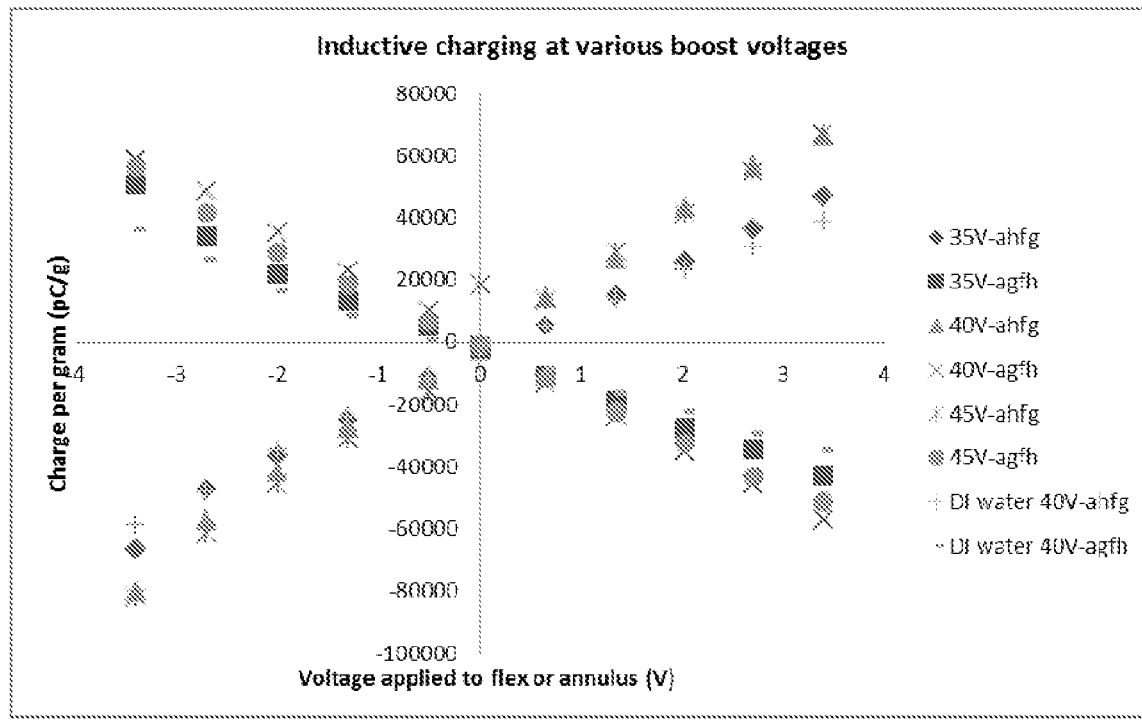

FIGS. 33A-33C show the charge imparted in pico-Coulombs per gram versus the applied voltage to the ejector surface. For each ejector mechanism tested (descriptions above), a linear relationship is shown between applied potential and measured charge on the droplets. Notably, when the ejector surface is kept at the same potential as the exterior electrode, no electric field is present and no measurable charge is imparted to the droplets.

Figure 33D:
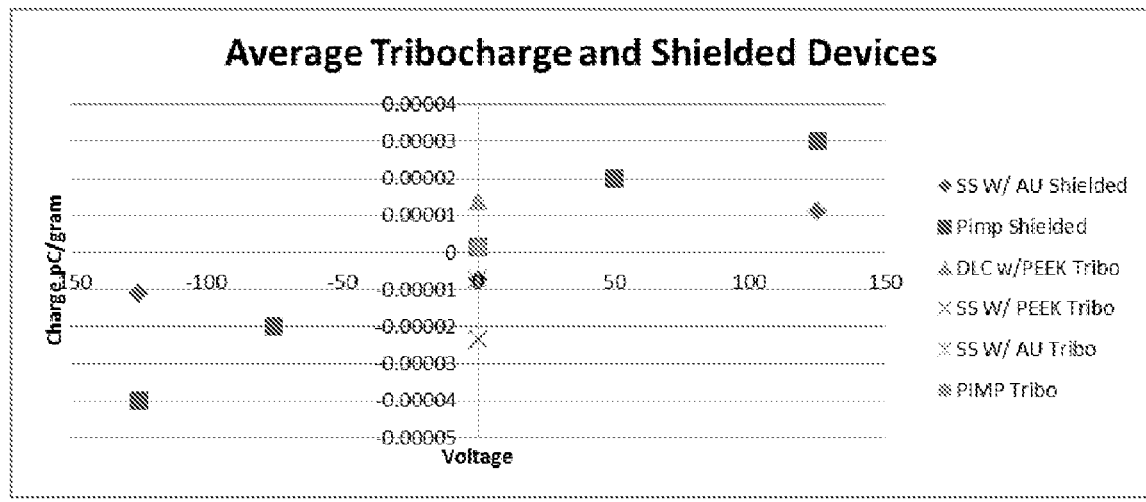

FIG. 33D illustrates the charge imparted via tribocharging with near zero velocity ejection for various ejector mechanism configurations (described above). As shown, the imparted tribocharge is at least 3 orders of magnitude lower than inductive charging.

Figure 33E:
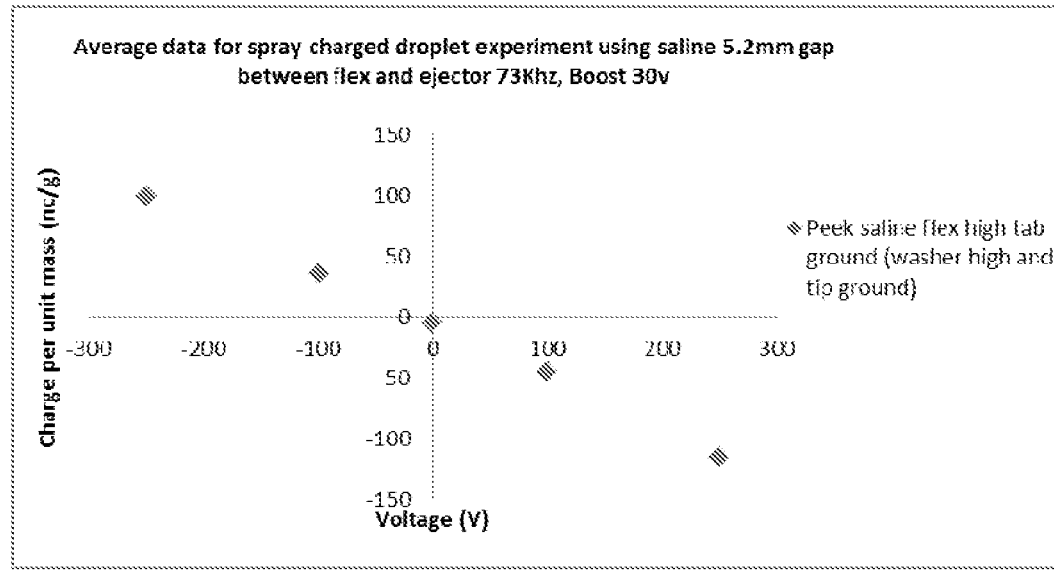
Figure 33F:
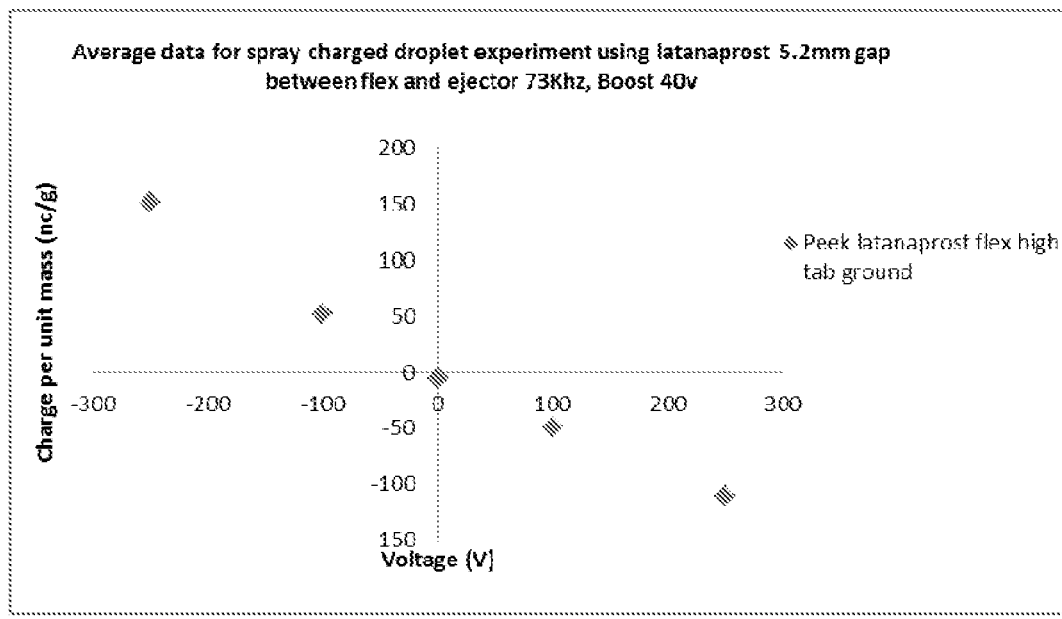
Figure 33G:
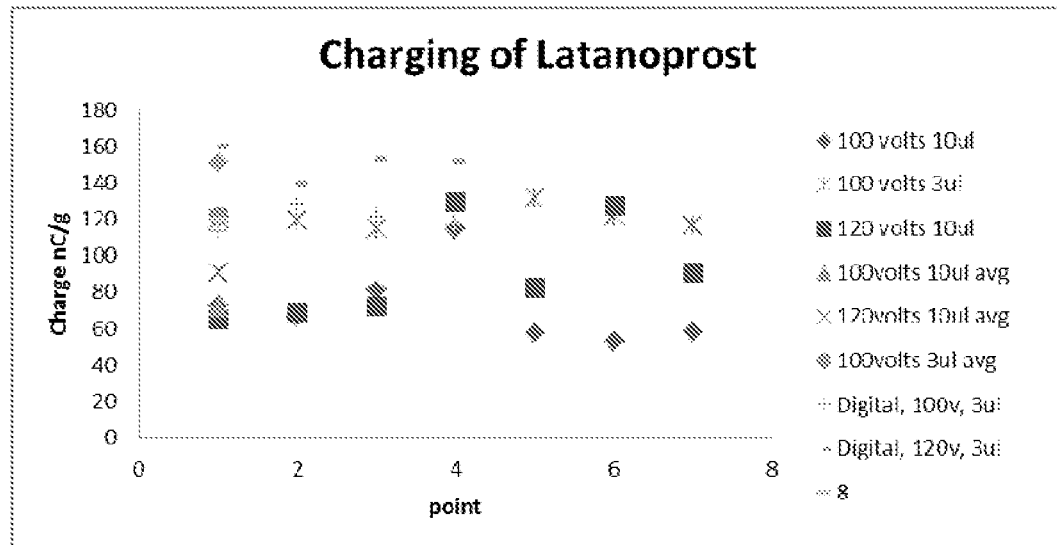

FIGS. 33E-33G illustrate charging of both saline and a representative ocular medication, latanoprost, establishing that controllable inductive charging of droplets may be achieved for a variety of representative fluids.

Figure 33H:
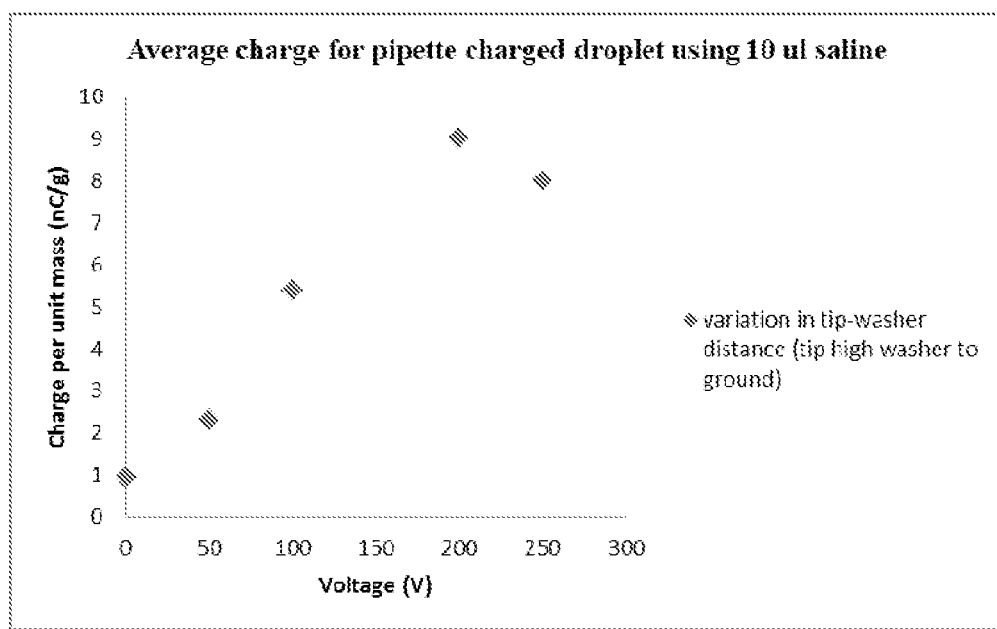
Figure 33I:
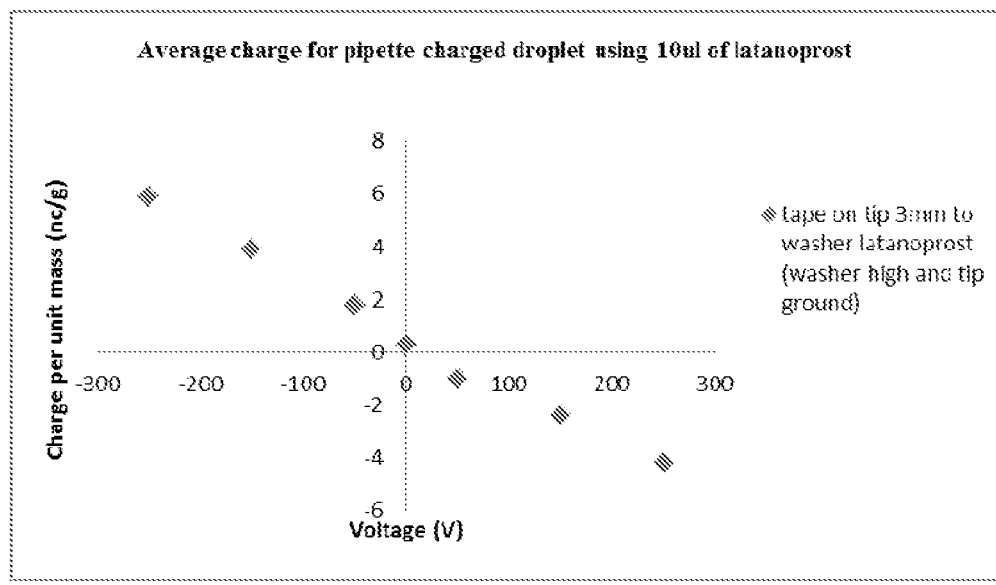

For comparison, FIGS. 33H-33I illustrate average charge data for pipette delivered droplets, showing an alternative mechanism for controlling charge on droplets.

Example 17

The purpose of this study is to analyze the surface interaction of droplets ejected via a spray ejector device of the disclosure with a positively charged glass slide. The study aims to emulate the charge difference between the surface of the eyes and the spray ejector device.

Materials and Methods

For this experiment a glass slide is used to simulate the surface of the eyes. A positive charge is induced in the glass slide. The charge in the spray ejector device is induced via a DC offset charge. The charge in the spray is measured via a Faraday Cage.

Results

With a positive charge spray, the droplets tend to bead on the glass slide surface. With a negative charge spray, the droplets tend to wet the glass slide surface.

Discussion

There is a noticeable difference in behavior in surface interaction depending on the charge difference between the droplets and the glass slide surface. In this regard, the surface of the eyes have a net negative charge, and therefore a positively charge spray can promote liquid distribution and adherence to the ocular surface. Likewise, negative charge can promote reduced run out from the ocular surface due to equivalent polarities of charge.

Example 18

This example relates to clinical studies using glaucomatous beagles to evaluate the effect of droplet charge on treatment.

Materials and Methods

In-vivo pharmacodynamic (PD) studies in glaucomatous beagles and pharmacokinetic (PK) studies in normal beagles have demonstrated superior intraocular pressure (IOP) lowering effects and significantly increased bioavailability of commercially available prostaglandin agonists sprayed onto the cornea with a spray ejector device of the disclosure (see Examples 2-15). The devices used for those studies were found to have a tribocharge and induced positive charge.

The studies of this example further investigate the effect of droplet charge on treatment Animal selection and administration of drug may be performed as described above in Examples 2-15. In these studies, 0.002%, 0.004%, or 0.0005% travoprost (Travatan Z®, Alcon Laboratories, Fort Worth, Tex. USA) were administered to animals via a spray ejector device of the invention with controllable droplet charge.

Results

Controllable droplet charging via a spray ejector device of the disclosure improves the IOP-lowering effects, lengthens duration of effect, and increases bioavailability of $PF_{2\alpha}$ prostaglandin agonist pro-drugs without the need for drug reformulation.

More particularly, as shown in FIGS. 34A-34H, lower doses of travoprost (3 microliters, 0.002% and 0.0005%) produce greater IOP lowering when delivered via a spray ejector device of the disclosure with controllable droplet charge. Controllable droplet charge spray administration achieve 3×IOP lowering effectiveness, with a corresponding 3× reduction in preservatives, and 4× bioavailability of the same class of $PF_{2\alpha}$ prostaglandin agonist drugs, as compared to traditional delivery with eyedropper or pipette. Controllable droplet charge spray administration provides prolonged IOP lowering effects of travoprost (with 1×qd@hs dosing), providing full 24 hour IOP lowering and reduces saw-tooth IOP curves observed with traditional administration. The data also suggests enhanced ligand receptor bias and possible enhanced biotransformation to the pharmacologically active form of travoprost occurs with controlled droplet charging administration.

Figure 34A:
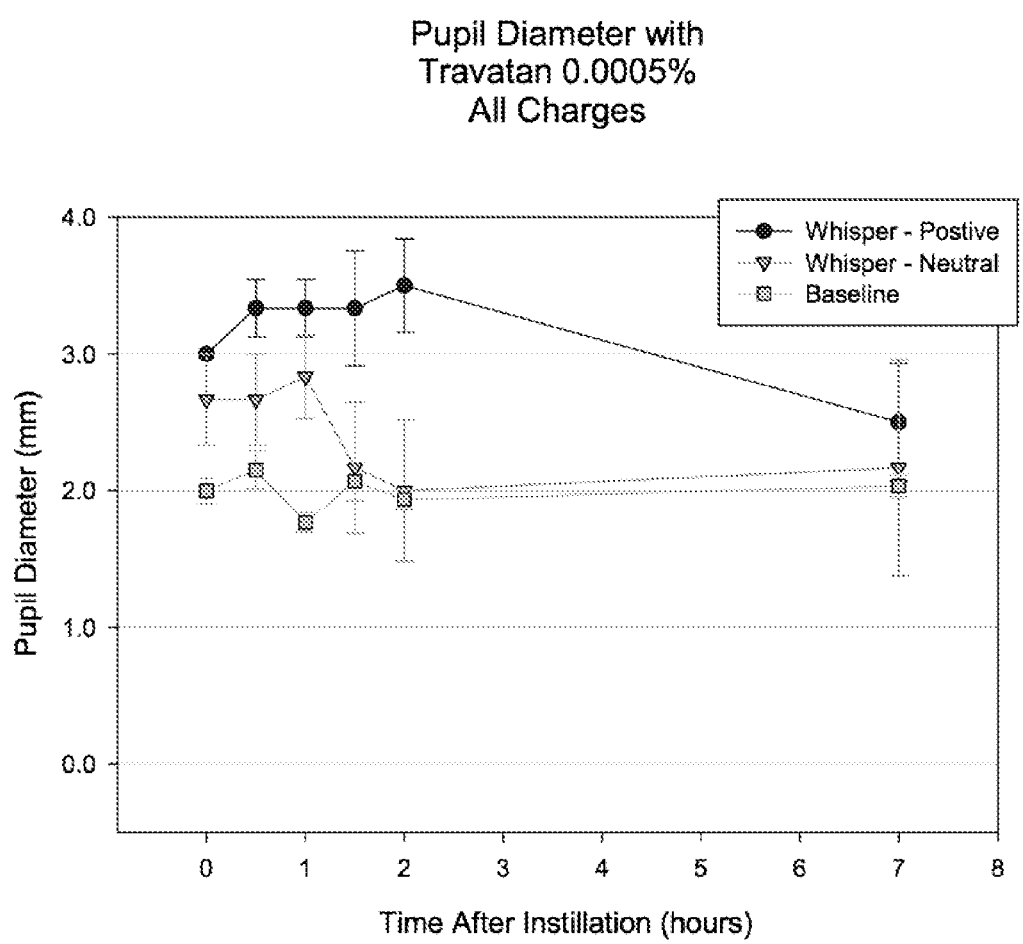
FIGS. 34A-34G illustrate pupil diameter and intraocular pressure following administration of travoprost (Travatan) via a spray ejector device with controllable droplet charge of the disclosure (Whisper—Positive, Whisper—Negative, Whisper—Neutral), compared to traditional pippette administration (Pippette—Neutral).
Figure 34B:
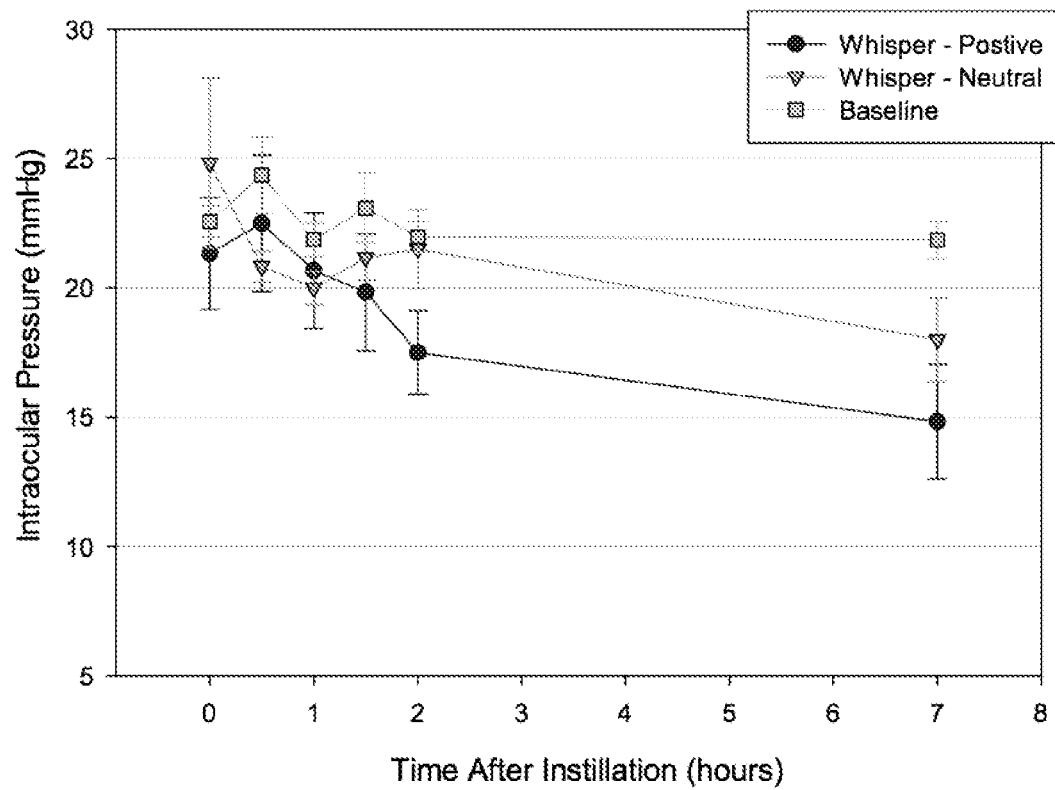
Figure 34C:
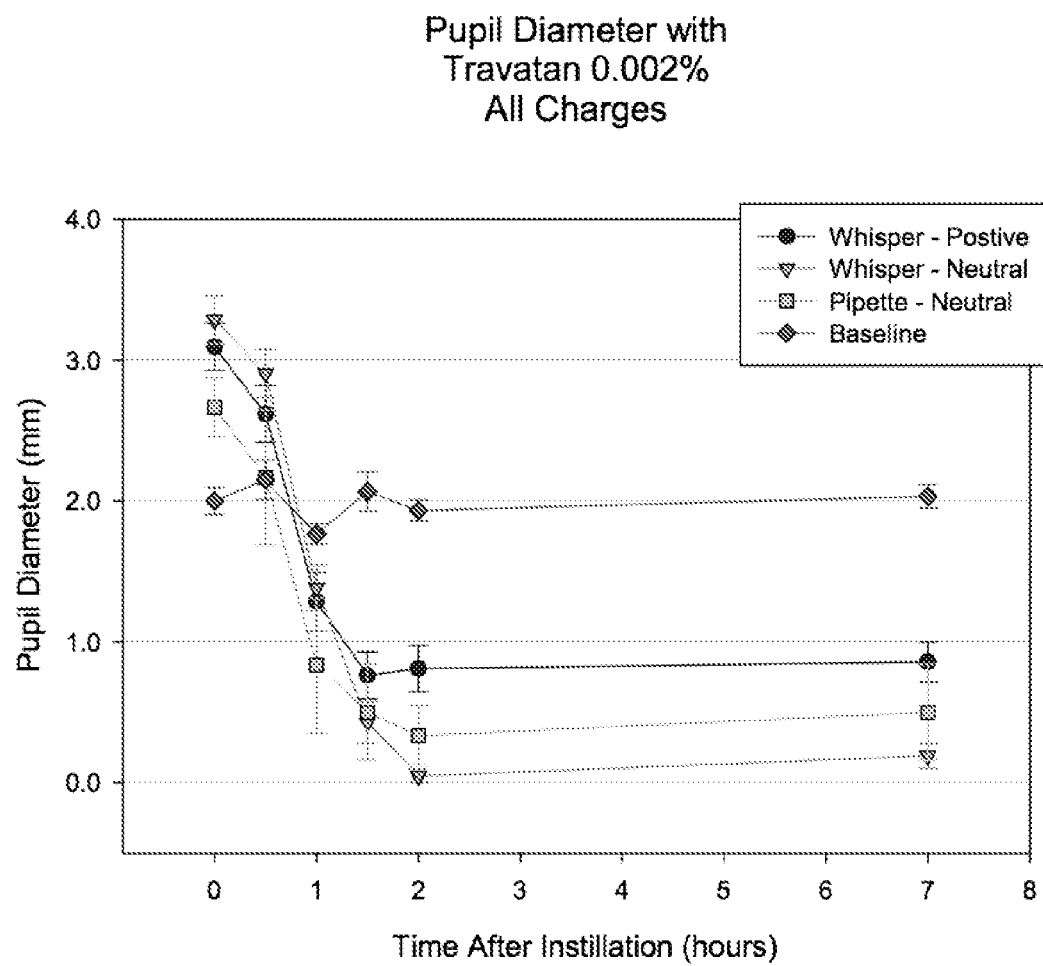
Figure 34D:
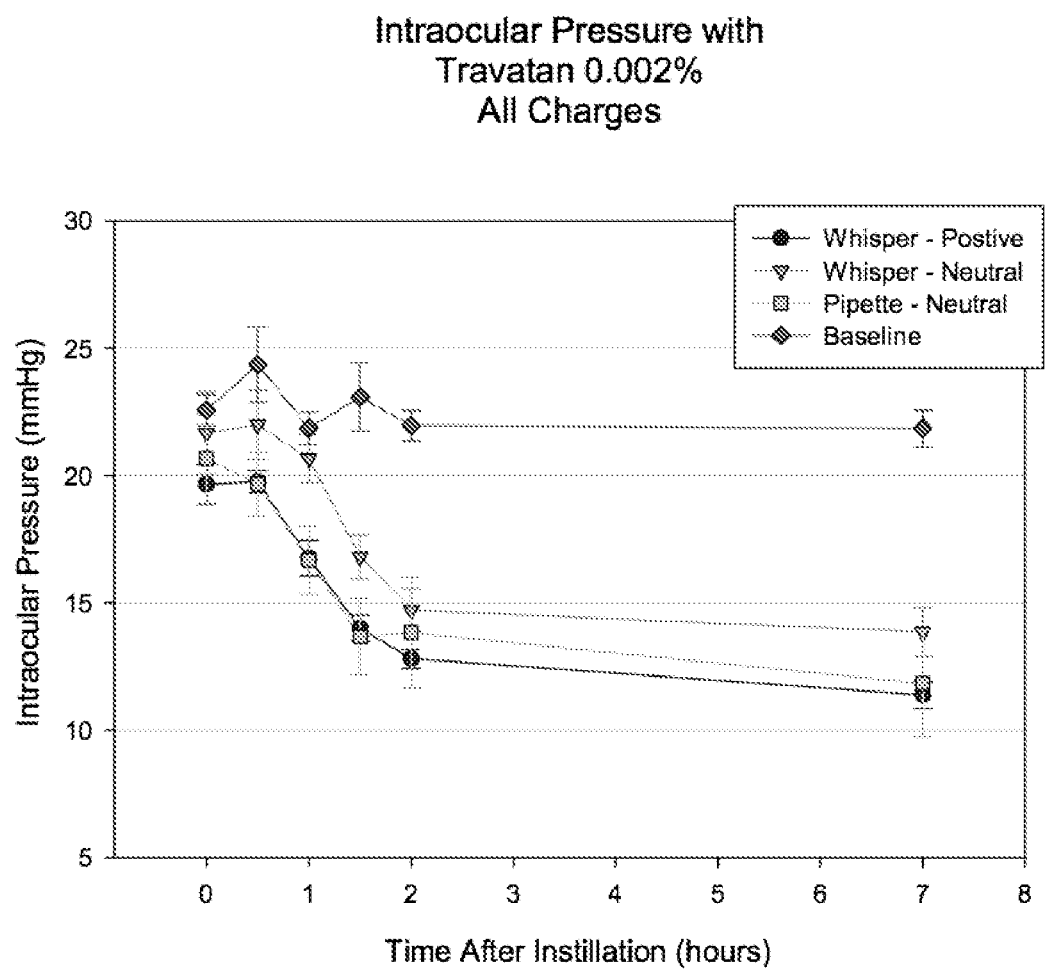
Figure 34E:
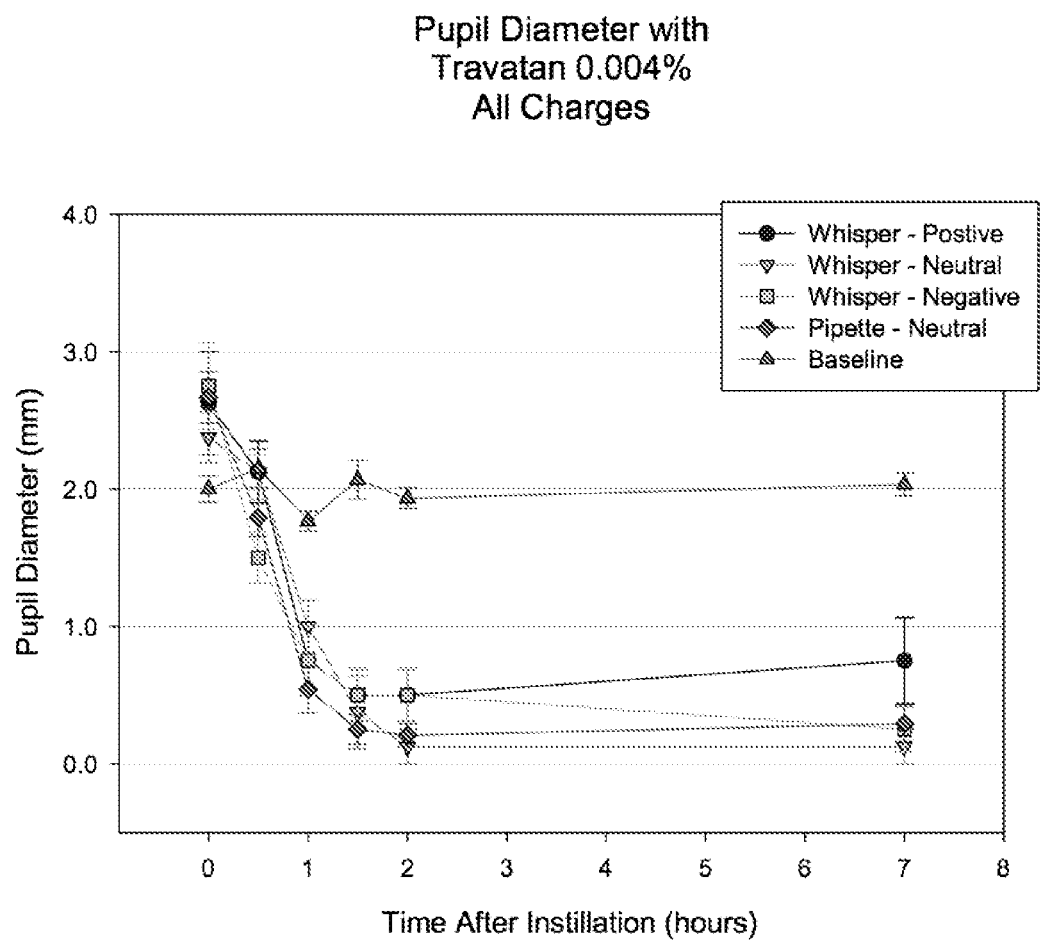
Figure 34F:
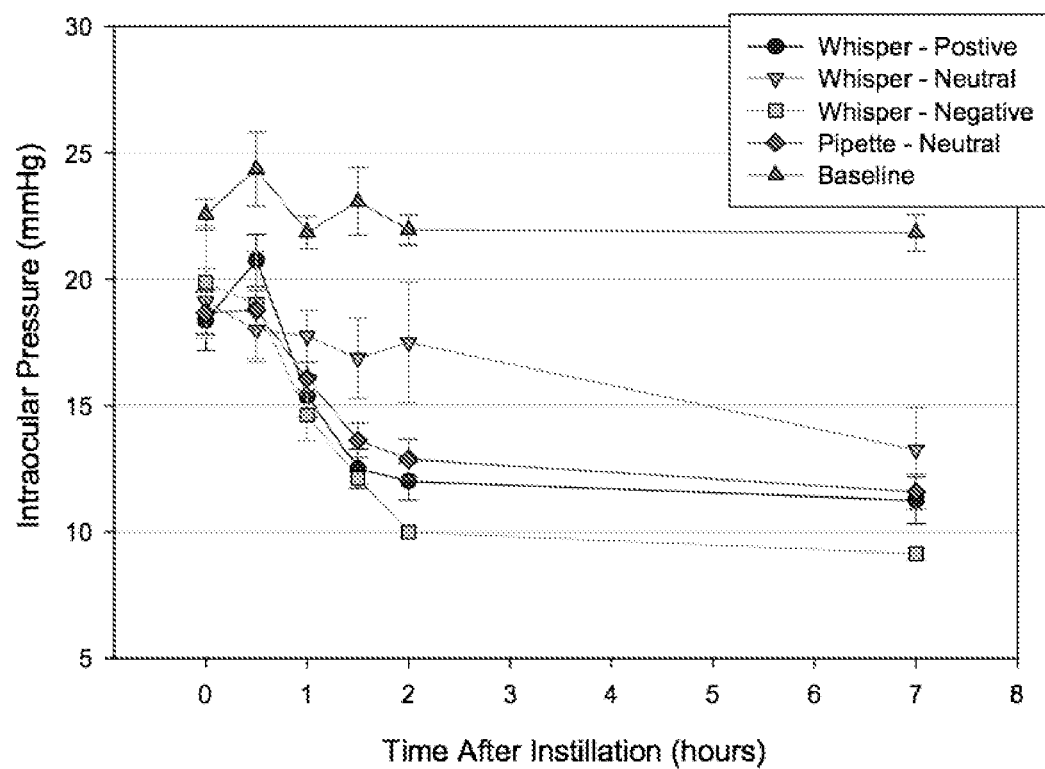
Figure 34G:
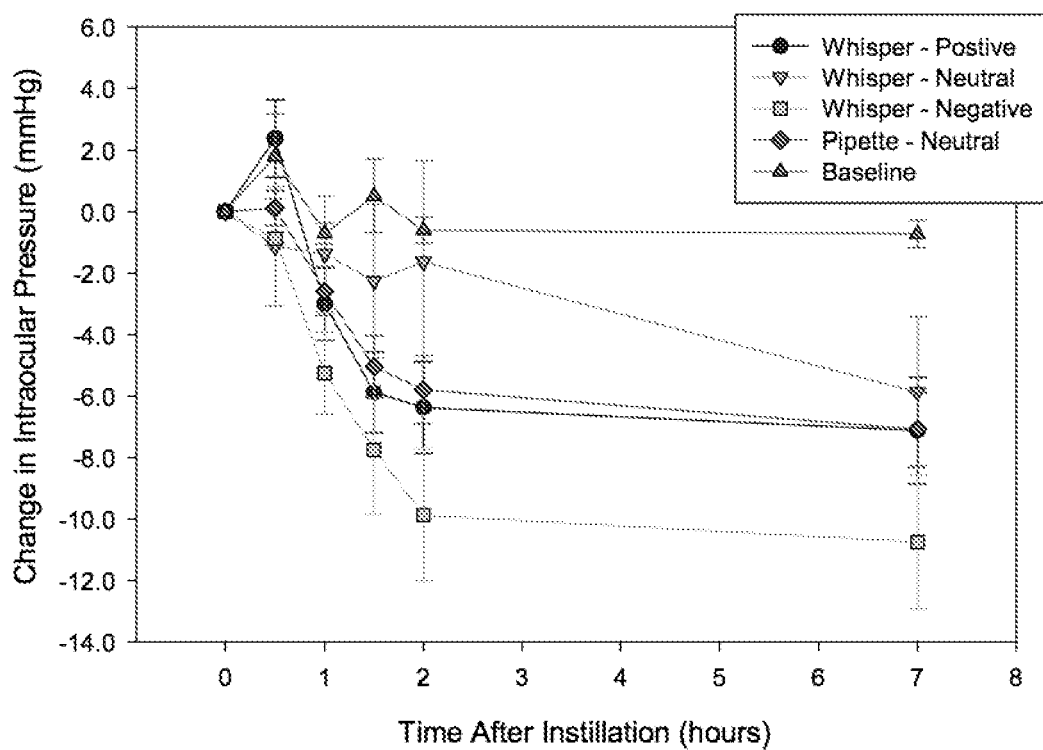
Figure 33G:
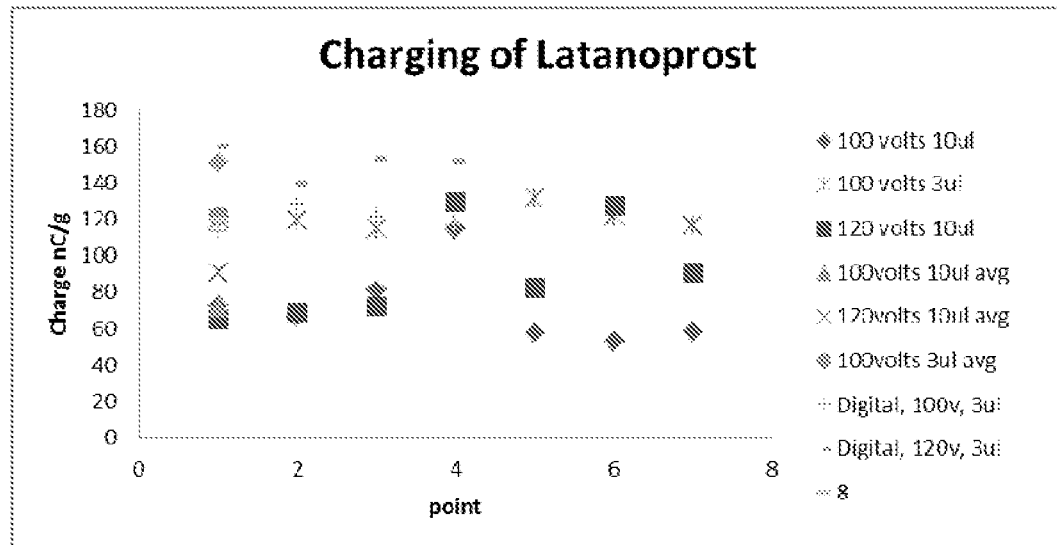
Figure 33H:
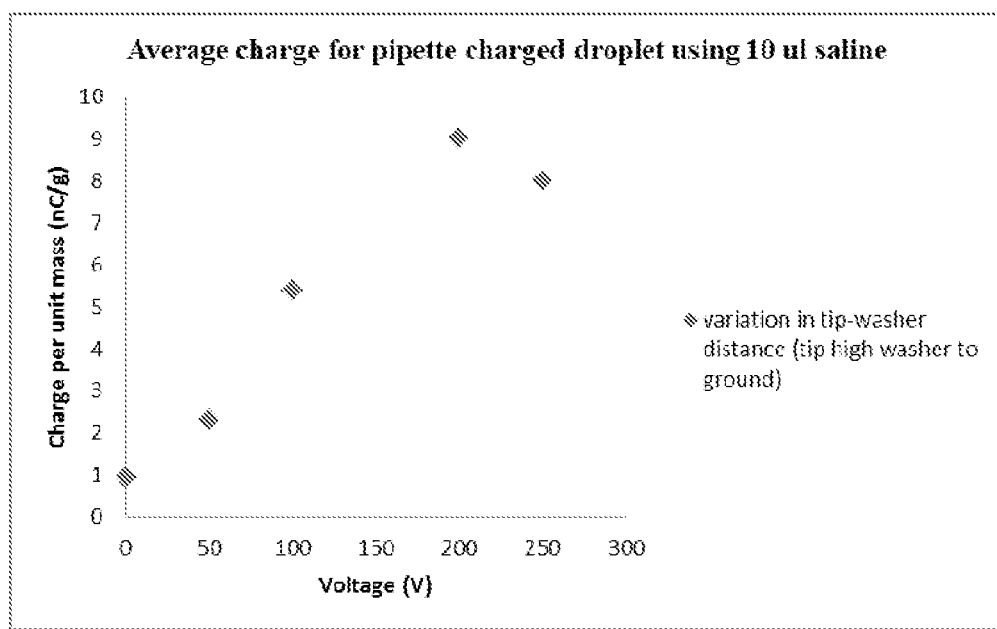
Figure 33I:
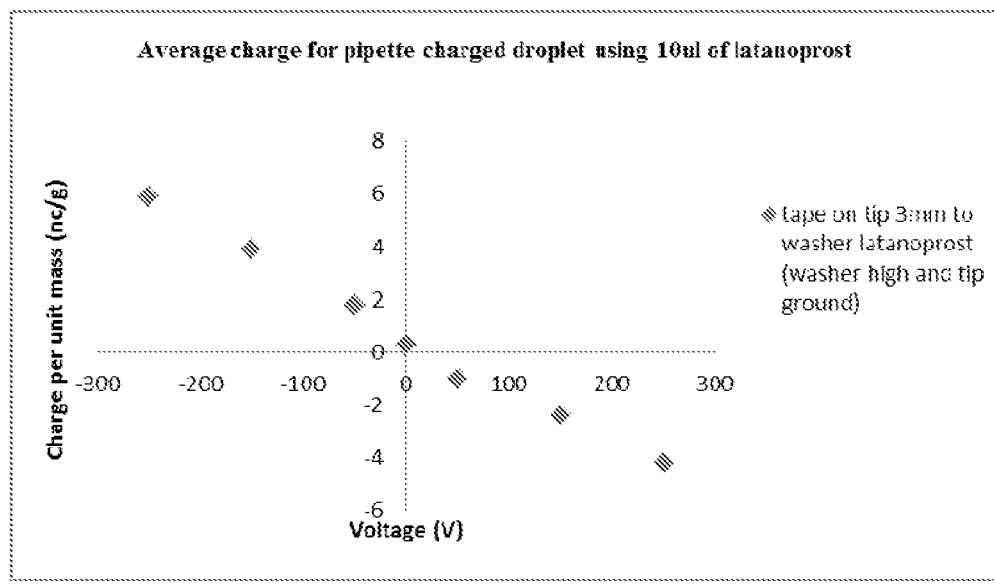
Figure 34A:
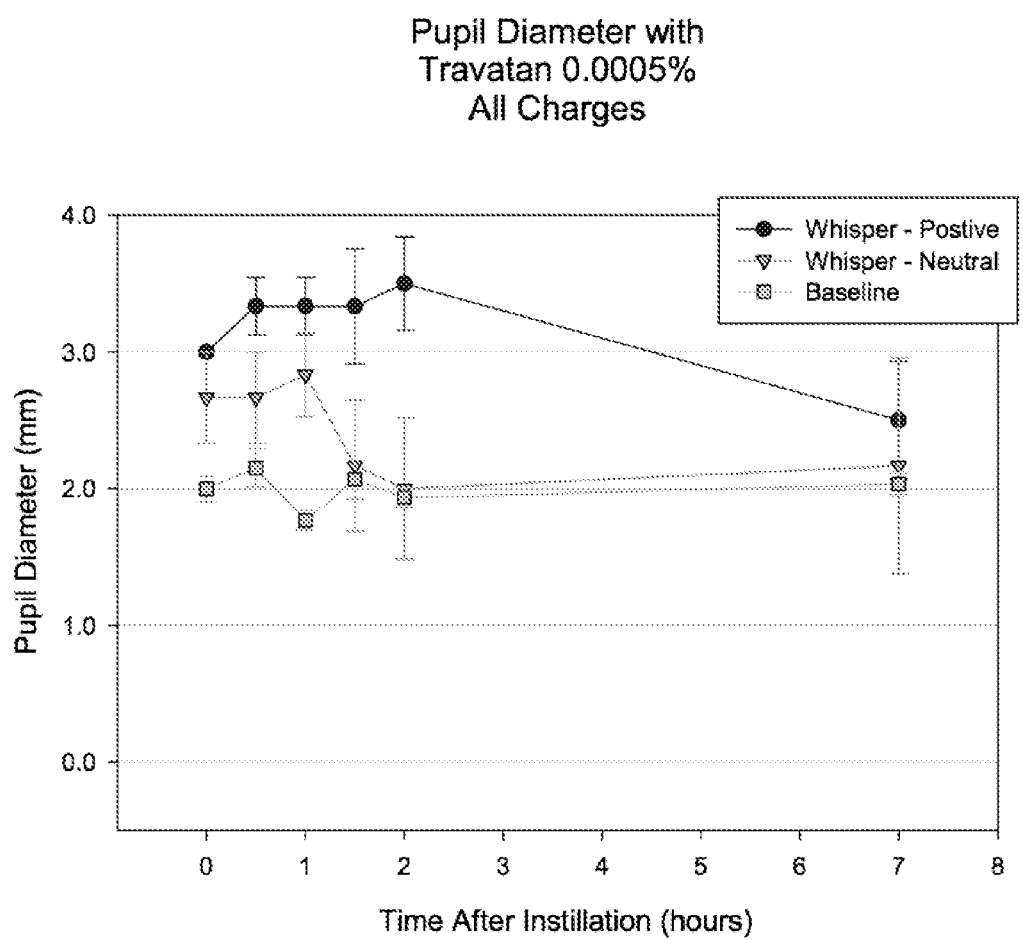
Figure 34B:
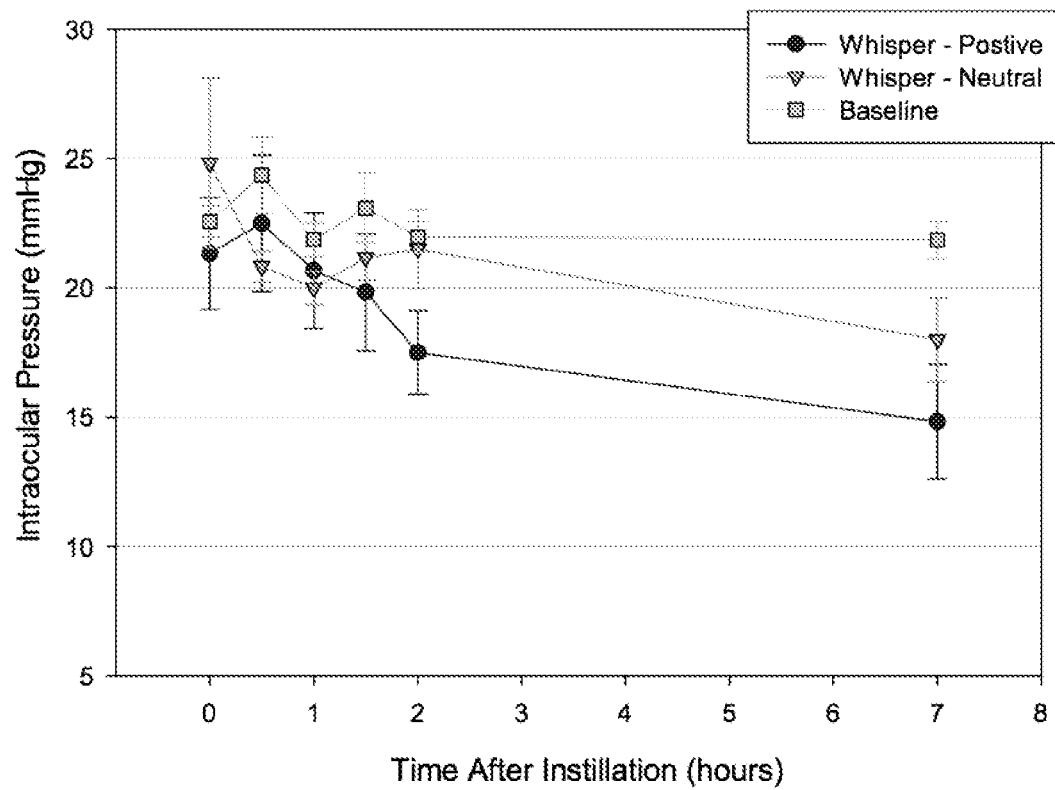
Figure 34C:
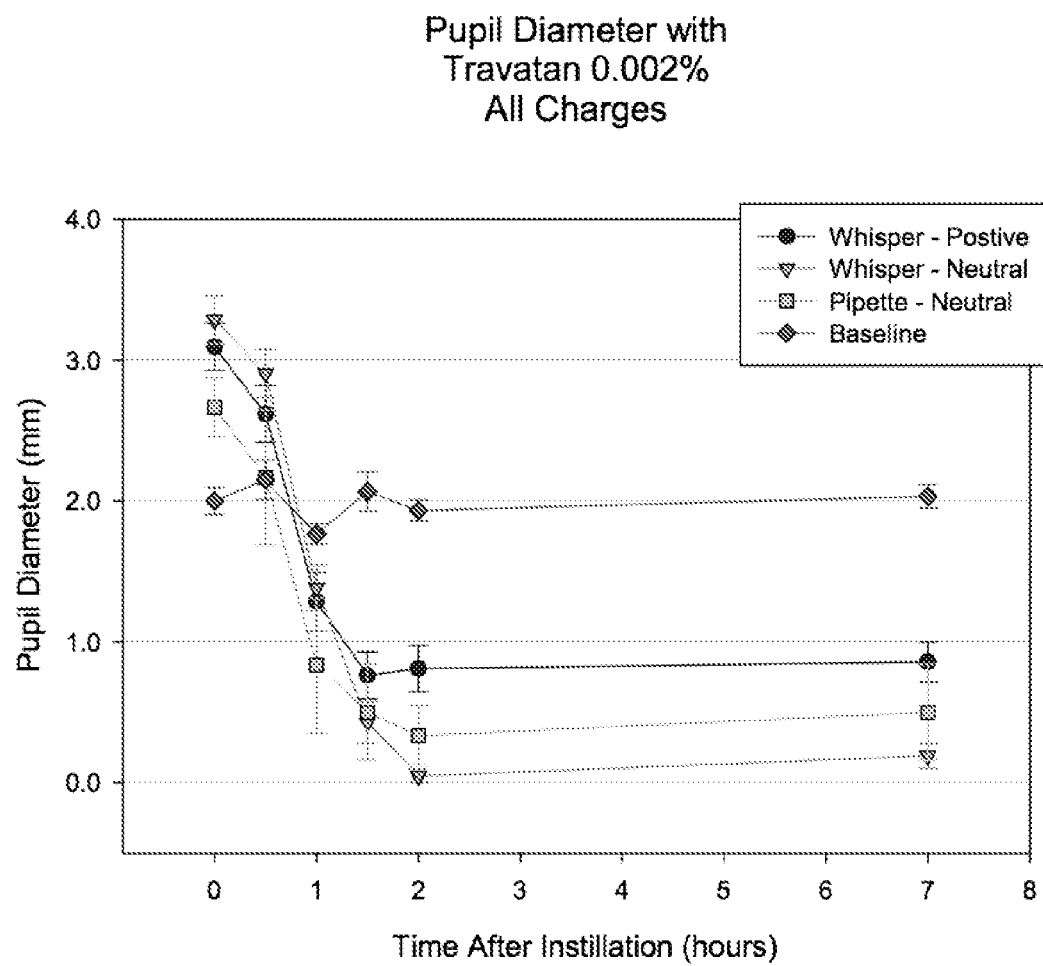
Figure 34D:
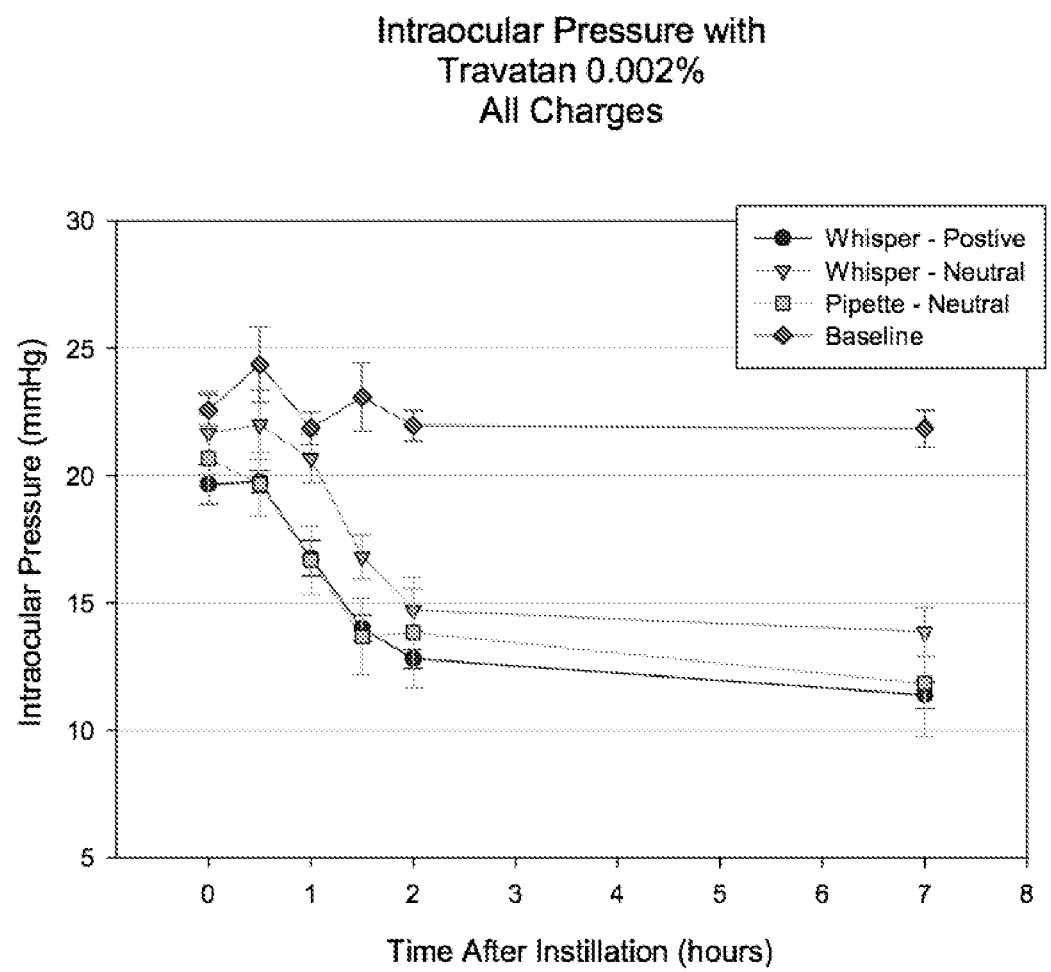
Figure 34E:
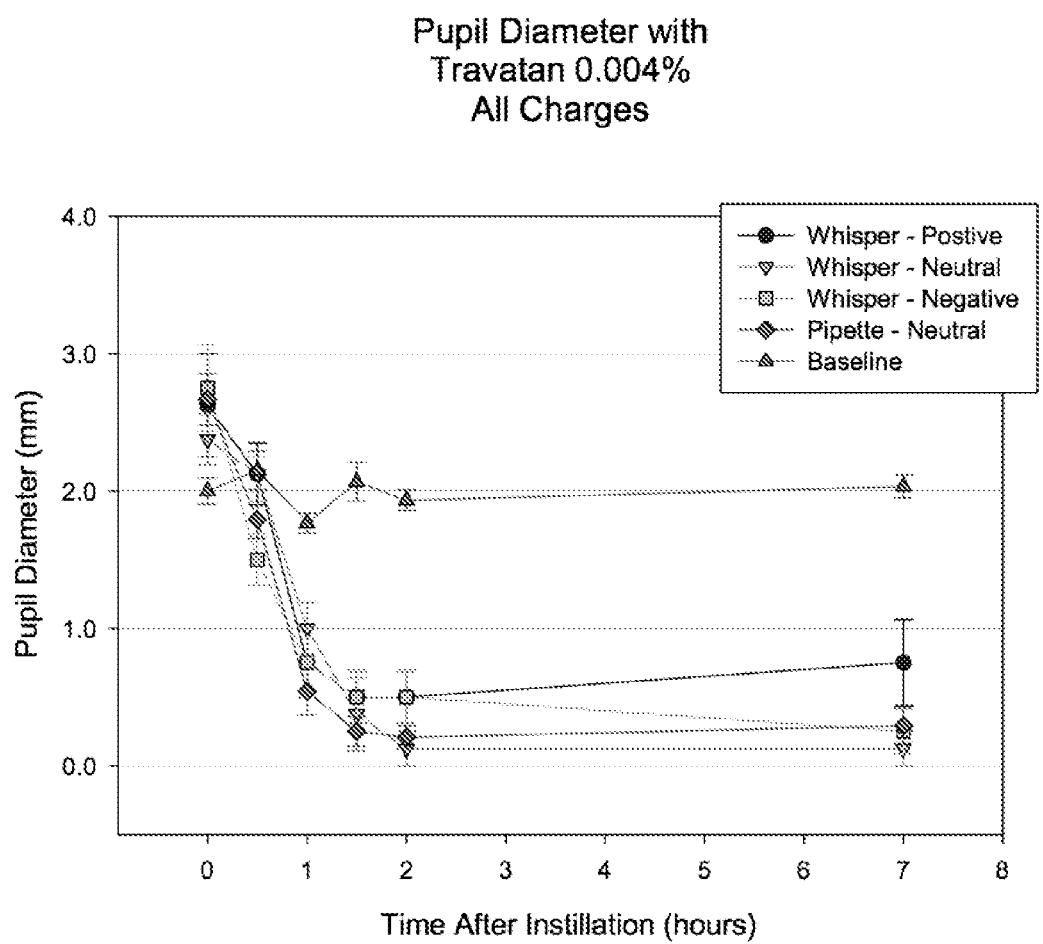
Figure 34F:
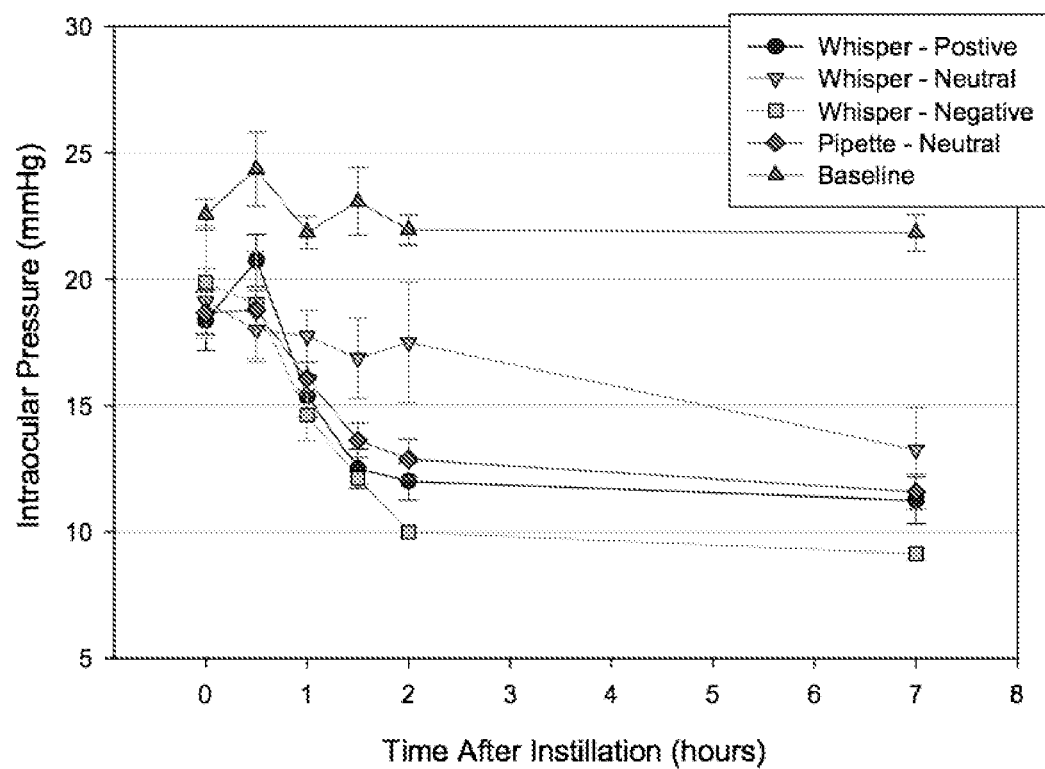
Figure 34G:
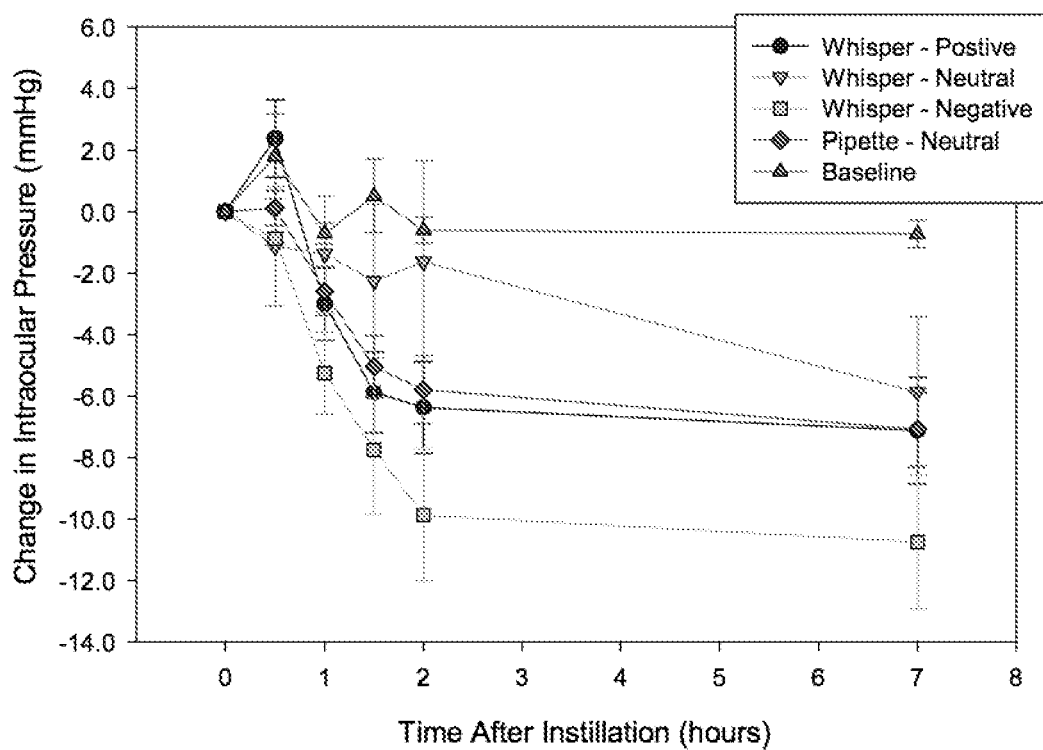

FIGS. 34A-34D show less decrease of pupillary diameter and greater IOP lowering (compared to uncharged droplets) with very low dose (0.0005%, 0.002%), positively charged travoprost (3mcl), suggesting possible ligand GPCR receptor bias. FIGS. 34C and 34D FIGS. 34E and 34F show paradoxical IOP/pupil diameter effect of both positive and negative controllable droplet charging spray administration of travoprost, suggesting binding by multiple receptors ($PF_{2a}$ prostaglandin agonist receptors, cationic and anionic receptors), biased ligand (drug) intracellular signaling, and accelerated biotransformation. FIGS. 34F and 34G show greater IOP lowering (compared to uncharged droplets) with 0.004%, positively and negatively charged travoprost, further suggesting that opposite charge adherence to the cornea is not the only mechanism of enhanced drug effect While this invention has been described with reference to exemplary embodiments, it will be understood by those skilled in the art that various changes may be made and equivalents may be substituted for elements thereof, without departing from the spirit and scope of the invention. In addition, modifications may be made to adapt the teachings of the invention to particular situations and materials, without departing from the essential scope thereof. Thus, the invention is not limited to the particular examples that are disclosed herein, but encompasses all embodiments falling within the scope of the appended claims.

What is claimed is:

1. A charge isolated ejector mechanism for generating droplets of a fluid comprising:
    a flexible printed circuit comprising a laminate structure including:
        (a) a generator plate having a fluid entrance side, a droplet exit side, and a plurality of openings formed through its thickness;
        (b) a piezoelectric actuator operable to directly or indirectly oscillate the generator plate upon application of a voltage;
        (c) a first conducting layer having a top surface opposite a bottom surface;
        (d) a dielectric layer having a top surface opposite a bottom surface; and
        (e) a second conducting layer having a top surface opposite a bottom surface;
    wherein:
    at least a portion of the top surface of the first conducting layer faces the piezoelectric actuator and at least a portion of the bottom surface of the first conducting layer faces at least a portion of the top surface of the dielectric layer to separate the piezoelectric actuator from the dielectric layer;
    at least a portion of the bottom surface of the dielectric layer faces the top surface of the second conducting layer to separate the first conducting layer from the second conducting layer; and
    at least a portion of the bottom surface of the second conducting layer faces the fluid entrance side of the generator plate to separate the dielectric layer from the generator plate;
    thereby charge isolating and grounding the generator plate.

2. The device of claim 1, wherein said ejector mechanism further comprises an ejector plate coupled to the generator plate; the piezoelectric actuator being operable to oscillate the ejector plate, and thereby the generator plate, and the second conducting layer separating the ejector plate from the dielectric layer.

3. The device of claim 2, wherein the ejector plate has a central open region aligned with the generator plate, and the piezoelectric actuator is coupled to a peripheral region of the ejector plate so as to not obstruct the plurality of openings of the generator plate.

4. The device of claim 3, wherein the plurality of openings of the generator plate are disposed in a center region of the generator plate that is uncovered by the piezoelectric actuator and aligned with the central open region of the ejector plate.

5. The device of claim 3, wherein the generator plate has a reduced size relative to the ejector plate, and the size of the generator plate is determined, at least in part, by the area occupied by the center region and the arrangement of the plurality of openings.

6. The ejector mechanism according to claim 1, further comprising one or more adhesive layers.

7. The ejector mechanism according to claim 1, further comprising at least one additional metalized layer.

8. A method of delivering a therapeutically effective low dosage volume medicament composition to an eye of a subject in need thereof, as compared to a standard eyedropper, the method comprising:
    (a) generating a directed stream of droplets including the low dosage volume medicament composition, wherein said stream of droplets is generated via the charge isolated ejector mechanism of claim 1; and
    (b) delivering the directed stream of droplets including the low dosage volume medicament composition to the eye of said subject,
    wherein the delivered stream of droplets including the low dosage volume medicament composition is deposited on the eye of said subject in less than ¾ of the volume of that of a standard eyedropper.

9. The method of claim 8, wherein the delivered stream of droplets including the therapeutically effective low dosage volume medicament composition is deposited on the eye of said subject in less than ½ of the volume of that of a standard eyedropper.

10. The method of claim 8, wherein the delivered stream of droplets including the therapeutically effective low dosage volume medicament composition is deposited on the eye of said subject in less than ¼ of the volume of that of a standard eyedropper.

11. The method of claim 8, wherein the therapeutically effective low dosage volume medicament composition comprises a higher concentration of medicament, as compared to a standard eyedropper composition.

12. The method of claim 8, wherein the directed stream of droplets is generated such that at least about 75% of the mass of the droplets deposit on the eye of said subject.

13. The method of claim 8, wherein the stream of droplets have an average droplet diameter in the range of 20 to 400 microns.

14. The method of claim 8, wherein the stream of droplets has an average initial velocity in the range of 0.5 m/s to 10 m/s.

15. The method of claim 8, wherein said medicament is a glaucoma medicament.

16. The method of claim 8, wherein said medicament is selected from the group consisting of travoprost, latanoprost, bimatoprost, dorzolamide HCl, timolol maleate, brimonidine tartrate, brinzolamide, dorzolamide HCl, and BAK-free latanoprost.

17. A method of claim 8, wherein said delivering a low dosage volume medicament composition is for the treatment, amelioration, or prevention of an eye disease, condition, discomfort, infection, or disorder in a subject in need thereof.

18. The method of claim 17, wherein said eye disease, condition, discomfort, infection, or disorder is glaucoma.

19. A method of delivering a therapeutically effective low dosage volume medicament composition to an eye of a subject in need thereof, as compared to dosage volume of a standard eyedropper, the method comprising:

(a) generating droplets including the low dosage volume medicament composition with a controllable droplet charge using a charge isolated ejector mechanism of claim 1; and (b) delivering the droplets including the low dosage volume medicament composition to the eye of the subject, wherein the controllable droplet charge improves delivery of the droplets to the eye of the subject, as compared to delivery via standard eyedropper.

20. The method of claim 19, wherein the delivered stream of droplets including the therapeutically effective low dosage volume medicament composition is deposited on the eye of said subject in less than ¾ of the volume of that of a standard eyedropper.

21. The method of claim 19, wherein the delivered stream of droplets including the therapeutically effective low dosage volume medicament composition is deposited on the eye of said subject in less than ½ of the volume of that of a standard eyedropper.

22. The method of claim 19, wherein the delivered stream of droplets including the therapeutically effective low dosage volume medicament composition is deposited on the eye of said subject in less than ¼ of the volume of that of a standard eyedropper.

23. The method of claim 19, wherein the therapeutically effective low dosage volume medicament composition comprises a higher concentration of medicament, as compared to a standard eyedropper composition.

24. The method of claim 19, where the improved delivery of the droplets to the eye of the subject comprising improved bioavailability of the medicament.

25. The method of claim 19, wherein said medicament is a glaucoma medicament.

26. The method of claim 19, wherein said medicament is selected from the group consisting of travoprost, latanoprost, bimatoprost, dorzolamide HCl, timolol maleate, brimonidine tartrate, brinzolamide, dorzolamide HCl, and BAK-free latanoprost.

27. A method of claim 19, wherein said delivering a low dosage volume medicament composition is for the treatment, amelioration, or prevention of an eye disease, condition, discomfort, infection, or disorder in a subject in need thereof.

28. The method of claim 27, wherein said eye disease, condition, discomfort, infection, or disorder is glaucoma.

* * * * *